United States Patent
Kohlman et al.

(10) Patent No.: US 6,828,332 B1
(45) Date of Patent: Dec. 7, 2004

(54) PIPERIDINE DERIVATIVES AS REUPTAKE INHIBITORS

(75) Inventors: Daniel Timothy Kohlman, Camby, IN (US); Sidney Xi Liang, Hamden, CT (US); Yao-Chang Xu, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 193 days.

(21) Appl. No.: 10/070,130

(22) PCT Filed: Sep. 14, 2000

(86) PCT No.: PCT/US00/20824

§ 371 (c)(1),
(2), (4) Date: Feb. 27, 2002

(87) PCT Pub. No.: WO01/23381

PCT Pub. Date: Apr. 5, 2001

Related U.S. Application Data

(60) Provisional application No. 60/157,343, filed on Sep. 29, 1999.

(51) Int. Cl.[7] ..................... C07D 401/02; A61K 31/445
(52) U.S. Cl. ..................... 514/332; 514/337; 546/255; 546/280.4; 546/283.4
(58) Field of Search .................... 546/255, 280.4, 546/283.4; 514/332, 337

(56) References Cited

FOREIGN PATENT DOCUMENTS

| EP | 0 812 826 | | 12/1997 | |
|----|-----------|---|---------|---|
| EP | 0 982 304 | | 3/2000 | |
| EP | 982304 | * | 3/2000 | ......... C07D/401/01 |
| WO | WO 9905140 | * | 7/1998 | ......... C07D/405/12 |
| WO | WO 99/05149 | | 4/1999 | |

* cited by examiner

*Primary Examiner*—Zinna Northington Davis
(74) *Attorney, Agent, or Firm*—Michael J. Sayles

(57) ABSTRACT

The present invention provides compounds of formula (I) and a method of inhibiting the reuptake of serotonin and antagonizing the serotonin receptor which comprises administering to a subject in need of such treatment an effective amount of a compound of formula (I).

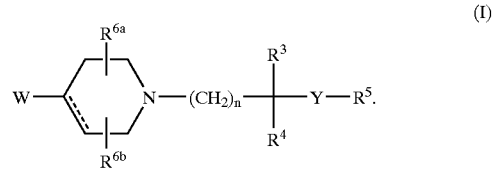

15 Claims, No Drawings

PIPERIDINE DERIVATIVES AS REUPTAKE INHIBITORS

This application claims the benefit of Patent Cooperation Treaty Application No. PCT/US00/20824, filed 14 Sep. 2000, and U.S. patent application Ser. No. 60/157,343, filed 29 Sep. 1999, the contents of which are herein incorporated by reference.

Pharmaceutical researchers have discovered in recent years that the neurons of the brain which contain monoamines are of extreme importance in a great many physiological processes which very strongly affect many psychological and personality-affecting processes as well. In particular, serotonin (5-hydroxytryptamine; 5-HT) has been found to be a key to a very large number of processes which affect both physiological and psychological functions. Drugs which influence the function of serotonin in the brain are accordingly of great importance and are now used for a surprisingly large number of different therapies.

The early generations of serotonin-affecting drugs tended to have a variety of different physiological functions, considered from both the mechanistic and therapeutic points of view. For example, many of the tricyclic antidepressant drugs are now known to be active as inhibitors of serotonin and norepinephrine reuptake, and also to have anticholinergic, antihistaminic or anti-α-adrenergic activity. More recently, it has become possible to study the function of drugs at individual receptors in vitro or ex vivo, and it has also been realized that therapeutic agents free of extraneous mechanisms of action are advantageous to the patient. Accordingly, the objective of research now is to discover agents which affect only functions of serotonin.

The present invention provides compounds which have selective activity as antagonists and partial agonists of the serotonin receptor, and activity as inhibitors of serotonin reuptake. A well-known pharmaceutical with the latter efficacy is fluoxetine, and the importance of its use in the treatment of depression and other conditions is extremely well documented and publicized. Recent scientific articles, for example, Artigas, *TIPS*, 14, 262 (1993), have suggested that the efficacy of a reuptake inhibitor may be decreased by the activation of serotonin-$1_A$ receptors with the resultant reduction in the firing rate of serotonin neurons. Compounds exhibiting both serotonin reuptake inhibition activity and 5-$HT_{1A}$ antagonist activity have been described, for example in U.S. Pat. No. 5,576,321, issued Nov. 19, 1996. In addition, International Patent Application WO 98/31686 published Jul. 23, 1996 discloses compounds which possess both serotonin reuptake inhibition activity and 5-$HT_{2A}$ antagonist activity.

The present invention provides compounds of formula I:

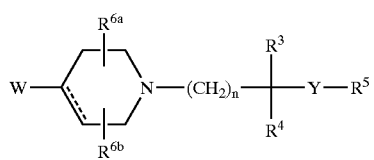

formula I wherein:
W represents:

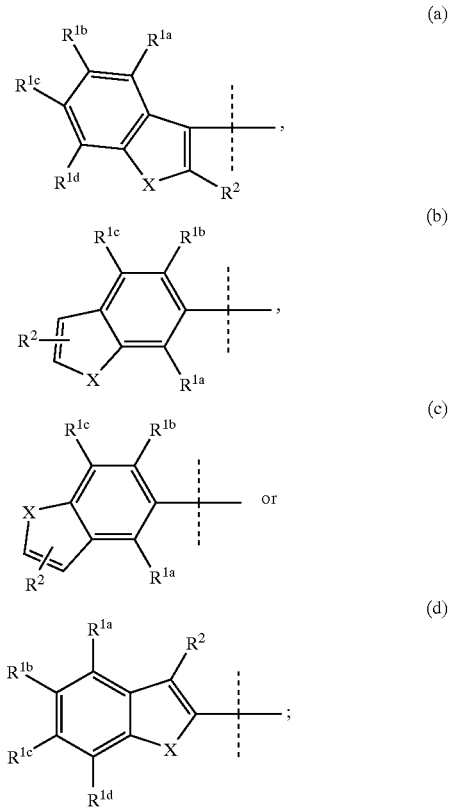

X represents O or S;
Y represents —C(=O)—, —CH(OH)—, —CH$_2$—, S, SO, or SO$_2$;
=== represents a single or a double bond;
n is 1, 2, 3 or 4;
$R^{1a}$, $R^{1b}$, $R^{1c}$, $R^{1d}$, and $R^2$ are each independently H, F, Cl, Br, I, OH, $C_1$–$C_6$ alkyl, $C_1$–$C_6$ alkoxy, halo($C_1$–$C_8$) alkyl, phenyl, NO$_2$, —NR$_7$R$_8$, CN or phenyl substituted with from 1 to 3 substituents selected from the group consisting of F, Cl, Br, I, OH, $C_1$–$C_6$ alkyl, $C_1$–$C_6$ alkoxy, halo($C_1$–$C_6$)alkyl, phenyl, NO$_2$, NH$_2$, or CN;
$R_3$ represents H, OH, hydroxy($C_1$–$C_6$)alkyl, $C_1$–$C_6$ alkyl, or $C_1$–$C_6$ alkoxy;
$R_4$ represents aryl, heterocycle, $C_3$–$C_8$ cycloalkyl, aryl substituted with from 1 to 3 substituents selected from the group consisting of F, Cl, Br, I, OH, $C_1$–$C_6$ alkyl, $C_1$–$C_6$ alkoxy, halo($C_1$–$C_6$)alkyl, phenyl, NO$_2$, NH$_2$, or CN; or heterocycle substituted with from 1 to 3 substituents selected from the group consisting of F, Cl, Br, I, OH, $C_1$–$C_6$ alkyl, $C_1$–$C_6$ alkoxy, halo($C_1$–$C_6$)alkyl, phenyl, NO$_2$, NH$_2$, or CN;
$R_5$ represents aryl, heterocycle, $C_3$–$C_8$ cycloalkyl, aryl substituted with from 1 to 3 substituents selected from the group consisting of F, Cl, Br, I, OH, $C_1$–$C_6$ alkyl, $C_1$–$C_6$ alkoxy, hydroxy($C_1$–$C_6$)alkyl, halo($C_1$–$C_6$) alkyl, phenyl, NO$_2$, NH$_2$, or CN; heterocycle substituted with from 1 to 3 substituents selected from the group consisting of F, Cl, Br, I, OH, $C_1$–$C_6$ alkyl, $C_1$–$C_6$ alkoxy, hydroxy($C_1$–$C_6$)alkyl, halo($C_1$–$C_6$) alkyl, phenyl, NO$_2$, NH$_2$, or CN; or $C_3$–$C_8$ cycloalkyl substituted with $C_1$–$C_4$ alkyl;

$R_{6a}$ and $R_{6b}$ are each independently H or $C_1$–$C_3$ alkyl;

$R_7$ and $R_8$ are each independently H, $C_1$–$C_6$ alkyl, aryl or aryl substituted with from 1 to 3 substituents selected from the group consisting of F, Cl, Br, I, OH, $C_1$–$C_6$ alkyl, $C_1$–$C_6$ alkoxy, halo($C_1$–$C_6$)alkyl, phenyl, $NO_2$, $NH_2$, or CN;

or a pharmaceutically acceptable salt thereof.

The present invention further provides a method of inhibiting the reuptake of serotonin and antagonizing the serotonin receptor which comprises administering to a subject in need of such treatment an effective amount of a compound of formula I.

More particularly, the present invention provides a method for alleviating the symptoms caused by withdrawal or partial withdrawal from the use of tobacco or of nicotine; a method of treating anxiety; and a method of treating a condition chosen from the group consisting of depression, hypertension, cognitive disorders, psychosis, sleep disorders, gastric motility disorders, sexual dysfunction, brain trauma, memory loss, eating disorders and obesity, substance abuse, obsessive-compulsive disease, panic disorder and migraine; which methods comprise administering to a subject in need of such treatment an effective amount of a compound of formula I.

In addition, the present invention provides a method of potentiating the action of a serotonin reuptake inhibitor comprising administering to a subject in need of such treatment a compound of formula I in combination with a serotonin reuptake inhibitor.

In addition, the invention provides pharmaceutical compositions of compounds of formula I, including the hydrates thereof, comprising, as an active ingredient, a compound of formula I in combination with a pharmaceutically acceptable carrier, diluent or excipient. This invention also encompasses novel intermediates, and processes for the synthesis of the compounds of formula I.

According to another aspect, the present invention provides the use of a compound of formula I for the manufacture of a medicament for inhibiting the reuptake of serotonin and antagonizing the serotonin receptor.

In addition, the present invention provides the use of a compound of formula I for inhibiting the reuptake of serotonin and antagonizing the serotonin receptor.

It is understood that the compounds of formula IIa:

formula IIa

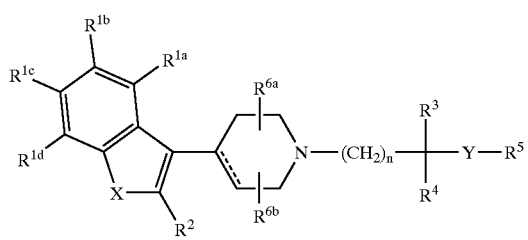

fall within the scope of formula I, the corresponding substituents have the same meaning as defined in formula I, and it is further understood that the compounds of formula IIa are included within the scope of the present invention.

It is understood that the compounds of formula IIb:

formula IIb

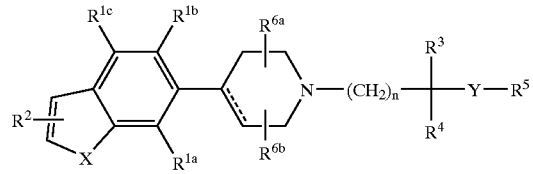

fall within the scope of formula I, the corresponding substituents have the same meaning as defined in formula I, and it is further understood that the compounds of formula IIb are included within the scope of the present invention.

It is understood that the compounds of formula IIc:

formula IIc

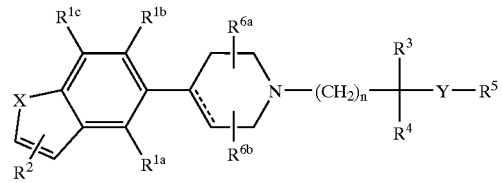

fall within the scope of formula I, the corresponding substituents have the same meaning as defined in formula I, and it is further understood that the compounds of formula IIc are included within the scope of the present invention.

It is understood that the compounds of formula IId:

formula IId

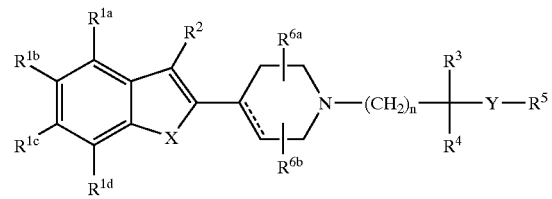

fall within the scope of formula I, the corresponding substituents have the same meaning as defined in formula I, and it is further understood that the compounds of formula IId are included within the scope of the present invention.

In addition, it has been discovered that compounds of formulas IIa–IId have selective binding affinity at particular serotonin receptors. Thus, the present invention further provides a method of inhibiting the reuptake of serotonin, antagonizing the 5-$HT_{1A}$ receptor, antagonizing the 5-$HT_{2A}$ receptor, and antagonizing the 5-$HT_{1D}$ receptor which comprises administering to a subject in need of such treatment an effective amount of a compound of formula IIa.

In addition, the present invention provides a method of inhibiting the reuptake of serotonin, antagonizing the 5-$HT_{1A}$ receptor, and antagonizing the 5-$HT_{2A}$ receptor which comprises administering to a subject in need of such treatment an effective amount of a compound of formula IIb.

The present invention further provides a method of inhibiting the reuptake of serotonin, antagonizing the 5-$HT_{1A}$ receptor, and antagonizing the 5-$HT_{2A}$ receptor which comprises administering to a subject in need of such treatment an effective amount of a compound of formula IIc.

In addition, the present invention provides a method of inhibiting the reuptake of serotonin, and antagonizing the 5-HT$_{2A}$ receptor which comprises administering to a subject in need of such treatment an effective amount of a compound of formula IId.

As used herein, an acyclic or cyclic acetal or ketal is represented by the following:

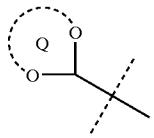

and corresponds for example, to the following groups:

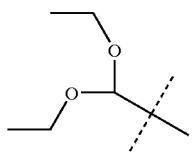 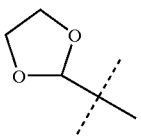

As used herein the term "Pg" refers to a protecting group on the amine which are commonly employed to block or protect the amine while reacting other functional groups on the compound. Examples of protecting groups (Pg) used to protect the amino group and their preparation are disclosed by T. W. Greene, "Protective Groups in Organic Synthesis," John Wiley & Sons, 1981, pages 218–287. Choice of the protecting group used will depend upon the substituent to be protected and the conditions that will be employed in subsequent reaction steps wherein protection is required, and is well within the knowledge of one of ordinary skill in the art. Preferred protecting groups are t-butoxycarbonyl also known as a BOC protecting group, and benzyloxycarbonyl.

As used herein, the terms "Halo", "Halide" or "Hal" refers to a chlorine, bromine, iodine or fluorine atom, unless otherwise specified herein.

As used herein, the term "Me", refers to a methyl group, the term "Et" refers to an ethyl group, the term "Pr" refers to a propyl group, the term "iPr" refers to an isopropyl group, "Bu" refers to a butyl group, and the term "Ph" refers to a phenyl group.

As used herein the term "serotonin" is equivalent to and interchangeable with the terms "5-HT" or "5-hydroxytryptamine".

As used herein the term "C$_1$–C$_6$ alkyl" refers to straight or branched, monovalent, saturated aliphatic chains of 1 to 6 carbon atoms and includes, but is not limited to, methyl, ethyl, propyl, isopropyl, butyl, isobutyl, t-butyl, pentyl, isopentyl, and hexyl. The term "C$_1$–C$_6$ alkyl" includes within its definition the term "C$_1$–C$_4$ alkyl" and "C$_1$–C$_3$ alkyl".

As used herein the term "halo(C$_1$–C$_6$)alkyl" refers to a straight or branched alkyl chain having from one to six carbon atoms with 1, 2 or 3 halogen atoms attached to it. Typical halo(C$_1$–C$_6$)alkyl groups include chloromethyl, 2-bromoethyl, 1-chloroisopropyl, 3-fluoropropyl, 2,3-dibromobutyl, 3-chloroisobutyl, iodo-t-butyl, trifluoromethyl and the like. The term "halo(C$_1$–C$_6$)alkyl" includes within its definition the term "halo(C$_1$–C$_4$)alkyl".

As used herein the term "hydroxy(C$_1$–C$_6$)alkyl" refers to a straight or branched alkyl chain having from one to six carbon atoms with a hydroxy group attached to it, such as —CH$_2$OH, —CH$_2$CH$_2$OH, —CH$_2$CH$_2$CH$_2$OH, and the like. The term "hydroxy(C$_1$–C$_6$)alkyl" includes within its definition the term "hydroxy(C$_1$–C$_4$)alkyl".

As used herein the term "(C$_1$–C$_6$)alkylthio" refers to a straight or branched alkyl chain having from one to six carbon atoms attached to a sulfur atom.

Typical (C$_1$–C$_6$)alkylthio groups include —SCH$_3$, —SCH$_2$CH$_3$, —S(CH$_2$)$_2$CH$_3$, —S(CH$_2$)$_3$CH$_3$, —S(CH$_2$)$_4$CH$_3$, —S(CH$_2$)$_5$CH$_3$, and the like. The term "(C$_1$–C$_6$)alkylthio" includes within its definition the term "(C$_1$–C$_4$)alkylthio".

As used herein the term "C$_1$–C$_6$ alkoxy" refers to a straight or branched alkyl chain having from one to six carbon atoms attached to an oxygen atom. Typical C$_1$–C$_6$ alkoxy groups include methoxy, ethoxy, propoxy, isopropoxy, butoxy, t-butoxy, pentoxy and the like. The term "C$_1$–C$_6$ alkoxy" includes within its definition the term "C$_1$–C$_4$ alkoxy".

As used herein the term "C$_3$–C$_8$ cycloalkyl" refers to a saturated hydrocarbon ring structure containing from three to eight carbon atoms. Typical C$_3$–C$_8$ cycloalkyl groups include cyclopropyl, cyclobutyl, cyclopentyl, cyclohexyl, cycloheptyl, cyclooctyl, and the like.

As used herein the term "aryl" refers to a phenyl or naphthyl group.

As used herein the term "heterocycle" refers to a stable 5- to 7-membered monocyclic or 7- to 10-membered bicyclic heterocyclic ring which is saturated or unsaturated, and consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quaternized and including a bicyclic group in which any of the above-defined heterocyclic rings is fused to a benzene ring. The heterocyclic ring may be attached at any heteroatom or carbon atom which affords a stable structure.

Examples of such heterocycles include piperidinyl, piperazinyl, azepinyl, pyrrolyl, pyrrolidinyl, pyrazolyl, pyrazolidinyl, imidazolyl, imidazolinyl, imidazolidinyl, pyridyl, pyridyl N-oxide, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazolyl, benzopyranyl, benzothiazolyl, benzoazolyl, furyl, tetrahydrofuryl, tetrahydropyranyl, thienyl, benzothienyl, thiamorpholinyl, thiamorpholinyl-sulfoxide, thiamorpholinylsulfone, oxadiazolyl, triazolyl, tetrahydroquinolinyl, tetrahydrisoquinolinyl, and the like.

This invention includes the hydrates and the pharmaceutically acceptable salts of the compounds of formula I. A compound of this invention can possess a sufficiently basic functional group which can react with any of a number of inorganic and organic acids, to form a pharmaceutically acceptable salt.

The term "pharmaceutically acceptable salt" as used herein, refers to salts of the compounds of formula I which are substantially non-toxic to living organisms. Typical pharmaceutically acceptable salts include those salts prepared by reaction of the compounds of the present invention with a pharmaceutically acceptable mineral or organic acid. Such salts are also known as acid addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate. dihydrogenphosphate, metaphosphate, pyrophosphate, hydrobromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, γ-hydroxybutyrate, glycolate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid, oxalic acid and methanesulfonic acid.

It should be recognized that the particular counterion forming a part of any salt of this invention is usually not of a critical nature, so long as the salt as a whole is pharmacologically acceptable and as long as the counterion does not contribute undesired qualities to the salt as a whole. It is further understood that such salts may exist as a hydrate.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" referes to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 50:30 is achieved, the ee with respect to the first enantiomer is 25%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the enantiomers of compounds of formulas I or Ia can be resolved by one of ordinary skill in the art using standard techniques well known in the art, such as those described by J. Jacques, et al., "Enantiomers, Racemates, and Resolutions", John Wiley and Sons, Inc., 1981. Examples of resolutions include recrystallization techniques or chiral chromatography.

Some of the compounds of the present invention have one or more chiral centers and may exist in a variety of stereoismeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103–120.

As used herein, the term "SRI" refers to serotonin reuptake inhibitor.

The compounds of formula I can be prepared by techniques and procedures readily available to one of ordinary skill in the art, for example by following the procedures as set forth in the following Schemes. These schemes are not intended to limit the scope of the invention in any way. All substituents, unless otherwise indicated, are previously defined. The reagents and starting materials are readily available to one of ordinary skill in the art. Scheme I provides a synthesis of compounds of structure (8).

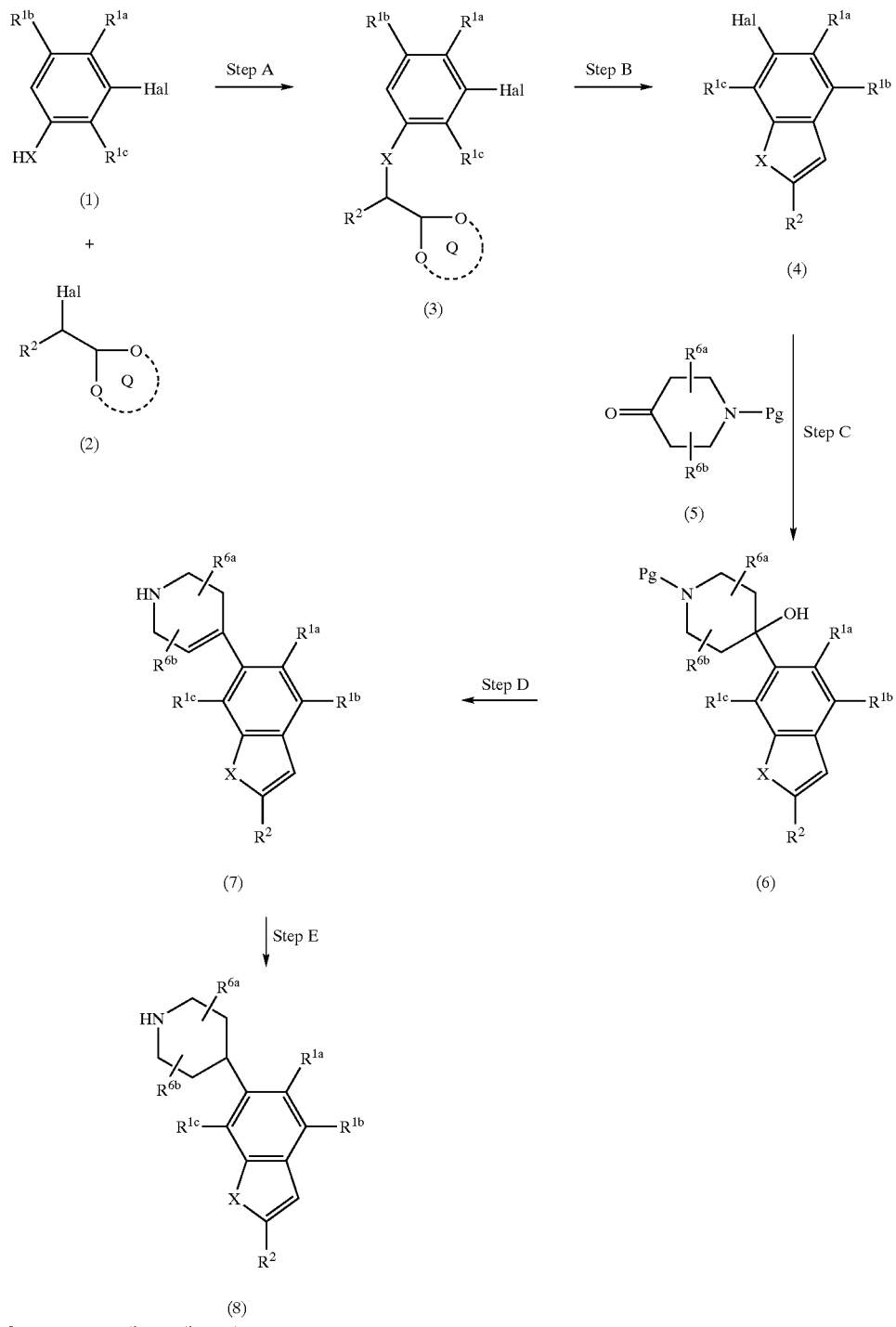
Q represents an acyclic or cyclic acetal
Pg represents a protecting group In Scheme I, step A, the compound of structure (1) is alkylated with a compound of structure (2) under conditions well known in the art. For example, compound (1) is dissolved in a suitable organic solvent, such as dimethylformamide (DMF) or tetrahydrofuran (THF). Examples of compound (1) include 3-bromothiophenol, 3-bromophenol, 2,5-dichlorobenzenethiol, 3,5-dichlorobenzenethiol, and the like. As used in Scheme I, Hal represents Cl, Br or I only. The solution is treated with a slight excess of a suitable base, such as potassium carbonate or sodium hydride followed by addition of about 1.05 to about 1.20 equivalents of compound (2). Examples of compound (2) include bromoacetaldehyde diethyl acetal, 2-bromomethyl-1,3dioxolane and the like. The reaction mixture is then stirred at room temperature to reflux for about 1 to 7 hours. The product is then isolated and purified by extraction techniques and chromatography. For example, the reaction is diluted with water and extracted with a suitable organic solvent, such as ethyl acetate. The organic extracts are combined, dried over anhydrous sodium sulfate, filtered and concentrated under vacuum. The residue is then purified by flash chromatography on silica gel with a suitable eluent, such as ethyl acetate/hexane to provide compound (3).

In Scheme I, step B, compound (3) is cyclized to the compound of structure (4) under acidic conditions. For example, compound (3) is dissolved in a suitable organic solvent, such as chlorobenzene and the solution is added dropwise to a refluxing mixture of polyphosphoric acid and chlorobenzene. The reaction mixture is heated at reflux for about 2 to 5 hours and then cooled to room temperature. The compound (4) is then isolated and purified by techniques well known in the art. For example, the reaction mixture is made slightly basic with 1N sodium hydroxide and then extracted with a suitable organic solvent, such as ethyl acetate. The organic extracts are combined, dried over anhydrous sodium sulfate, filtered and concentrated under vacuum. The residue is then purified by flash chromatography on silica gel with a suitable eluent, such as hexane or ethyl acetate/hexane to provide the compound (4).

In Scheme I, step C, compound (4) undergoes an aldol reaction with the piperidone of structure (5) under standard conditions well known in the art, such as Grignard Type conditions (See for example J. March, "Advanced Organic Chemistry: Reactions, Mechanisms, and Structure," $2^{nd}$ Edition, McGraw-Hill, 1977, 836–841.), to provide the alcohol of structure (6). For example, compound (4) is dissolved in a suitable organic solvent, such as diethyl ether and the solution is added dropwise to a mixture of about2 equivalents of magnesium suspended in diethyl ether. If necessary, about 1 equivalent of dibromoethane is then added and the reaction is heated to reflux for about 1 to 5 hours. The reaction is then cooled to room temperature and about 1 equivalent of the piperidone (5) is added to the prepared Grignard reagent. The reaction is then allowed to stir at room temperature for about 5 to 18 hours. The reaction is quenched by addition of water and the alcohol (6) is isolated and purified by techniques well known in the art. For example, the quenched reaction is extracted with a suitable organic solvent, such as diethyl ether, the organic extracts are combined, dried over anhydrous sodium sulfate, filtered and concentrated under vacuum. The residue is then purified by flash chromatography on silica gel with a suitable eluent, such as ethyl acetate/hexane to provide alcohol (6).

In Scheme I, step D, alcohol (6) is deprotected and dehydrated under standard conditions well known in the art to provide the 1,2,3,6-tetrahydropyridine of structure (7). One of ordinary skill in the art would readily appreciate that deprotection and dehydration can be carried out in a step-wise fashion, in any order, or concomitantly. For example, step D is carried out concomitantly by dissolving the alcohol (6) in a suitable organic solvent, such as toluene and treating the solution with an excess of a suitable acid, such as p-toluenesulfonic acid. The reaction is heated at reflux for about 1 to 4 hours, then cooled and the solution is made basic with a suitable base, such as 1N sodium hydroxide. The 1,2,3,6-tetrahydropyridine (7) is then isolated and purified by techniques well known in the art. For example, the solution is extracted with a suitable organic solvent, such as ethyl acetate, the organic extracts are combined, dried over anhydrous sodium sulfate, filtered and concentrated under vacuum. The residue can then be purified if necessary by flash chromatography on silica gel with a suitable eluent, such as ethyl acetate/hexane to provide 1,2,3,6-tetrahydropyridine (7).

In Scheme I, step E, 1,2,3,6-tetrahydropyridine (7) can be hydrogenated under conditions well known in the art to provide the piperidine of structure (8). For example, the 1,2,3,6-tetrahydropyridine (7) is dissolved in a suitable organic solvent, such as absolute ethanol, and treated with a suitable hydrogenation catalyst, such as 10% palladium on carbon. The reaction mixture is then treated with an excess of ammonium formate and the reaction is heated at reflux for about 2 to 4 hours. The reaction mixture is then cooled, filtered to remove the catalyst and the filtrate is concentrated under vacuum to provide piperidine (8). The piperidine (8) can be purified by flash chromatography on silica gel with a suitable eluent, such as ethyl acetate/hexane. Alternatively, the residue can be converted to a pharmaceutically acceptable salt, such as the oxalate salt by dissolving the residue in methanol, treating with 1 equivalent of oxalic acid and then concentrating the solution under vacuum. The solid can then be purified by recrystallization from a suitable organic solvent, such as diethyl ether to provide the purified oxalate salt of piperidine (8).

Compounds of structure (8a) can be prepared as disclosed in Scheme Ia in a manner analogous to the procedures disclosed for Scheme I above.

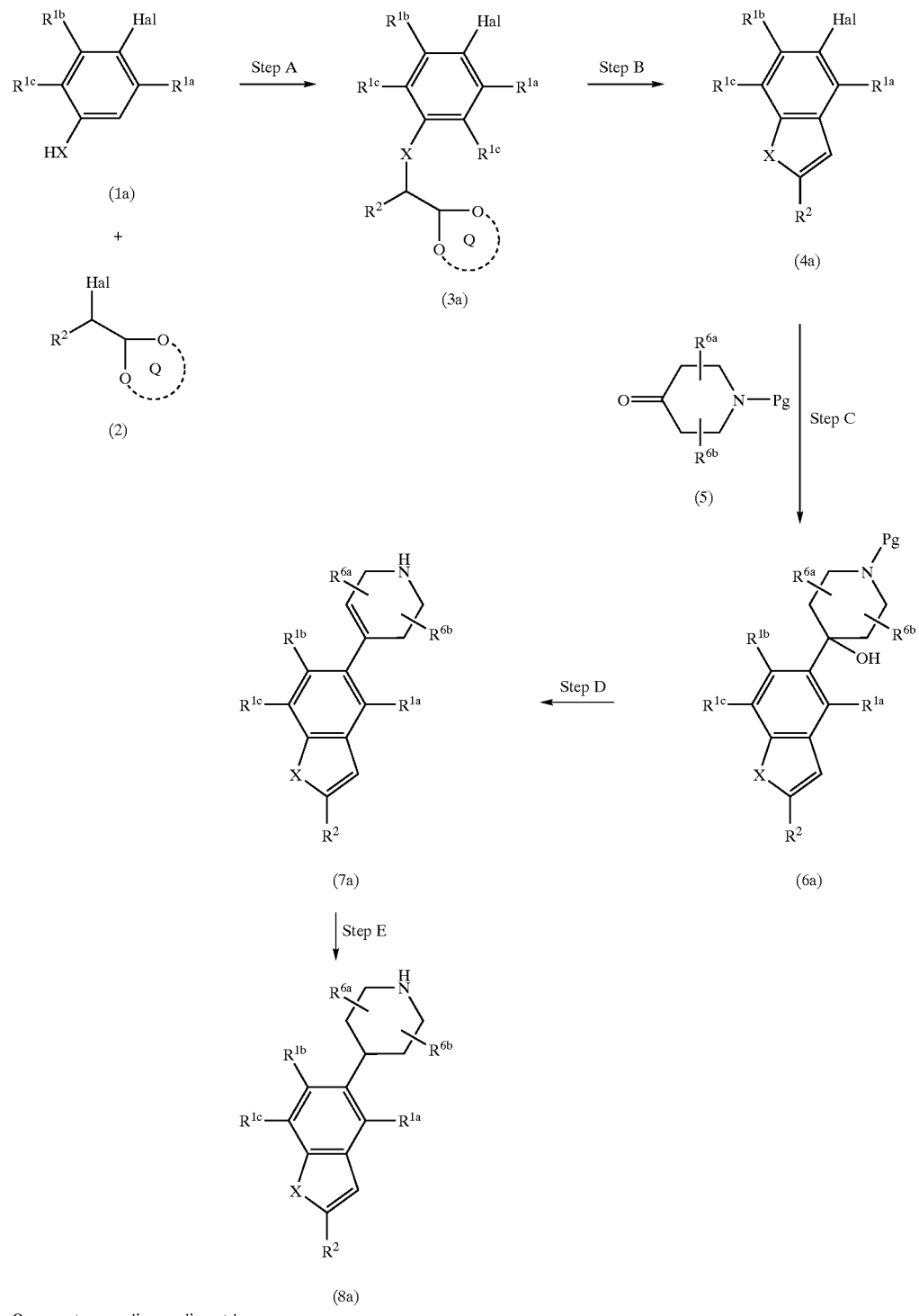
Scheme Ia
Q represents an acyclic or cyclic acetal
Pg represents a protecting group Scheme II provides an alternative synthesis of compound (7).

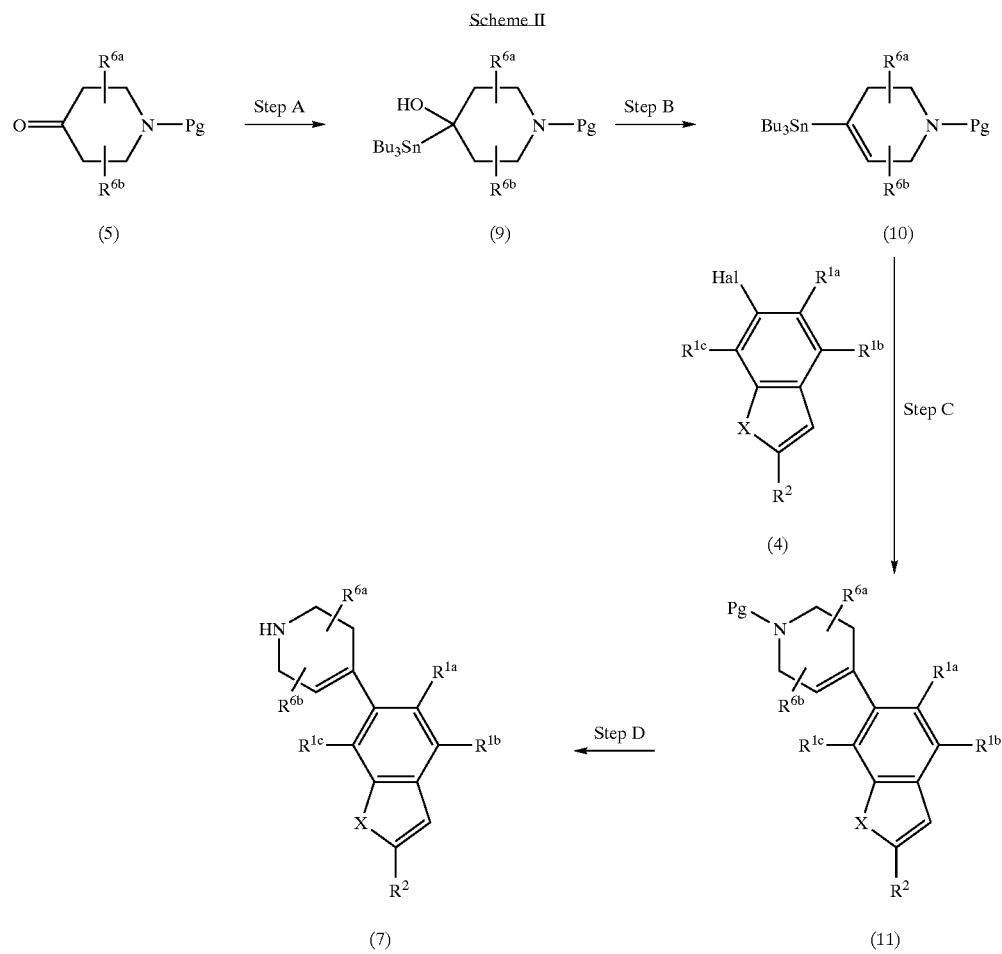

Scheme II

In Scheme II, step A, protected piperidone (5) is converted to the tin derivative (9) under conditions well known in the art. For example, diisopropylamine is dissolved in a suitable organic solvent, such as tetrahydrofuran and the solution is cooled to about 0° C. An equivalent of n-butyllithium is added and the reaction is stirred for about 15 minutes to one hour. Then one equivalent of tri-n-butyltinhydride is added dropwise to the solution, the reaction mixture is stirred for about one hour and then cooled to about −78° C. To this reaction mixture is added dropwise about 0.85 equivalents of the protected piperidone (5) dissolved in tetrahydrofuran. The reaction is then stirred for about 1 to 5 hours at −78° C. and then quenched with buffer (pH 6). The reaction mixture is extracted with a suitable organic solvent, such as ethyl acetate, the organic extracts are combined, dried over anhydrous sodium sulfate, filtered and concentrated under vacuum. The residue is purified by flash chromatography on silica gel with a suitable eluent, such as ethyl acetate/hexane to provide the tin derivative (9).

In Scheme II, step B, tin derivative (9) is dehydrated to the 1,2,3,6-tetrahydropyridine (10) under standard conditions. For example, the tin derivative (9) is dissolved in a suitable organic solvent, such as methylene chloride and the solution is cooled to about 0° C. An excess of triethylamine and about 2.0 equivalents of methanesulfonyl chloride are added to the solution which is allowed to stir for about 4 to 20 hours. The reaction mixture is warmed to room temperature and concentrated under vacuum. The residue is purified by flash chromatography on silica gel with a suitable eluent, such as ethyl acetate/hexane to provide the 1,2,3,6-tetrahydropyridine (10).

In Scheme II, step C the 1,2,3,6-tetrahydropyridine (10) is coupled with compound (4), prepared in Scheme I, to provide the compound of structure (11). For example, one equivalent of compound (4) and one equivalent of 1,2,3,6-tetrahydropyridine (10) are combined in a suitable organic solvent, such as toluene. A catalytic amount of 2,6-di-tert-butyl-4-methylphenol and a catalytic amount of tetrakis(triphenylphosphine)palladium(0) are added and the reaction mixture is heated at reflux for about 15 to 20 hours. The reaction mixture is then cooled, concentrated under vacuum and the residue purified by flash chromatography on silica gel with a suitable eluent, such as ethyl acetate/hexane to provide compound (11).

In Scheme II, step D, compound (11) is deprotected under conditions well known in the art to provide the compound of structure (7). For example, compound (11) is dissolved in a suitable organic solvent, such as toluene and treated with a suitable acid, such a p-toluenesulfonic acid. The reaction is heated at reflux for about 1 to 2 hours, then cooled to room temperature. The mixture is diluted with a suitable organic solvent, such as ethyl acetate, washed with sodium hydroxide solution, the organic layer is dried over anhydrous sodium sulfate, filtered and concentrated to provide compound (7).

Compounds of structure (7a) can be prepared as disclosed in Scheme IIa in a manner analogous to the procedures disclosed for Scheme II above.

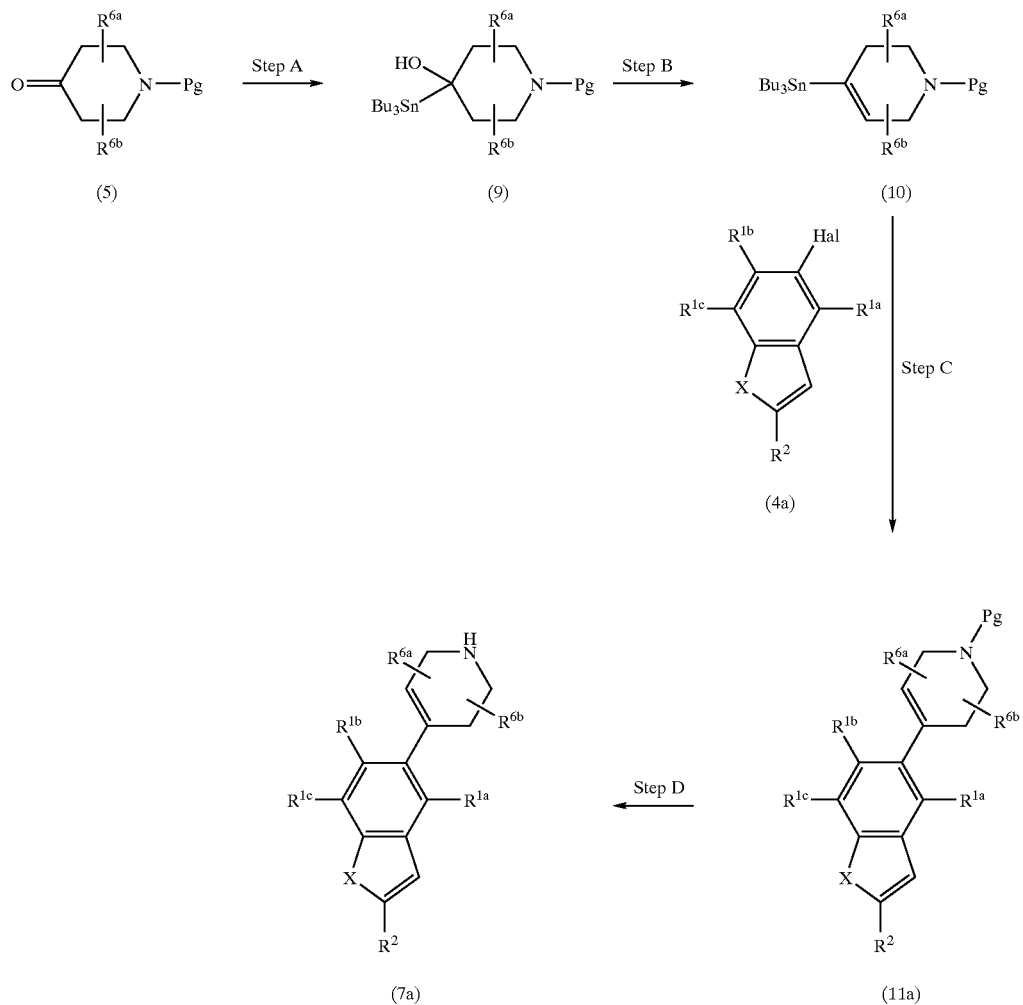

Compounds of structure (7b) can be prepared as disclosed in Scheme IIb in a manner analogous to the procedures disclosed for Scheme II above.

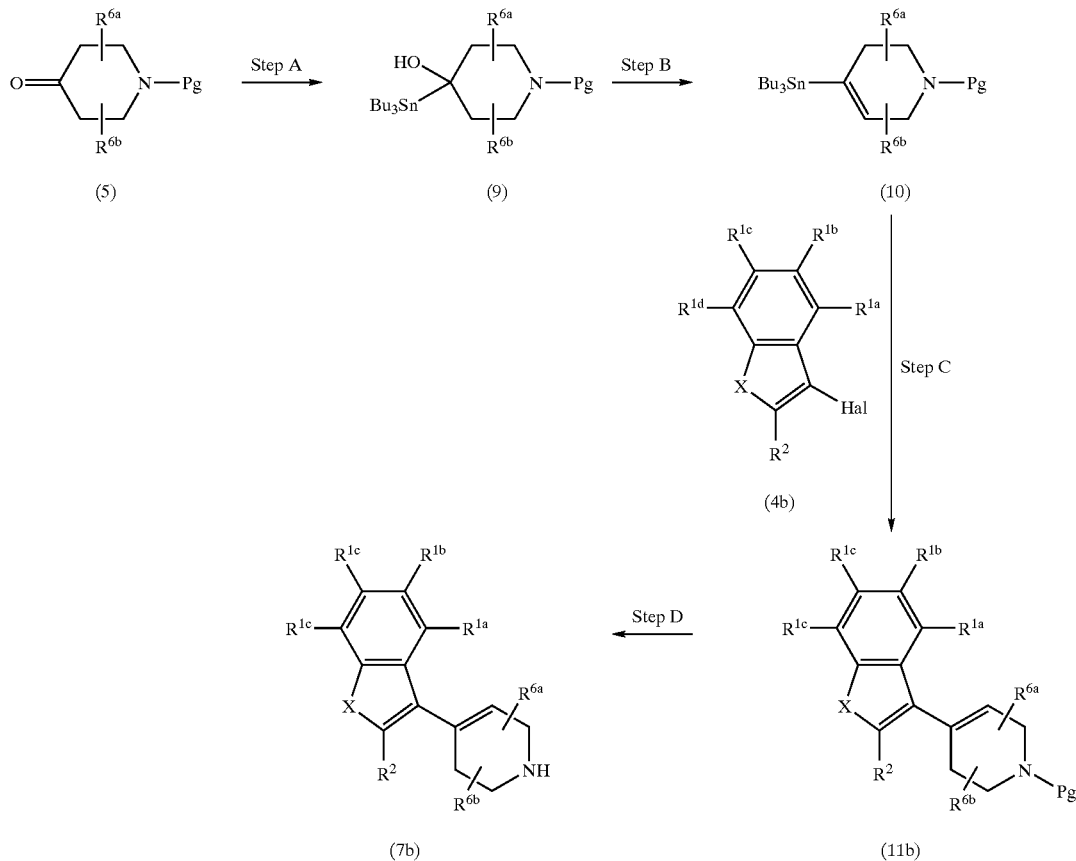

Scheme III provides a synthesis of the aldehydes of structure (17).

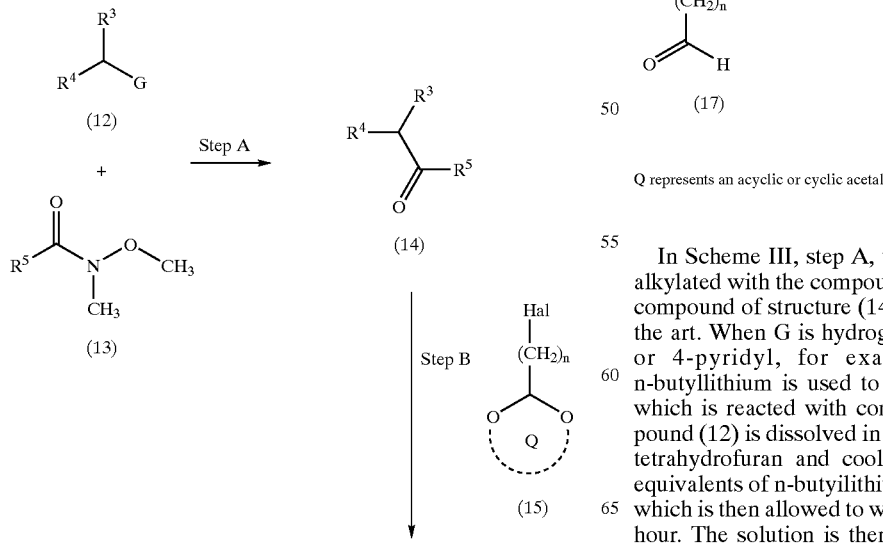

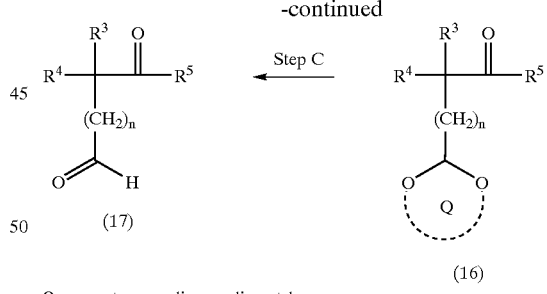

Q represents an acyclic or cyclic acetal

In Scheme III, step A, the compound of structure (12) is alkylated with the compound of structure (13) to provide the compound of structure (14) under conditions well known in the art. When G is hydrogen and $R_4$ is 2-pyridyl, 3-pyridyl or 4-pyridyl, for example, then a base, such as n-butyllithium is used to prepare the corresponding anion which is reacted with compound (13). For example, compound (12) is dissolved in a suitable organic solvent, such as tetrahydrofuran and cooled to about −78° C. About 1.1 equivalents of n-butyllithium is added to the cooled solution which is then allowed to warm to room temperature over one hour. The solution is then re-cooled to about −78° C. and treated dropwise with about 1.05 equivalents of a compound of structure (13) dissolved in tetrahydrofuran. [Compounds of structure 13 are readily prepared by one of ordinary skill in the art following generally the procedure disclosed by Brornidge. S. M., et al. *Synthetic Communications*, 23(4), 487–494 (1993).] The reaction is then allowed to warm to room temperature and stirred for about 20 to 40 hours. The reaction mixture is then diluted with water and dilute acid maintaining a pH of about 12. The quenched reaction is then extracted with a suitable organic solvent, such as methylene chloride, the organic extracts are combined, dried over anhydrous sodium sulfate, filtered and concentrated under vacuum. The residue is then purified by flash chromatography on silica gel with a suitable eluent, such as ethyl acetate/hexane to provide the compound (14).

Alternatively, when G is Cl or Br and $R_4$ is aryl, for example, a Grignard reagent is prepared, using techniques and procedures well known in the art, from magnesium in a suitable organic solvent, such as diethyl ether or tetrahydrofuran and refluxing as necessary. The resulting Grignard reagent is then combined with the compound (13) to provide compound (14).

In Scheme III, step B, compound (14) is alkylated with a compound of structure (15) to provide the compound of structure (16) under conditions well known in the art. For purposes of Scheme III, Hal represents Cl, Br or I. For example, compound (14) is dissolved in a suitable organic solvent and treated with a suitable base. Examples of suitable organic solvents are tetrahydrofuran, methyl sulfoxide, dimethylformamide, methyl sulfoxide/tetrahydrofuran, dimethylformamide/tetrahydrofuran, and the like. Examples of suitable bases are potassium tert-butoxide, n-butyllithium, sodium hydride, and the like. For example, compound (14) is dissolved in tetrahydrofuran, and the solution is added dropwise to a cooled suspension (0° C.) of 1.4 equivalents of sodium hydride in tetrahydrofuran. The reaction is warmed to room temperature and stirred for about 2 to 4 hours. Then about 1.5 equivalents of a compound (15) is added to the reaction which is then heated at reflux for about 16 hours. The reaction is then diluted with water, extracted with a suitable eluent, such as diethyl ether, the organic extracts are combined, dried over anhydrous sodium sulfate, filtered and concentrated under vacuum. The residue is purified by flash chromatography on silica gel with a suitable eluent, such as ethyl acetate/hexane to provide compound (16).

In Scheme III, step C, compound (16) is hydrolyzed under conditions well known in the art to provide the aldehyde of structure (17). For example, compound (16) is dissolved in a suitable organic solvent, such as acetone and treated with an excess of a suitable acid, such as 3N HCl. The reaction is stirred at room temperature for about 10 to 20 hours. It is then neutralized with a suitable base, such as 1 N sodium hydroxide. The neutralized mixture is then extracted with a suitable organic solvent, such as ethyl acetate, the organic extracts are combined, dried over anhydrous sodium sulfate, filtered and concentrated under vacuum to provide the aldehyde (17).

Scheme IV provides a synthesis of compounds of formulas Ia through Id. All substituents, unless otherwise specified, are previously defined. The reagents and starting materials are readily available to one of ordinary skill in the art.

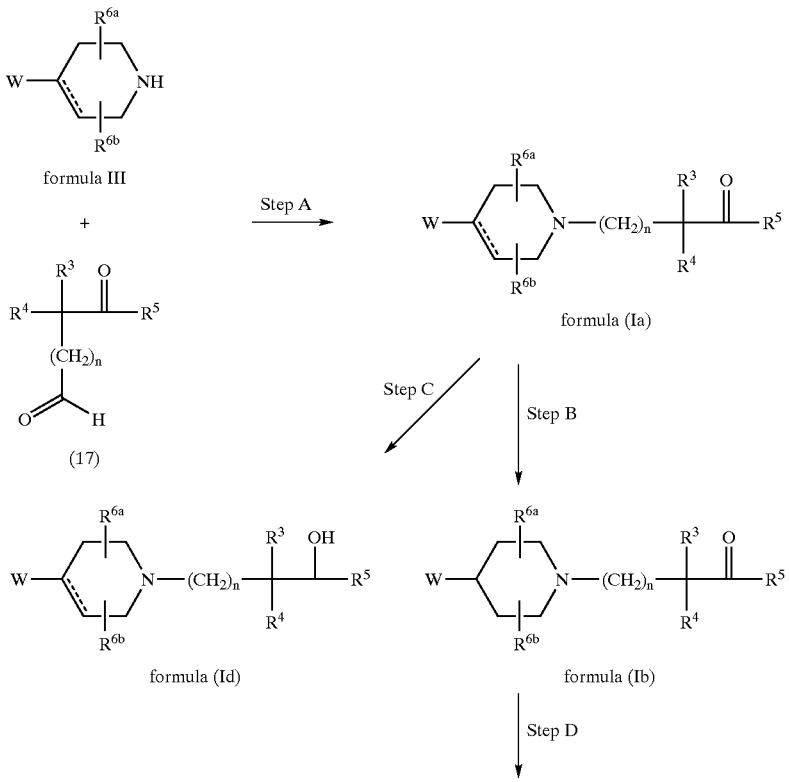

Scheme IV

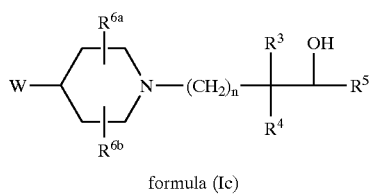

formula (Ic)

In Scheme IV, step A, compounds of formula III [for example see compounds (7), (7a), (7b), (8), (8a), and (31) all of which fall within the general scope of formula II] are subjected to a reductive alkylation with compound (17), prepared in Scheme III above, under conditions well known in the art, such as those disclosed in J. March, "Advanced Organic Chemistry: Reactions, Mechanisms and Structure", $2^{nd}$ Edition, McGraw-Hill, 1978, 819–820, to provide the compound of formula (Ia). For example, in Scheme IV, step A, about one equivalent of compound of formula III is combined with one equivalent of compound (17) in a suitable organic solvent, such as methylene chloride. To this solution is added about 2.5 equivalents of acetic acid and about 1.3 equivalents of sodium triacetoxyborohydride. The reaction is stirred at room temperature for about 4 to 24 hours and then made basic with 1N sodium hydroxide. The mixture is then extracted with a suitable organic solvent, such as methylene chloride, the combined organic extracts are dried over anhydrous sodium sulfate, filtered and concentrated under vacuum to provide the crude compound of formula Ia. This material can be purified by techniques well known in the art. For example, the crude material is purified by flash chromatography on silica gel with a suitable eluent such as ethyl acetate/hexane. The purified compound of formula Ia can then be converted to the pharmaceutically acceptable salt, such as the oxalate salt by dissolving in methanol and treating with one equivalent of oxalic acid. The solvent is then removed under vacuum to provide the oxalate salt of formula Ia. The oxalate salt can be further purified by recrystallization from suitable organic solvents, such as methylene chloride and hexane.

Alternatively, the crude compound of formula Ia can be purified by direct conversion of the crude free base to the pharmaceutically acceptable salt, such as the oxalate salt, and recrystallized from a suitable organic solvent, such as methylene chloride and hexane.

In Scheme IV, step B, formula Ia is hydrogenated under conditions well known in the art to provide the compound of formula Ib. For example, compound of formula Ia is dissolved in absolute ethanol and treated with 10% palladium on carbon. The reaction is stirred under an atmosphere of hydrogen for about 1 to 24 hours. The reaction is then filtered to remove the catalyst and the filtrate is concentrated under vacuum. The residue is purified by techniques well known in the art, such as those described in step A above to provide the compound of formula Ib as either the free base or a pharmaceutically acceptable salt.

In Scheme IV, step D, formula Ib is further reduced under conditions well known in the art to provide the compound of formula Ic. For example, the compound of formula Ib is dissolved in a suitable organic solvent such as methylene chloride, cooled to about −78° C. and treated with a suitable reducing agent, such as about 3 equivalents of diisobutylaluminum hydride or lithium aluminum hydride. The reaction is then slowly warmed to room temperature over about 2 hours and then stirred at room temperature for about 16 hours. The reaction is then diluted with saturated aqueous potassium sodium tartrate solution and extracted with methylene chloride. The organic extracts are combined, dried over anhydrous sodium sulfate, filtered and concentrated under vacuum. The residue is purified by flash chromatography on silica gel with a suitable eluent, such as ethyl acetate/hexane to provide the free base of the compound of formula Ic. As described above in step A, this free base can then be converted to the pharmaceutically acceptable salt, such as an oxalate salt.

In Scheme IV, step C the compound of formula Ia is reduced to the compound of formula Id in a manner analogous to the procedure described above in step D. In addition, the free base of formula Id is converted to the pharmaceutically acceptable salt in a manner analogous to the procedure described in step A above.

Scheme V provides a synthesis of the compound of formula Ie. Reagents and starting materials are readily available to one of ordinary skill in the art. All substituents are previously defined, unless otherwise indicated.

Scheme V

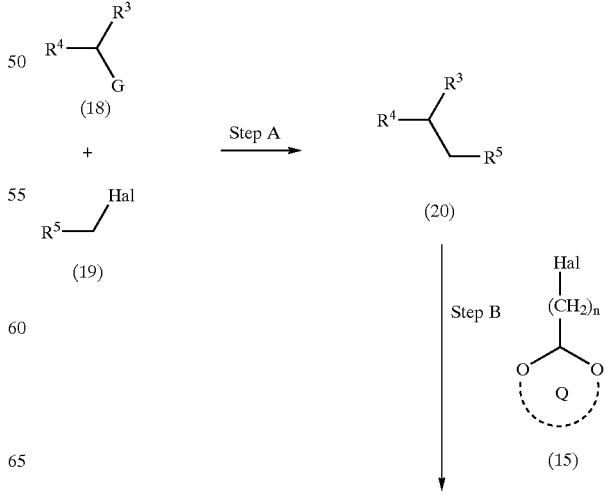

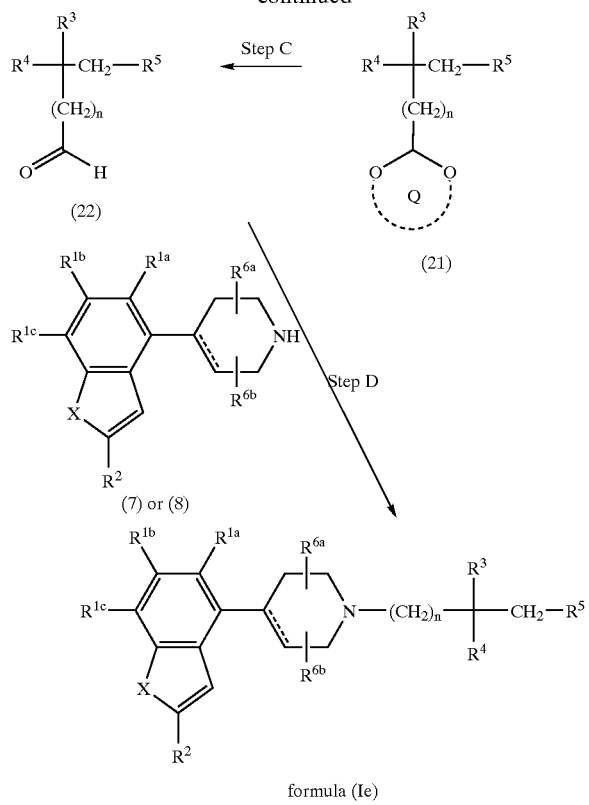

formula (Ie)

In Scheme V, step A, a compound of structure (18) is alkylated with a compound of structure (19) under conditions well known in the art to provide the compound of structure (20). When G is hydrogen and $R_4$ is 2-pyridyl, 3-pyridyl or 4-pyridyl, for example, then a base, such as n-butyllithium is used to prepare the corresponding anion which is reacted with compound (19). For example, compound (18) is dissolved in a suitable organic solvent such as THF and treated with a suitable base, such as n-butyllithium at about −78° C. The mixture is warmed to room temperature and then cooled back down to −78° C. and treated with about 1.05 equivalents of a compound (19), wherein for the purposes of Scheme V, Hal represents Cl, Br or I. The reaction is warmed to room temperature and allowed to stir for 10 to 20 hours. It can then be heated to reflux for about 2 to 24 hours and then cooled to room temperature. The solvent is then removed under vacuum, the residue dissolved in a suitable organic solvent, such as ethyl acetate, followed by addition of water. The layers are separated, and the aqueous is extracted with ethyl acetate. The organic extracts are combined, dried over anhydrous magnesium sulfate, filtered and concentrated under vacuum. The residue is purified by flash chromatography on silica gel with a suitable eluent, such as ethyl acetate/hexane to provide compound (20).

Alternatively, when G is Cl or Br and $R_4$ is aryl, for example, a Grignard reagent is prepared, using techniques and procedures well known in the art, from magnesium in a suitable organic solvent, such as diethyl ether or tetrahydrofuran and refluxing as necessary. The resulting Grignard reagent is then combined with the compound (19) under standard conditions to provide compound (20). Additional conditions for coupling of alkyl halides with organometallic reagents, can be found in J. March, "Advanced Organic Chemistry: Reactions, Mechanisms and Structure", 2nd Edition, McGraw-Hill, 1978, pages 409–412.

In Scheme V, step B, compound (20) is alkylated with compound (15) in a manner analogous to the procedure described in Scheme III, step B to provide the compound of structure (21). As used herein, Hal represents Cl, Br or I only.

In Scheme V, step C, compound (21) is hydrolyzed under acidic conditions in a manner analogous to the procedure described in Scheme III, step C to provide the aldehyde of structure (22).

In Scheme V, step D, compound (22) is used to reductively alkylate with compound (7) [prepared in Scheme I or II above] or compound (8) [prepared in Scheme I above], in a manner analogous to the procedure described in Scheme IV, step A to provide the compound of formula Ie.

Compounds wherein X is S(=O) or S(=O)$_2$ in formula I are readily prepared by one of ordinary skill in the art using well known techniques and procedures. For example, compounds of formulas Ia–Ie wherein X is S can be oxidized under standard conditions, such as treatment with m-chloroperbenzoic acid, to provide the corresponding sulfone [S(=O)$_2$] or sulfoxide [S(=O)].

Intermediate aldehyde of structure (17a) can be prepared as described in Scheme VI below. Aldehyde (17a) is reductively aminated in a manner analogous to aldehyde (17) to provide compound of formula I. The reagents and starting materials are readily available to one of ordinary skill in the art.

Scheme VI

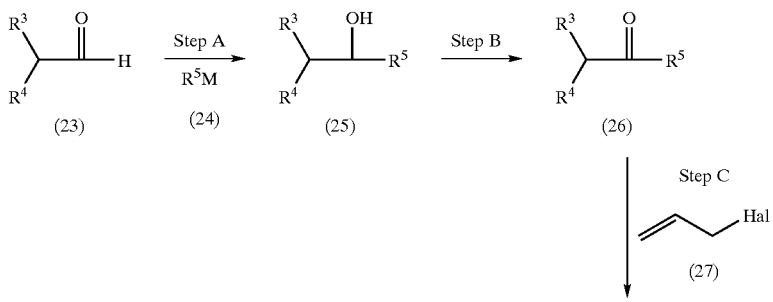

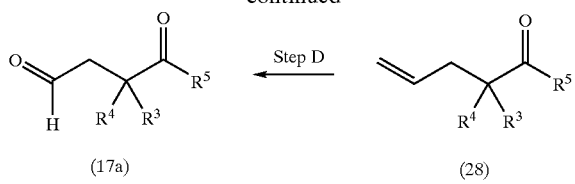

(17a) (28)

In Scheme VI, step A, aldehyde (23) is combined with a suitable organometallic reagent (24) under conditions well known in the art to provide alcohol (25). Examples of suitable organometallic reagents include Grignard Reagents, alkyl lithium reagents, and the like. Grignard Reagents are preferred. For examples of typical Grignard Reagents and reaction conditions, see J. March, "Advanced Organic Chemistry: Reactions, Mechanisms, and Structure", 2nd Edition, McGraw-Hill, pages 836–841 (1977). More specifically, aldehyde (23) is dissolved in a suitable organic solvent, such as tetrahydrofuran, cooled to about −5° C. and treated with about 1.1 to 1.2 equivalents of a Grignard reagent of formula (24) wherein M is MgCl or MgBr The reaction is allowed to stir for about 1 to 2 hours, then quenched, and alcohol (25) is isolated. For example, the reaction mixture is poured onto ice-cold 1N HCl, the quenched mixture is extracted with a suitable organic solvent, such as toluene, the organic extracts are dried over anhydrous magnesium sulfate, filtered and concentrated under vacuum to provide alcohol (25).

In Scheme VI, step B, alcohol (25) is oxidized under standard conditions well know in the art, such as those described by J. March, "Advanced Organic Chemistry: Reactions, Mechanisms, and Structure", 2nd Edition, McGraw-Hill, pages 1082–1084 (1977), to provide ketone (26).

For example, alcohol (25) is dissolved in a suitable organic solvent, such as methylene chloride, the solution cooled with a wet ice-acetone bath, and treated with 2.5 to 3.0 equivalents of dimethyl sulfoxide. After stirring for about 30 minutes, the reaction is then treated with about 1.8 equivalents of $P_2O_5$. The reaction is allowed to stir for about 3 hours and then is treated over about 30 minutes with about 3.5 equivalents of a suitable amine, such as triethylamine.

The cooling bath is then removed and the reaction is allowed to stir for about 8 to 16 hours. The ketone (26) is then isolated by standard extraction techniques well known in the art.

In Scheme VI, step C, ketone (26) is treated with a suitable base followed by addition of the alkene (27), wherein X is a suitable leaving group, to provide compound (28). For example, ketone (26) is combined with an excess of alkene (27) in a suitable organic solvent, such as tetrahydrofuran, and cooled with a wet ice acetone bath. Examples of suitable leaving groups are Cl, Br, I, and the like. Preferred leaving groups are Cl and Br. About 1.1 equivalents of a suitable base, such as potassium tert-butoxide, is added and the reaction is allowed to stir for about 2 hours at room temperature. The reaction is then quenched with aqueous acid and compound (28) is isolated by extraction with heptane. The heptane extracts are washed with sodium bicarbonate, dried over anhydrous magnesium sulfate, filtered and concentrated under vacuum to provide compound (28).

In Scheme VI, step D, compound (28) is treated with a suitable oxidizing agent to provide aldehyde (17a). Ozone is the preferred oxidizing agent. Examples of suitable oxidizing reagents and conditions are described by J. March, "Advanced Organic Chemistry: Reactions, Mechanisms, and Structure", 2nd Edition, McGraw-Hill, pages 1090–1096 (1977).

For example, compound (28) is dissolved in a suitable organic solvent, such as methanol, a small amount of Sudan III is added, and the solution is cooled to about −20° C. Ozone is bubbled into the solution for about 4 hours until the pink color turns to a pale yellow color. Then $Me_2S$ is added to the reaction mixture and the cooling bath is removed. Concentration of the reaction mixture under vacuum provides the intermediate dimethyl acetal of aldehyde (17a). This dimethyl acetal is readily hydrolyzed under standard acidic conditions to provide aldehyde (17a). Alternatively, direct acidic work-up of the crude reaction mixture provides aldehyde (17a).

Compounds of structure (31) can be prepared as disclosed below in Scheme VII. Reagents and starting materials are readily available to one of ordinary skill in the art. Unless otherwise specified, substituents are as previously defined.

Scheme VII

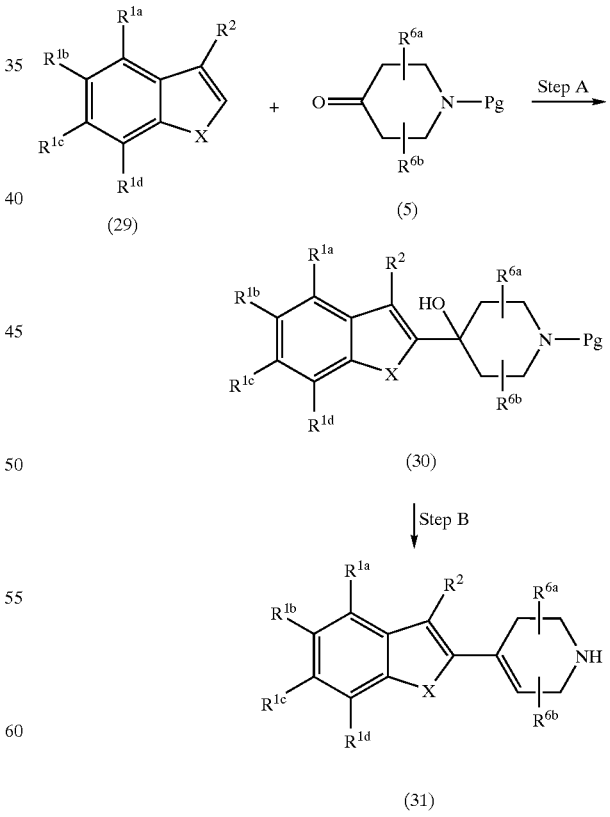

In Scheme VII, step A the compound of structure (29) is coupled with compound (5) under conditions well known in the art to provide compound of structure (30). For example, compound (29) is dissolved in a suitable organic solvent, such as tetrahydrofuran and cooled to about −78° C. The cooled solution is then treated with about 1.05 equivalents of a suitable base, such as n-butyllithium and the solution is allowed to stir for about 15 minutes to one hour. To this reaction mixture is then added one equivalent of compound (5). The reaction mixture is then warmed to room temperature and allowed to stir for about 10 to 20 hours. The product (30) is then isolated by techniques well known in the art, such as extraction. For example, the reaction is quenched with water and extracted with a suitable organic solvent, such as ethyl acetate. The combined organic extracts are washed with 1 N NaOH, water, brine, dried over anhydrous sodium sulfate, filtered and concentrated under vacuum to provide product (30).

In Scheme VII, step B, compound (30) is then concomitantly deprotected and dehydrated to provide the compound of structure (31). For example, compound (30) is dissolved in a suitable organic solvent, such as toluene and treated with about 2 equivalents of a suitable acid, such as p-toluenesulfonic acid. The reaction mixture is then heated at reflux for about 1 hour and then cooled to room temperature. The reaction mixture is then concentrated under vacuum. The residue is dissolved in a suitable organic solvent, such as ethyl acetate which is then washed with 1 N NaOH, water, brine, dried over anhydrous sodium sulfate, filtered and concentrated under vacuum to provide the compound of structure (31).

The following examples illustrate the invention and represent typical syntheses of the compounds of formula I as described generally above. The reagents and starting materials are readily available to one of ordinary skill in the art. As used herein, the following terms have the meanings indicated: "eq" refers to equivalents, "g" refers to grams; "mg" refers to milligrams; "L" refers to liters; "mL" refers to milliliters; "µL" refers to microliters; "mol" refers to moles; "mmol" refers to millimoles; "psi" refers to pounds per square inch; "min" refers to minutes; "h" refers to hours, "° C." refers to degrees Celsius; "TLC" refers to thin layer chromatography, "HPLC" refers to high performance liquid chromatography; "$R_f$" refers to retention factor; "$R_t$" refers to retention time; "δ" refers to part per million down-field from tetramethylsilane "THF" refers to tetrahydrofuran; "DMF" refers to N,N-dimethylformamide; "DMSO" refers to methyl sulfoxide; "LDA" refers to lithium diisopropylamide; "aq" refers to aqueous; "iPrOAc" refers to isopropyl acetate; "EtOAc" refers to ethyl acetate; "EtOH" refers to ethyl alcohol; "MeOH" refers to methanol; "MTBE" refers to tert-butyl methyl ether; "TMEDA" refers to N,N,N',N'-tetramethylethylenediamine, "PPA" refers to polyphosphoric acid; "PTSA" refers to p-toluenesulfonic acid; and "RT" refers to room temperature.

Preparation 1

Preparation of N-Benzyl-3,3-dimethyl-4-piperidone.

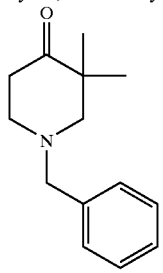

In a 1 liter 3-necked flask equipped with mechanical stirring, addition funnel and a calcium chloride drying tube is added a 37% weight solution of formaldehyde (168.5 mL, 2.25 mole) dissolved in 500 mL of absolute ethanol. The resulting solution was cooled in an ice-water bath to 10° C., and benzylamine (109 mL, 1 mole) was added dropwise over a one hour period. In a separate 3 liter 3-necked flask equipped with mechanical stirring, addition funnel and two condensers is added 3-methyl-2-butanone (113 mL, 1.06 mole) dissolved in 500 mL of absolute ethanol and concentrated hydrogen chloride (92 mL, 1.11 mole). The resulting solution is brought to reflux and the formaldehyde/benzylamine solution is added dropwise over a 2 hour period. This solution is refluxed overnight, and then cooled to ambient temperature. Diisbpropylethylamine (142.2 g, 1.1 mole) and formaldehyde (22.46 mL, 0.3 mole) are added and the resulting solution is heated to reflux for six hours, and then cooled to ambient temperature. The solution was quenched with potassium hydroxide (61.6 g, 1.1 mole) in 200 mL of water, and then extracted with 500 mL ethyl acetate three times. The organics were concentrated under vacuum to give 225 g of red oil. The crude oil was dissolved in 1 liter of methylene chloride. This solution was carefully poured over 1 kg of silica gel on a sintered glass filter. The silica gel was washed with 4 L of methylene chloride. The methylene chloride was concentrated under vacuum to provide 142 g of a yellow oil which crystallizes in the freezer overnight. Yield=65.4%.

MS (ion spray)=218.3 (M+1).

Preparation 2

Preparation of 1-cyclohexyl-3-(2-(1,3-diethylacetal))-2-(2-pyridyl)propan-1-one.

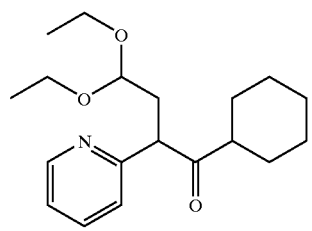

Scheme III, step B: Potassium t-butoxide (662.4 g, 5.90 moles) and 5982 mL of THF were charged into a 22 L 3-necked flask equipped with an overhead air stirrer and shaft, nitrogen inlet and a large addition funnel while purging with nitrogen. The reaction mixture was cooled to −5° C. and a solution of 1-cyclohexyl-2-(2-pyridyl)ethan-1-one (800 g, 3.94 moles) in 1445 mL of THF was added from the addition funnel to the cold reaction mixture over 50 minutes while maintaining the pot temperature below 15° C. The resulting mixture was stirred for ~20 minutes at 5°–10° C. The reaction mixture was allowed to warm to room temperature and stirred at that temperature for 2 hours before it was cooled ~10° C.

During the 2 hour stir the addition tunnel was charged with a solution of the bromoacetaldehyde diethyl acetal (888 mL, 5.90 moles) in DMSO (4336 mL). The solution was added dropwise (over 30 minutes) to the cold reaction mixture above. The cooling bath was replaced by a heating mantle. The reaction mixture was heated under nitrogen to a gentle reflux then allowed to reflux overnight.

The reaction mixture was cooled to 15° C. with a water bath. Approximately half of the reaction mixture was transferred to a to a 22 L bottom outlet flask and quenched with 3 L of ice cold water. The resulting mixture was extracted with 3 L of diethyl ether and the aqueous layer extracted with another 2 L of diethyl ether. The other half of the reaction mixture was treated as the first. The ether extracts were all combined then washed with 3, 1 L volume of water followed by 5, 1.5 L volume of water. The resulting organic solution was dried over anhydrous Na₂SO₄, filtered, and concentrated in vacuo to 1237 g of intermediate title compound as a dark red-brown oil.

EXAMPLE 1

Preparation of 4-(6-benzo(b)thiophene-1,2,3,6-tetrahydropyridyl)-1-cyclohexyl-2-(2-pyridyl)butan-1-one.

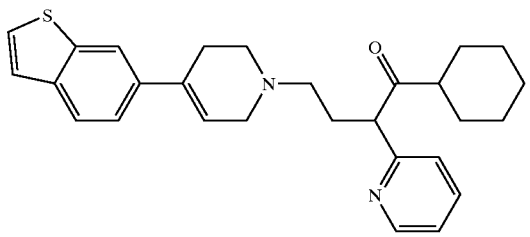

Preparation of Intermediates 1A and 1B.

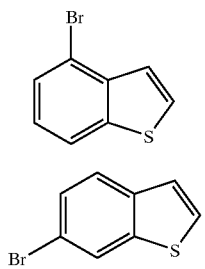

Scheme I, steps A and B: A mixture of 3-bromothiophenol (25 g, 132 mmol, 1 eq.), bromoacetaldehyde diethyl acetal (25.5 g, 129 mmol, 0.98 eq.) and K₂CO₃ (27 g, 198 mmol, 1.5 eq.) in 200 mL of DMF was stirred at room temperature for 24 hours. Water was added to the reaction mixture and the mixture was extracted with ethyl acetate 2 times. The combined organic layers were washed with 1 N NaOH, water, brine, dried with anhydrous Na₂SO₄, filtered, and concentrated under reduced pressure to provide 30 g of residue as an oil. 15 g of the residue was dissolved in dichloroethane (100 mL) and the solution was added dropwise into a boiling solution 35 g of PPA in 800 mL of dichloroethane. The reaction was kept at reflux for another hour. The solution was decanted from the residue and dichloroethane was added to the residue, stirred and decanted. The solution and the extracts were combined and concentrated under reduced pressure. The residue was dissolved in ethyl acetate and the solution was washed with 10% of Na₂CO₃ (aq.), water, brine, dried with anhydrous Na₂SO₄, filtered, and concentrated under reduced pressure. The residue was subjected to silica gel chromatography, eluting with hexane. The fractions containing product were combined and concentrated under reduced pressure to provide 9 g of intermediates 1A and 1B as an oil.

Preparation of Intermediate 1C:

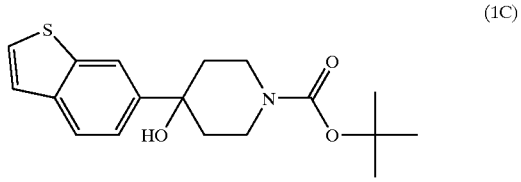

Scheme I, step C: To a solution of intermediates 1A and 1B (241 g, 113 mmol, 1 eq) and magnesium (5.5 g, 226 mmol, 2 eq.) in 100 mL ether was added BrCH₂CH₂Br (9.7 mL, 113 mmol, 1 eq.) dropwise over 30 minutes. After the addition, the reaction was headed at reflux gently for 2 hours. The reaction was allowed to cool down to room temperature and 1-(t-butoxycarbonyl)-4-piperidone (27 g, 136 mmol, 1.2 eq.) in 200 mL of THF was added into the solution. The reaction was stirred at room temperature overnight. Water was added to the mixture, and the mixture was extracted with ethyl acetate 3 times. The combined organic layer was washed with water, brine, dried with anhydrous Na₂SO₄, filtered, and concentrated under reduced pressure. The residue was subjected to silica gel chromatography, eluting with a mixture of ethyl acetate and hexane (EtOAc:Hexane=1:4). The fractions containing product were combined and concentrated under reduced pressure to provide 11 g of intermediate 1C.

Preparation of intermediate 1D.

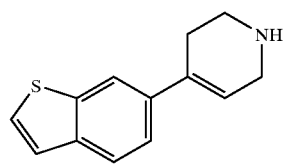

Scheme I, step D: Intermediate 1C (1.2 g, 3.6 mmol, 1 eq) was dissolved in 100 mL of toluene. PTSA (1.36 g, 7.2 mmol, 2 eq.) was added to the solution and the mixture was heated at reflux for 2 hours (with Dean Stark trap). The reaction was allowed to cool down to room temperature and concentrated under reduced pressure. The residue was dissolved in ethyl acetate and the solution was washed with 1N NaOH 4 times, water and brine, dried with anhydrous Na₂SO₄, filtered, and concentrated at reduced pressure to give 0.7 g of intermediate 1D as an oil.

Preparation of 1-cyclohexyl-2-(2-pyridyl)ethan-1-one.

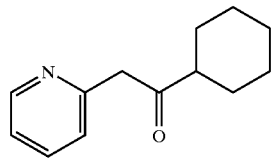

Scheme III, step A: A 100 mL round bottom flash was charged with 2-picoline (1.09 mL, 11.02 mmol) and anhydrous THF (15 mL). The solution was cooled to −78° C. and n-butyllithium (7.6 mL of a 1.6M solution in THF, 12.12 mmol) was added dropwise to the cooled solution. After addition was complete, the reaction mixture was warmed to room temperature over one hour and then cooled again to −78° C. N-methoxy-N-methyl cyclohexyl amide (2.0 g, 11.68 mmol) in THF (10 mL) was added dropwise to the reaction mixture. After addition was complete, the reaction was warmed to room temperature over one hour and then stirred for 40 hours. The reaction mixture was then treated with water and 1N HCl (keeping the pH at approximately 12). The reaction mixture was then extracted with methylene chloride (3×20 mL). The organic extracts were combined, dried over anhydrous sodium sulfate, filtered and concentrated under vacuum to provide an orange oil which was purified by flash chromatography (ethyl acetate:hexane, 3:7, silica gel) to provide 1-cyclohexyl-2-(2-pyridyl)ethan-1-one (2.06 g).

Preparation of 1-cyclohexyl-3-(2-(1,3-dioxolane))-2-(2-pyridyl)propan-1-one.

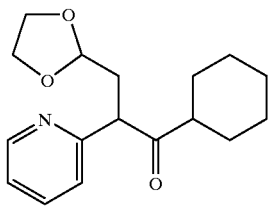

Scheme III, step B: A 250 mL round bottom flask was charged with anhydrous DMF (30 mL) and sodium hydride (0.56 g of a 60% dispersion, 14.0 mmol). The suspension was cooled to 0° C. and 1-cyclohexyl-2-(2-pyridyl)ethan-1-one (2.03 g, 10 mmol) in THF (30 mL) was added dropwise to the suspension. After addition was complete, the reaction was stirred for 2.5 hours at room temperature. Then 2-bromomethyl-1,3-dioxolane (1.55 mL, 15 mmol) was added and the reaction was heated at reflux for 16 hours. The reaction mixture was then quenched with water and extracted with diethyl ether (4×50 mL). The combined organic extracts were dried over anhydrous magnesium sulfate, filtered and concentrated under vacuum. The residue was purified by column chromatography (ethyl acetate:hexane, 3:7, silica gel) to provide 1-cyclohexyl-3-(2-(1,2-dioxolane))-2-(2-pyridyl)propan-1-one (1.79 g, 62%) as a yellow oil.

Preparation of 1-cyclohexyl-2-(2-pyridyl)butan-1-one-4-al.

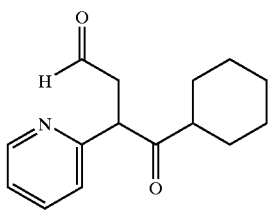

Scheme III, step C: 1-cyclohexyl-3-(2-(1,3-dioxolane))-2-(2-pyridyl)propan-1-one (0.40 g, 1.38 mmol, prepared above) was dissolved in acetone (10 mL), treated with 3N HCl (10 mL) and stirred for 16 hours at room temperature. The reaction mixture was basified with 1 N sodium hydroxide (pH=8–9) and extracted with ethyl acetate. The organic extracts were dried over anhydrous sodium sulfate, filtered and concentrated under vacuum to provide crude 1-cyclohexyl-2-(2-pyridyl)butan-1-one-4-al which was carried on to the next step without further purification.

Preparation of the Final Title Compound.

Scheme IV, step A: To a solution of intermediate 1D (400 mg, 1.85 mmol, 1 eq.) and 1-cyclohexyl-2-(2-pyridyl)butan-1-one-4-al (800 mg, 3.26 mmol, 1.76 eq.) in 20 mL methylene chloride, was added acetic acid (0.4 mL, 6.96 mmol, 3.76 eq. followed by sodium triacetoxyborohydride (690.9 mg, 3.26 mmol, 1.76 eq.). The reaction was stirred at room temperature for 3 hours. NaOH (aq. 1 N) was added and the mixture was extracted with ethyl acetate 3 times. The combined organic extracts were dried with anhydrous Na$_2$SO$_4$, filtered, and concentrated under reduced pressure. The residue was subjected to silica gel chromatography, eluting with ethyl acetate. The fractions containing product were combined and concentrated under reduced pressure to provide 529 mg of the final title compound. The final title compound was converted to its oxalate salt with 1 equivalent of oxalic acid; MS=445 (M+1); mp 164–169° C. (oxalate).

EXAMPLE 2

Preparation of 4-(6-benzo(b)thiophene-1,2,3,6-tetrahydropyridyl)-1-cyclohexyl-2-(2-pyridyl)butan-1-ol.

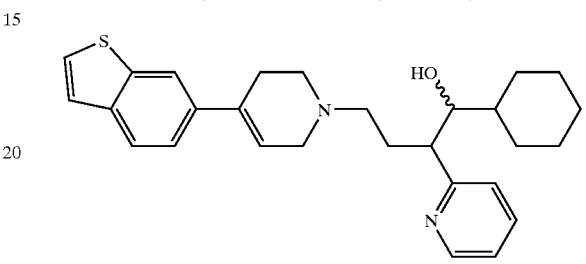

Scheme IV, step C: To a suspension of LiAlH$_4$ (71 mg, 1.87 mmol, 5 eq.) in 20 mL of diethyl ether, was added 4-(6-benzo(b)thiophene-1,2,3,6-tetrahydropyridyl)-1-cyclohexyl-2-(2-pyridyl)butan-1-one (200 mg, 0.374 mmol, 1 eq.) in portions at room temperature. 5 mL of THF was added after 1 hour. The reaction was allowed to stir at room temperature for 2 hours before it was quenched by addition of Na$_2$SO$_4$.10H$_2$O to the reaction mixture. The mixture was then filtered and the filtrate was concentrated under reduced pressure. The residue was subjected to silica gel chromatography, eluting with ethyl acetate. The fractions containing product were combined and concentrated under reduced pressure to provide 59.4 mg of title compound. The title compound was then converted to its oxalate salt with 1 equivalent of oxalic acid; (MS=447 (m+1); mp=94–98° C. (oxalate salt)).

EXAMPLE 3

Preparation of 4-(6-benzo(b)thiophene-1,2,3,6-tetrahydropyridyl)-1-cycloheptyl-2-(2-pyridyl)butan-1-one.

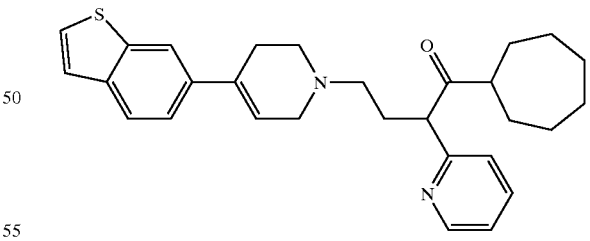

Preparation of N-methoxy-N-methyl cycloheptyl amide.

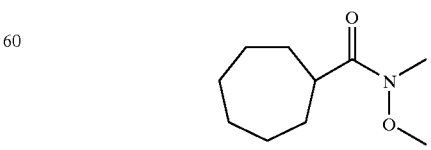

Cycloheptanecarboxylic acid (25.0 g, 0.176 mol) was dissolved in methylene chloride (100 mL) and oxalyl chloride (23 mL, 0.264 mol) was added dropwise to the solution. The reaction mixture was stirred for 30 minutes at room temperature and then concentrated under vacuum to provide the acid chloride of cycloheptanecarboxylic acid as a yellow oil.

N,O-dimethylhydroxylamine hydrochloride (18.03 g, 0.185 mol) was suspended in methylene chloride (200 mL) and treated with triethylamine (49.1 mL, 0.35 mol). The mixture was stirred for 15 minutes at room temperature and then cooled to 0° C. The above-formed acid chloride of cycloheptanecarboxylic acid dissolved in methylene chloride (30 mL) was added dropwise to the cooled solution. After addition was complete, the reaction mixture was warmed to room temperature and allowed to stir for 17 hours. The mixture was then poured into water (200 mL). The layers were separated, and the organic layer was dried over anhydrous sodium sulfate, filtered and concentrated to provide N-methoxy-N-methyl cycloheptyl amide.

Preparation of 1-cycloheptyl-2-(2-pyridyl)ethan-1-one.

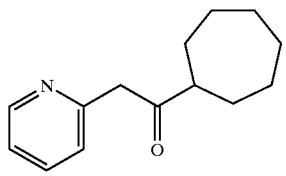

Scheme III, step A: A 100 mL round bottom flask was charged with 2-picoline (2.52 mL, 25.5 mmol) and anhydrous THF (30 mL). The solution was cooled to −78° C. and n-butyllithium (17.5 mL of a 1.6 M solution in THF, 28.05 mmol) was added dropwise to the solution. After addition was complete, the reaction was warmed slowly to room temperature over one hour and then cooled again to −78° C. N-methoxy-N-methyl cycloheptyl amide (5.0 g, 27.03 mmol, formed above) was added to the reaction. The reaction mixture was allowed to warm to room temperature with stirring overnight. The reaction was carefully quenched with water and extracted with ethyl acetate. The organic extracts were dried over anhydrous sodium sulfate, filtered and concentrated under vacuum. The residue was purified by flash chromatography (ethyl acetate:hexane, 3:7, silica gel) to provide 1-cycloheptyl-2-(2-pyridyl)ethan-1-one (5.03 g, 91%).

Preparation of 1-cycloheptyl-3-(2-(1,3-dioxolane))-2-(2-pyridyl)propan-1-one.

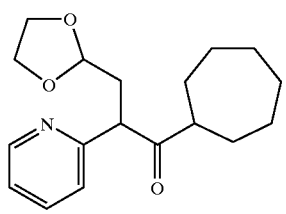

Scheme III, step B: 1-cycloheptyl-2-(2-pyridyl)ethan-1-one (5.0 g, 23.0 mmol, prepared above in Scheme III, step A) was dissolved in anhydrous THF (50 mL) was added dropwise to a suspension of sodium hydride (1.29 g of a 60% dispersion, 32.2 mmol) in anhydrous DMF cooled to 0° C. The reaction mixture was then warmed to room temperature and stirred for one hour. Then 2-bromomethyl-1,3-dioxolane (3.58 mL, 34.5 mmol) and potassium iodide (0.5 g, crushed) were added and the reaction mixture was heated at reflux for 16 hours. Water was added, and the mixture was extracted with ethyl acetate. The organic extracts were combined, dried over anhydrous sodium sulfate, filtered and concentrated under vacuum. The residue was purified by flash chromatography (ethyl acetate/hexane, 3/7, silica gel) to provide 1-cycloheptyl-3-(2-(1,3-dioxolane))-2-(2-pyridyl)propan-1-one (4.52 g, 65%).

Preparation of 1-cycloheptyl-2-(2-pyridylbutan-1-one-4-al.

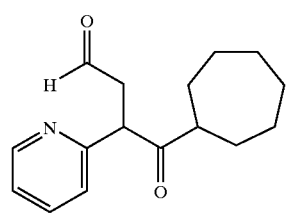

Scheme III, step C; 1-cycloheptyl-3-(2-(1,3-dioxolane))-2-(2-pyridyl)propan-1-one (0.51 g, 1.68 mmol) was dissolved in acetone (10 mL), treated with 3N HCl (10 mL) and stirred for 16 hours at room temperature. The reaction mixture was neutralized with 1N sodium hydroxide (30 mL) and extracted with ethyl acetate. The organic extracts were dried over anhydrous sodium sulfate, filtered and concentrated under vacuum to provide 1-cycloheptyl-2-(2-pyridyl)butan-1-one-4-al.

Preparation of Final Title Compound.

Scheme IV, step A: 1-cycloheptyl-2-(2-pyridyl)butan-1-one-4-al (0.31 g, 1.19 mmol, prepared in Scheme III, step C above) is combined with intermediate 1D (1.19 mmol, prepared in Example 1) in methylene chloride (10 mL) with acetic acid (0.17 mL, 2.98 mmol) and sodium triacetoxyborohydride (0.33 g, 1.55 mmol). The reaction mixture is stirred at room temperature for 5 hours. It is then made basic with 1N sodium hydroxide and extracted with methylene chloride. The combined organic extracts are dried over anhydrous sodium sulfate, filtered and concentrated under vacuum. The residue can be purified by flash chromatography (ethyl acetate:hexane, 1:1, silica gel) to provide the final title compound.

EXAMPLE 4

Preparation of 4-(6-benzo(b)thiophene-1,2,3,6-tetrahydropyridyl)-1-cyclopentyl-2-(2-pyridyl)butan-1-one

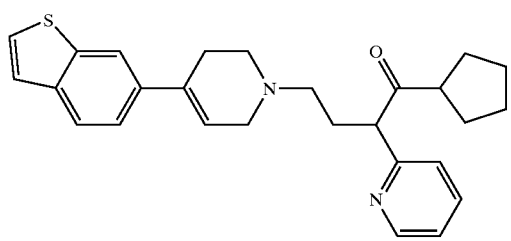

Preparation of 1-cyclopentyl-2-(2-pyridyl)ethan-1-one.

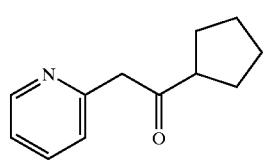

Scheme III, step A: A 100 mL round bottom flask was charged with 2-picoline (2.97 mL, 30.05 mmol) and anhydrous THF (30 mL). The solution was cooled to −78° C. and n-butyllithium (20.7 mL of a 1.6 M solution in THF, 33.1 mmol) was added dropwise. The reaction mixture was slowly warmed to room temperature and then stirred for one hour. The reaction mixture was then cooled back to −78° C. and N-methoxy-N-methyl-cyclopentyl amide (5.0 g, 31.85 mmol) was added. The reaction mixture was allowed to warm to room temperature overnight with stirring and then quenched with 0.1 N HCl to pH 9. The mixture was then extracted with methylene chloride, the organic extracts were combined, dried over anhydrous sodium sulfate, filtered and concentrated under vacuum. The residue was purified by flash chromatography (ethyl acetate:hexane, 3:7, silica gel) to provide 1-cyclopentyl-2-(2-pyridyl)ethan-1-one (4.35 g, 77%).

Preparation of 1-cyclopentyl-3-(2-(1,3-dioxolane))-2-(2-pyridyl)propan-1-one.

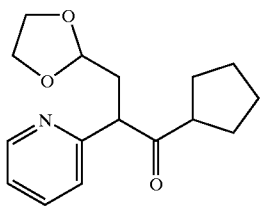

Scheme III, step B: A 500 round bottom flask was charged with 60% sodium hydride (1.27 g, 31.9 mmol) and anhydrous DMF (50 mL). The suspension was cooled to 0° C. and 1-cyclopentyl-2-(2-pyridyl)ethan-1-one (4.30 g, 22.8 mmol, prepared above in Scheme III, step A) dissolved in anhydrous THF (50 mL) was added dropwise to the suspension. The reaction mixture was warmed to room temperature and stirred for one hour. Then 2-bromomethyl-1,3-dioxolane (3.54 mL, 34.2 mmol) and potassium iodide (0.2 g, crushed) were added and the reaction mixture was heated at reflux for 6 hours. The reaction mixture was then cooled to room temperature and stirred for 16 hours. Water was added, and the mixture was extracted with ethyl acetate. The organic extracts were combined, dried over anhydrous sodium sulfate, filtered and concentrated under vacuum. The residue was purified by flash chromatography (ethyl acetate:hexane, 3:7, silica gel) to provide 1-cyclopentyl-3-(2-(1,3-dioxolane))-2-(2-pyridyl)propan-1-one (1.43 g).

Preparation of 1-cyclopentyl-2-(2-pyridyl)butan-1-one-4-al.

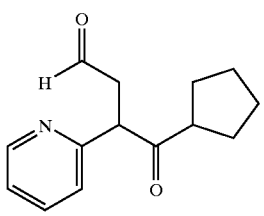

Scheme III, step C: 1-cyclopentyl-3-(2-(1,3-dioxolane))-2-(2-pyridyl)propan-1-one (0.48 g, 1.75 mmol, prepared above in Scheme III, step B) was combined with 3N HCl (10 mL) and acetone (10 mL), and the reaction mixture was stirred overnight at room temperature. The reaction mixture was then neutralized with 1N sodium hydroxide (30 mL) and extracted with diethyl ether. The organic extracts were combined, dried over anhydrous sodium sulfate, filtered and concentrated under vacuum to provide 1-cyclopentyl-2-(2-pyridyl)butan-1-one-4-al (0.165 g).

Preparation of Final Title Compound.

Scheme IV, step A: 1-cyclopentyl-2-(2-pyridyl)butan-1-one-4-al (0.38 g, 1.64 mmol, prepared in Scheme III, step C above) is combined with intermediate 1D (1.64 mmol, prepared in Example 1) in methylene chloride (20 mL) with acetic acid (0.23 mL, 4.1 mmol) and sodium triacetoxyborohydride (0.45 g, 2.1 mmol). The reaction mixture is stirred at room temperature for 16 hours. It is then made basic with 1N sodium hydroxide and extracted with methylene chloride (20 mL). The organic extract is dried over anhydrous sodium sulfate, filtered and concentrated under vacuum. The residue can then be purified by flash chromatography (ethyl acetate:hexane, 6:4, silica gel) to provide the final title compound.

EXAMPLE 5

Preparation of

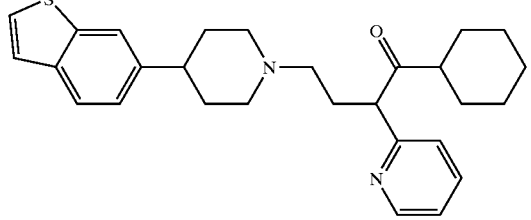

Preparation of 6-benzo(b)thiophene-piperidine.

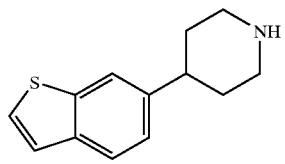

Scheme I, step E: Intermediate 1D (3.5 mmol, prepared in Example 1) is dissolved in ethanol (25 mL). 10% Palladium on carbon (2.25 g) is added and the reaction is stirred under hydrogen at 60 psi at room temperature overnight. The reaction mixture is filtered and the filtrate is concentrated to provide 6-benzo(b)thiophene-piperidine.

Preparation of Final Title Compound.

Scheme IV, step A; 1-cyclohexyl-2-(2-pyridyl)butan-1-one-4-al (0.20 g, 0.83 mmol, prepared in Example 1) is combined with 6-benzo(b)thiophene-piperidine (0.60 mmol) in methylene chloride (10 mL) with acetic acid (0.09 mL, 1.5 mmol) and sodium triacetoxyborohydride (0.17 g, 0.78 mmol). The reaction mixture is stirred at room temperature overnight. It is then made basic with 1 N sodium hydroxide and extracted with methylene chloride. The organic extract is dried over anhydrous sodium sulfate, filtered and concentrated under vacuum. The residue can then be purified by flash chromatography (2% methanol/ethyl acetate, silica gel) to provide the final title compound.

EXAMPLE 6
Preparation of 4-(6-benzo(b)thiophene-1,2,3,6-tetrahydropyridyl)-1-cyclohexyl-2-(2-pyridyl)butane.

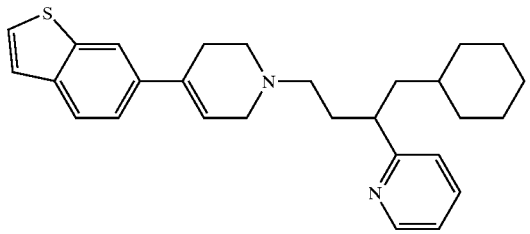

Preparation of 2-pyridyl-1-cyclohexylethane.

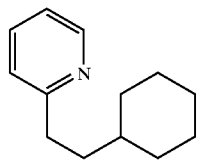

Scheme V, step A: 2-Picoline (5 g, 54 mmol) is dissolved in THF (100 mL) and cooled to −78° C. N-Butyllithium (40 mL of a 1.6M solution in THF, 64.3 mmol) was added to the solution over 10 minutes. The reaction mixture was then warmed to room temperature for 5 minutes and then cooled back down to −78° C. Then cyclohexylmethyl bromide (10 g, 57 mmol) was added, the reaction was warmed to room temperature and allowed to stir overnight. The reaction was then heated at reflux for 6 hours and then cooled to room temperature. The solvent was removed under vacuum and water and ethyl acetate were then added to the residue. The layers were separated and the aqueous was extracted with ethyl acetate. The organic extracts were combined, dried over anhydrous magnesium sulfate, filtered and concentrated to provide a dark oil. The oil was purified by flash chromatography to provide 2-pyridyl-1-cyclohexylethane (9 g, 89%).

Preparation of 2-pyridyl-3-cyclohexyl-butyraldehyde diethyl acetal.

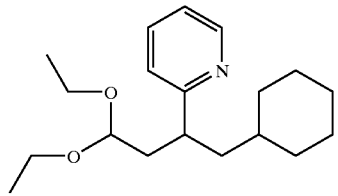

Scheme V, step B: 2-Pyridyl-1-cyclohexylethane (2 g, 10.6 mmol, prepared above) was dissolved in THF (20 mL) and cooled to −78° C. N-Butyllithium (13 mL of a 1.6 M solution in THF, 21.2 mmol) was added to the cooled solution. After stirring for 10 minutes, the cooling bath was removed and after 10 minutes, when the reaction had reached room temperature, it was re-cooled to −78° C. Bromoacetaldehyde diethyl acetal (2.1 g, 10.6 mmol) was then added and after one hour the cooling bath was removed. After 1.5 hours, n-Bu$_4$NBr was added and the reaction was then stirred overnight. Water was then added and the quenched reaction was extracted with ethyl acetate (3 times). The organic extracts were combined, dried over anhydrous sodium sulfate, filtered and concentrated under vacuum. The residue was purified by flash chromatography to provide 2-pyridyl-3-cyclohexyl-butyraldehyde diethyl acetal (1.5 g, 46%).

Preparation of 4-cyclohexyl-3-(2-pyridyl)-butyraldehyde.

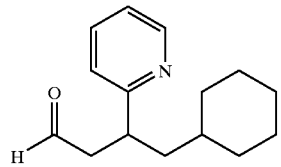

Scheme V, step C: 2-Pyridyl-3-cyclohexyl-butyraldehyde diethyl acetal (650 mg) was dissolved in acetone (10 mL), treated with HCl (a solution of 2.5 mL concentrated HCl and 7.5 mL water) and the reaction was stirred at room temperature overnight. 1N sodium hydroxide (30 mL) was then added and the neutralized reaction mixture was extracted with ethyl acetate (2 times). The organic extracts were combined, dried over anhydrous magnesium sulfate, filtered and concentrated under vacuum to provide 4-cyclohexyl-3-(2-pyridyl)-butyraldehyde (480 mg) as an oil.

Preparation of Final Title Compound.

Scheme V, step D: Intermediate 1D (0.82 mmol), 4-cyclohexyl-3-(2-pyridyl)-butyraldehyde (201 mg, 0.82 mmol), acetic acid (0.14 mL, 2.46 mmol), sodium triacetoxyborohydride (226 mg, 1.067 mmol) and methylene chloride (10 mL) are combined in a manner analogous to the procedure described in Example 1, Scheme IV, step A to provide the final title compound.

EXAMPLE 7
Preparation of 4-(6-benzo(b)thiophene-1,2,3,6-tetrahydropyridyl)-1-cyclohexyl-2-methyl-2-phenyl-butan-1-one.

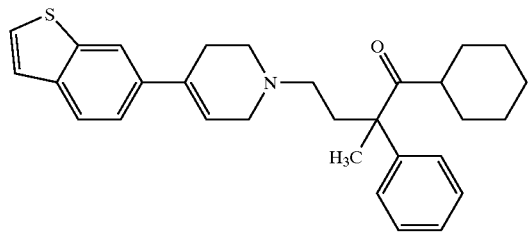

Preparation of 1-Cyclohexyl-2-phenylpropanol.

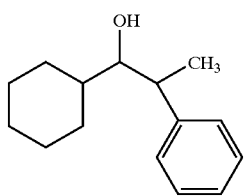

Scheme VI, step A: To a solution of cyclohexylmagnesium chloride (50 mmol) in 25 mL of Et$_2$O and 40 mL of THF at −5° C. was added a solution of 2-phenylpropanaldehyde (5.36 g, 40 mmol) in 10 mL of THF. The reaction mixture exothermed to 5° C. After stirring at room temperature for 75 min, the solution was poured onto ice cold 1 N HCl, extracted with toluene, dried over MgSO$_4$, and concentrated to give the title compound as a colorless oil (6.15 g, 70%): $^1$H NMR (d$^6$-DMSO): δ 7.23–7.30 (m, 2H, phenyl C<u>H</u>), 7.15–7.22 (m, 3H, phenyl C<u>H</u>), 4.17–4.51 (br s, 1H, —O<u>H</u>), 3.23–3.33 (m, 1H, R$_2$C <u>H</u>OH), 2.78 (dq, J=7.0 Hz, J=7.1 Hz, 1H, —C<u>H</u>(CH$_3$)Ph), 1.23–1.83 (m, 6H, cyclohexyl C<u>H</u>), 1.20 (d, J=6.9 Hz, 3H, —CH(C<u>H</u>$_3$)Ph), 0.88–1.18 (m, 5H, cyclohexyl C<u>H</u>).

Preparation of Cyclohexyl 1-phenylethyl ketone.

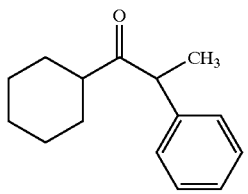

Scheme VI, step B: DMSO (118 mL, 1.6674 mol) was added dropwise to a solution of 126.42 g (0.579 mol) of 1-cyclohexyl-2-phenylpropanol in 1737 mL of $CH_2Cl_2$ (cooled in a wet ice acetone bath). After 29 min, 147.93 g (1.0422 mol) of $P_2O_5$ was added. After 11 min, the cooling bath was removed. An aliquot quenched with $Et_3N$ showed complete reaction within 3 h at RT. The reaction mixture was cooled in a wet ice acetone bath. $Et_3N$ (282 mL, 2.0265 mol) was added dropwise to the cooled reaction mixture over a 30 min period. The cooling bath was removed and the mixture was stirred overnight at RT. The reaction mixture was quenched by dropwise addition of 500 mL of 3 N HCl (aq) (pH=0). After shaking in separatory funnel, the aqueous phase was removed. The organic phase was washed with 500 mL of 3 N HCl (aq) (pH=0), washed twice with 1 L of 10% $K_2CO_3$ (aq) (pH=12;12), washed three times with 500 mL of NaOCl (aq) solution, washed with 1 L of water, washed with 1 L of 25% NaCl (aq), dried over $MgSO_4$, gravity filtered and concentrated under vacuum with dry ice trap to collect $Me_2S$. An amber oil of the title compound (107.01 g, 85.437%) was obtained;

$^1$H NMR ($d^6$-DMSO): δ 7.30–7.37 (m, 2H, phenyl CH), 7.21–7.28 (m, 3H, phenyl CH), 4.08 (q, J=6.9 Hz, 1H, —CH(CH$_3$)Ph), 2.40–2.49 (m, 1H, cyclohexyl CH), 1.82–1.84 (m, 1H, cyclohexyl-CH$_2$), 1.67–1.69 (m, 1H, cyclohexyl-CH$_2$), 1.52–1.63 (m, 1H, cyclohexyl-CH$_2$), 1.34–1.43 (m, 1H, cyclohexyl-CH$_2$), 1.26 (d, J=6.9 Hz, 3H, —CH(CH$_3$)Ph), 1.01–1.24 (m, 4H, cyclohexyl-CH$_2$).

Preparation of 2-phenyl-2-methyl-4-pentenoyl cyclohexane.

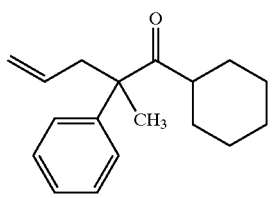

Scheme VI, step C; A solution of 31.39 g (0.2797 mol) of t-BuOK in 100 mL of THF was added dropwise to a solution of 55.00 g (0.2543 mol) of cyclohexyl 1-phenylethyl ketone and 26.4 mL (0.3052 mol) of alkyl bromide in 136 mL of THF (cooled in a wet ice acetone bath). THF washings (16 mL) were added to the reaction mixture. The cooling bath was removed after addition. After reaction completion (2 h), the reaction mixture was quenched with 300 mL of 1 N HCl (pH=0) and extracted with 300 mL of heptane. The heptane extract was washed with 10% $NaHCO_3$ (aq) (pH=9), dried over $MgSO_4$, gravity filtered and concentrated under vacuum to afford 59.70 g (91.58%) of title compound as an amber oil: $^1$H NMR ($d^6$-DMSO): δ 7.32–7.42 (m, 2H, phenyl CH), 7.24–7.31 (m, 3H, phenyl CH), 5.34–5.47 (m, 1H, —CH=CH$_2$), 5.02 (dd, J=17.1 Hz, J=2.1 Hz, 1H, —CH=CH—H (trans)), 4.97 (ddd, J=10.2 Hz, J=2.2 Hz, J=1.0 Hz, 1H, —CH=CH—H (cis, W-coupling)), 2.66 (ddd, J=14.2 Hz, J=6.9 Hz, J=1.0 Hz, 1H, —CH$_2$CH=CH$_2$), 2.59 (ddd, J=14.2 Hz, J=7.3 Hz, J=1.0 Hz, 1H, —CH$_2$CH=CH$_2$), 2.38–2.49 (m, 1H, cyclohexyl CH), 1.48–1.69 (m, 4H, cyclohexyl-CH$_2$), 1.46 (s, 3H, —CH(CH$_3$)Ph), 1.36–1.44 (m, 1H, cyclohexyl-CH$_2$), 0.82–1.36 (m, 5H, cyclohexyl-CH$_2$).

Preparation of 4-Cyclohexyl-3-methyl-4-oxo-3-phenylbutyraldehyde.

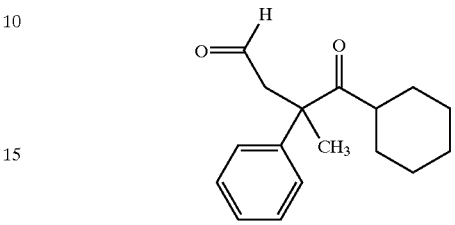

Scheme VI, step D: Ozone was bubbled through a cloudy mixture of 56.50 g (0.2204 mol) of 2-phenyl-2-methyl-4-pentenoyl cyclohexane and a small amount (~10 mg) of Sudan III in 220 mL of MeOH (cooled in a dry ice acetone bath at −20° C.) for 4 h until pink color turned to pale yellow color. After all of the olefin was consumed, $Me_2S$ (50 mL) was added to reaction mixture. The cooling bath was removed. The exotherm rose to 38° C. and mixture was cooled in cooling bath until there was no exotherm. Then the cooling bath was removed and the mixture was stirred overnight. The reaction solution was concentrated under vacuum with dry ice trap to collect excess $Me_2S$ to afford 83.65 g of crude 4-cyclohexyl-3-methyl-4-oxo-3-phenylbutyraldehyde dimethyl acetal as a pink oil: $^1H$ $NMR$ ($d^6$-DMSO): δ 7.34–7.39 (m, 2H, phenyl CH), 7.24–7.30 (m, 3H, phenyl CH), 3.99 (dd, J=4.2 Hz, J=5.9 Hz, 1H, CH(OCH$_3$)$_2$), 3.14 (s, 3H, CH(OCH$_3$)$_2$), 3.06 (s, 3H, CH(OCH$_3$)$_2$), 2.34–2.43 (m, 1H, cyclohexyl CH), 2.10–2.20 (m, 2H, —CH$_2$CH(OCH$_3$)$_2$), 1.55–1.67 (m, 1H, cyclohexyl-CH$_2$), 1.53 (s, 3H, R$_2$C(CH$_3$)Ph), 0.80–1.52 (m, 9H, cyclohexyl-CH$_2$).

To a solution of 82.65 g (66.29 g, 0.2177 mol) of 4-cyclohexyl-3-methyl-4-oxo-3-phenylbutyraldehyde dimethyl acetal in 539 mL of acetone was added 539 mL of 3 N HCl (aq) at RT. After reaction completion (2 h), the mixture was concentrated to 426.5 g (or 1/3 volume) of residue (RT-40° C.). The residue contained mostly water (pH=0) and was extracted twice with 300 mL of MTBE. The MTBE extract was washed with 300 mL of 25% NaCl (aq), dried over $MgSO_4$, gravity filtered and concentrated to afford 54.92 g (97.65%) of title compound as a pink oil: $^1$H NMR ($d^6$-DMSO): δ 9.54 (t, J=2.0 Hz, 1H, —CHO), 7.36–7.45 (m, 2H, phenyl CH), 7.28–7.35 (m, 3H, phenyl CH), 2.95 (dd, J=16.6 Hz, J=1.9 Hz, 1H, CH$_2$CHO), 2.85 (dd, J=16.6 Hz, J=1.7 Hz, 1H, CH$_2$CHO), 2.41–2.49 (m, 1H, cyclohexyl CH), 1.72 (s, 3H, R$_2$C(CH$_3$)Ph), 0.85–1.66 (m, 10H, cyclohexyl-CH$_2$).

Preparation of Final Title Compound.

Scheme IV, step A: Intermediate 1D (0.82 mmol), 4-cyclohexyl-3-methyl-4-oxo-3-phenylbutyraldehyde (0.82 mmol), acetic acid (0.14 mL, 2.46 mmol), sodium triacetoxyborohydride (226 mg, 1.067 mmol) and methylene chloride (10 mL) are combined in a manner analogous to the procedure described in Example 1, to provide the final title compound.

EXAMPLE 8

Preparation of 4-(6-benzo(b)thiophene-1,2,3,6-tetrahydropyridyl)-1-cyclohexyl-2-methyl-2-(2-pyridyl)-butan-1-one.

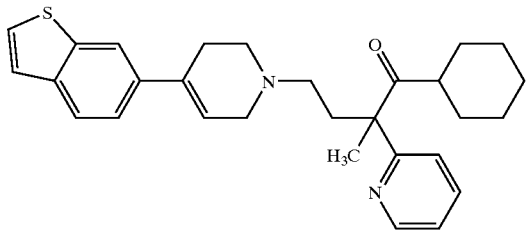

Preparation of 4-Cyclohexyl-3-methyl-4-oxo-3-(2-pyridyl) butyraldehyde.

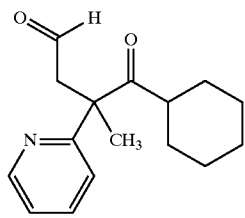

Scheme VI, steps A–D: 4-Cyclohexyl-3-methyl-4-oxo-3-(2-pyridyl)butyraldehyde is prepared from 2-(2-pyridyl)-propanaldehyde in a manner analogous to the procedure described in example 7 for the preparation of 4-cyclohexyl-3-methyl-4-oxo-3-phenylbutyraldehyde.

Preparation of Final Title Compound.

Scheme IV, step A: Intermediate 1D (0.82 mmol), 4-cyclohexyl-3-methyl-4-oxo-3-(2-pyridyl)butyraldehyde (0.82 mmol), acetic acid (0.14 mL, 2.46 mmol), sodium triacetoxyborohydride (226 mg, 1.067 mmol) and methylene chloride (10 mL) are combined in a manner analogous to the procedure described in Example 1, to provide the final title compound.

EXAMPLE 9

Preparation of:

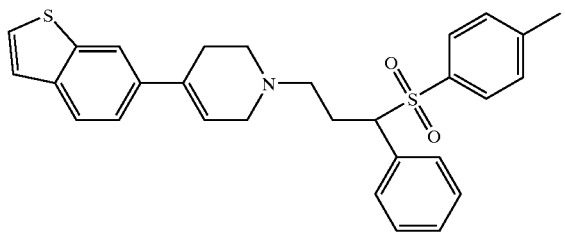

The following aldehyde:

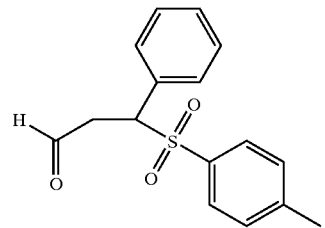

(0.20 g, 0.69 mmol) is combined with intermediate 1D (0.76 mmol, prepared in example 1) in methylene chloride (20 mL) and stirred for 20 minutes. The reaction mixture is then treated with acetic acid (0.06 mL, 1.04 mmol) and sodium triacetoxyborohydride (0.19 g, 0.90 mmol) and stirred for 2 hours. The reaction is then quenched with 1N sodium hydroxide and extracted with methylene chloride. The organic extracts are combined, dried over anhydrous sodium sulfate, filtered and concentrated under vacuum. The residue can then be purified by flash chromatography (silica gel, 50% ethyl acetate/hexane) to provide the title.

EXAMPLE 10

Preparation of 4-(5-benzo(b)thiophene-1,2,3,6-tetrahydropyridyl)-1-cyclohexyl-2-(2-pyridyl)butan-1-one.

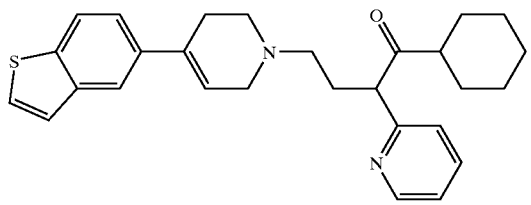

Preparation of Intermediate 1A.

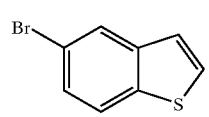

(1 E)

Scheme I, steps A and B: A mixture of 4-bromothiophenol (10 g, 53 mmol, 1 eq.), 2-bromomethyl-1,3-dioxolane (11 g, 58 mmol, 1.1 eq.) and $K_2CO_3$ (11 g, 80 mmol, 1.5 eq.) in 100 mL of DMF was stirred at room temperature for 48 hours. Water was added to the reaction mixture and the mixture was extracted with ethyl acetate 2 times. The combined organic extracts were washed with 1 N NaOH, water, brine, dried with anhydrous $Na_2SO_4$, filtered, and concentrated under reduced pressure. The residue was dissolved in chlorobenzene and the solution was added dorpwise into a boiling solution 40 g of PPA in chlorobenzene. The reaction was kept at reflux for 8 hours. The solution was decanted from the residue and toluene was added to the residue, stirred and decanted. The solution and the extracts were combined and concentrated under reduced pressure. The residue was dissolved in ethyl acetate, and the solution was washed with 10% of $Na_2CO_3$ (aq), water, brine, dried with anhydrous $Na_2SO_4$, filtered, and concentrated under reduced pressure. The residue was subjected to silica gel chromatography, eluting with hexane. The fractions containing product were combined and concentrated under reduced pressure to provide 6 g of intermediate 1E as an oil which was later solidified as a yellow solid.

Preparation of Intermediate 1F:

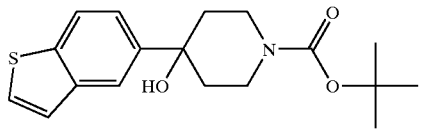

(1 F)

Scheme I, step C: To a solution of intermediate 1E (3 g, 14.1 mmol, 1 eq.) and Mg (0.69 g, 28.2 mmol, 2 eq.) in 100 mL ether was added BrCH$_2$CH$_2$Br (1.2 mL, 14.1 mmol, 1 eq.) dropwise. 30 minutes after the addition, the reaction was heated at reflux gently for 2 hours. The reaction was allowed to cool down to room temperature and 1-(t-butoxycarbonyl)-4-piperidone (3.1 g, 15.5 mmol, 1.1 eq.) in ether was added into the solution. The reaction mixture was then heated at reflux for another 2 hours before it was stirred at room temperature over night. Water was added to the mixture and the mixture was extracted with ethyl acetate 3 times. The combined organic extracts were washed with water, brine, dried with anhydrous Na$_2$SO$_4$, filtered, and concentrated under reduced pressure to provide intermediate 1F.

Preparation of Intermediate 1G.

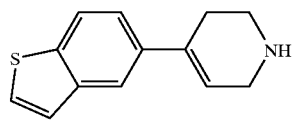

(1 G)

Scheme I, step D: Intermediate 1F (3.6 g, 10.7 mmol, 1 eq) was dissolved in 100 mL of toluene. PTSA (4.1 g, 21.6 mmol, 2 eq.) was added to the solution and the mixture was heated at reflux for 1 hour. The reaction was allowed to cool down to room temperature and concentrated under reduced pressure. The residue was dissolved in ethyl acetate and the solution was washed with 1N NaOH 4 times, water, brine, dried with anhydrous Na$_2$SO$_4$, fitlered, and concentrated at reduced pressure to give 1.14 g of intermediate 1G as an oil.

Preparation of the Final Title Compound.

Scheme IV, step A: To a solution of intermediate 1G (598 mg, 2.78 mmol, 1 eq.) and 1-cyclohexyl-2-(2-pyridyl)butan-1-one-4-al (680 mg, 2.78 mmol, 1 eq.) in 20 mL methylene chloride, was added acetic acid (0.478 mL, 8.342 mmol, 3 eq.) followed by sodium triacetoxyborohydride (766 mg, 3.61 mmol, 1.3 eq.). The reaction was stirred at room temperature for 3 hours. NaOH (aq. 1 N) was added and the mixture was extracted with ethyl acetate 3 times. The combined organic extracts were dried with anhydrous Na$_2$SO$_4$, filtered, and concentrated under reduced pressure. The residue was subjected to silica gel chromatography, eluting with ethyl acetate. The fractions containing product were combined and concentrated under reduced pressure to provide 743.6 mg final title compound which was then converted to its oxalate salt with equivalents of oxalic acid; MS=445.4 (M+1); mp 194–196° C. (oxalate).

EXAMPLE 11

Preparation of 4-(5-benzo(b)thiophene-1,2,3,6-tetrahydropyridyl)-1-cyclohexyl-2-(2-pyridyl)butan-1-ol.

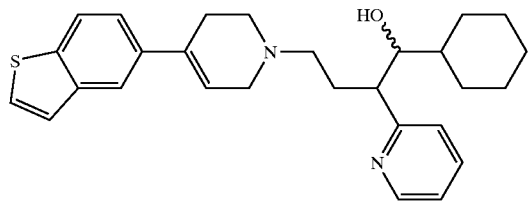

Scheme IV, step C: To a suspension of LiAlH$_4$ (58 mg, 1.53 mmol, 3 eq.) in 100 mL of diethyl ether, was added a solution of 4-(5-benzo(b)thiophene-1,2,3,6-tetrahydropyridyl)-1-cyclohexyl-2-(2-pyridyl)butan-1-one (228 mg, 0.51 mmol, 1 eq.) in portions at room temperature. After 1 hour, the reaction was quenched by addition of Na$_2$SO$_4$.10H$_2$O to the reaction mixture. The mixture was then filtered and the filtrate was concentrated under reduced pressure. The residue was subjected to silica gel chromatography, eluting with ethyl acetate. The fractions containing product were combined and concentrated under reduced pressure to provide 55 mg of isomer 1 of the title compound which was converted to its oxalate salt with 1 equivalent of oxalic acid; MS=447.1 (m+1); mp=205–207° C. (oxalate) and 86 mg of isomer 2 of the title compound which was also converted to it oxalate salt with 1 equivalent of oxalic acid; MS=447.2 (m+1); mp=190–192° C. (oxalate).

EXAMPLE 12

Preparation of 4-(5-benzo(b)thiophene-1,2,3,6-tetrahydropyridyl)-1-cycloheptyl-2-(2-pyridyl)butan-1-one.

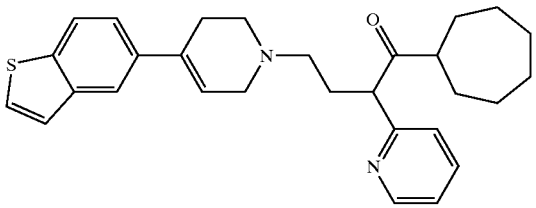

The title compound can be prepared in a manner analogous to the procedure described in example 3 from intermediate 1G and 1-cycloheptyl-2-(2-pyridyl)butan-1-one-4-al.

EXAMPLE 13

Preparation of 4-(5-benzo(b)thiophene-1,2,3 6-tetrahydropyridyl)-1-cyclopentyl-2-(2-pyridyl)butan-1-one.

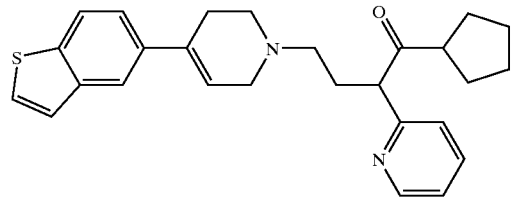

The title compound can be prepared in a manner analogous to the procedure described in example 4 from intermediate 1G and 1-cyclopentyl-2-(2-pyridyl)butan-1-one-4-al.

EXAMPLE 14

Preparation of 4-(5-benzo(b)thiophene-piperidine)-1-cyclohexyl-2-(2-pyridyl)butan-1-one

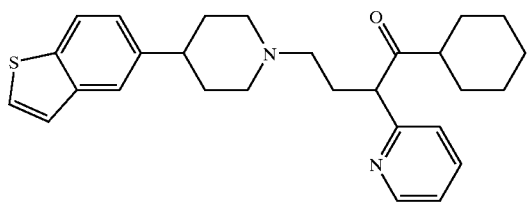

Preparation of 5-benzo(b)thiophene-piperidine.

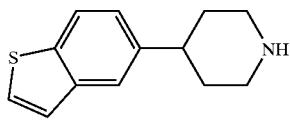

Scheme I, step E: Intermediate 1G (3.5 mmol) is dissolved in ethanol (25 mL). 100% Palladium on carbon (2.25 g) is added and the reaction is stirred under hydrogen at 60 psi at room temperature overnight. The reaction mixture is filtered and the filtrate is concentrated to provide 5-benzo(b)thiophene-piperidine.

Preparation of Final Title Compound.

Scheme IV, step A; 1-cyclohexyl-2-(2-pyridyl)butan-1-one-4-al (0.20 g, 0.83 mmol, prepared in Example 1) is combined with 5-benzo(b)thiophene-piperidine (0.60 mmol) in methylene chloride (10 mL) with acetic acid (0.09 mL, 1.5 mmol) and sodium triacetoxyborohydride (0.17 g, 0.78 mmol). The reaction mixture is stirred at room temperature overnight. It is then made basic with 1N sodium hydroxide and extracted with methylene chloride. The organic extract is dried over anhydrous sodium sulfate, filtered and concentrated under vacuum. The residue can then be purified by flash chromatography (2% methanol/ethyl acetate, silica gel) to provide the final title compound.

EXAMPLE 15

Preparation of 4-(5-benzo(b)thiophene-1,2,3,6-tetrahydropyridyl)-1-cyclohexyl-2-(2-pyridyl)butane.

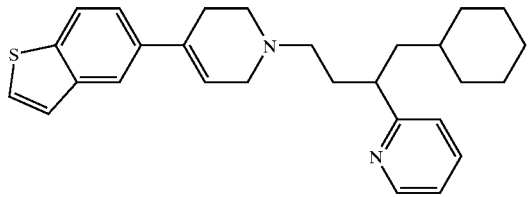

The title compound can be prepared in a manner analogous to the procedure described in example 6 from intermediate 1G and 4-cyclohexyl-3-(2-pyridyl)-butyraldehyde.

EXAMPLE 16

Preparation of 4-(5-benzo(b)thiophene-1,2,3,6-tetrahydropyridyl)-1-cyclohexyl-2-methyl-2-phenyl-butan-1-one.

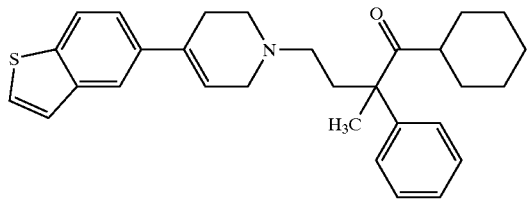

The title compound can be prepared in a manner analogous to the procedure described in example 7 from intermediate 1G and 4-cyclohexyl-3-methyl-4-oxo-3-phenylbutyraldehyde.

EXAMPLE 17

Preparation of 4-(5-benzo(b)thiophene-1,2,3,6-tetrahydropyridyl)-1-cyclohexyl-2-methyl-2-(2-pyridyl)-butan-1-one.

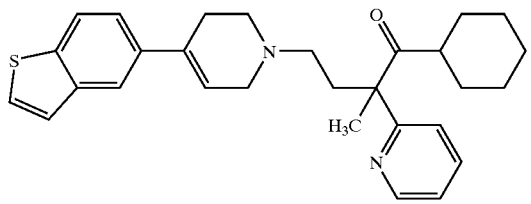

The title compound can be prepared in a manner analogous to the procedure described in example 8 from intermediate 1G and 4-cyclohexyl-3-methyl-4-oxo-3-(2-pyridyl) butyraldehyde.

EXAMPLE 18

Preparation of:

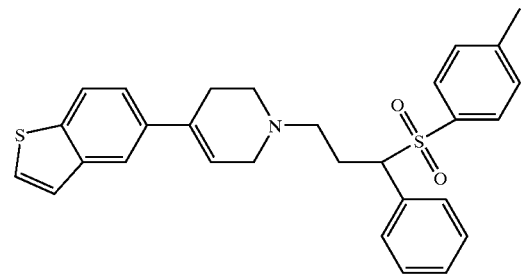

The title compound can be prepared in a manner analogous to the procedure described in example 9 from intermediate 1G and aldehyde:

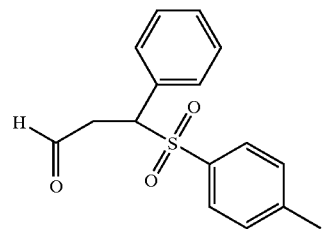

EXAMPLE 19

Preparation of 4-(2-benzo(b)thiophene-1,2,3,6-tetrahydropyridyl)-1-cyclohexyl-2-(2-pyridyl)butan-1-one.

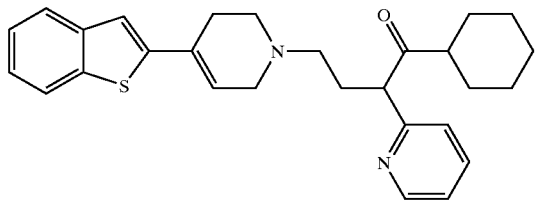

Preparation of intermediate 1J.

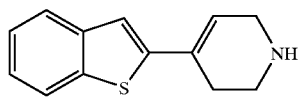

Scheme I, steps C and D: To a solution of benzo[b]thiophene (2 g, 14.5 mmol, 1 eq.) in 50 mL THF cooled with dry ice acetone bath, was added n-BuLi (9.5 mL, 15.2 mmol, 1.05 eq.) dropwise. After 15 minutes, 1-(t-butoxycarbonyl)-4-piperidone (2.97 g, 14.5 mmol, 1 eq.) in 10 mL THF was added. The reaction mixture was stirred at room temperature over night. Water was added to the mixture and the mixture was extracted with ethyl acetate 3 times. The combined organic layer was washed with water, brine, dried with anhydrous Na$_2$SO$_4$, filtered, and concentrated under reduced pressure. The residue was dissolved in 100 mL of toluene. PTSA (5.5 g, 290 mmol, 2 eq.) was added to the solution and the mixture was heated at reflux for 1 hour. The reaction was let to cool down to room temperature and concentrated under reduced pressure. The residue was dissolved in ethyl acetate and the solution was washed with 1N NaOH 4 times, water, brine, dried with anhydrous Na$_2$SO$_4$, filtered, and concentrated at reduced pressure to give 550 mg of 1J as an oil.

Preparation of Final Title Compound.

Scheme IV, step A: To a solution of 1J (300 mg, 1.39 mmol, 1 eq) and 1-cyclohexyl-3-(2-(1,3-diethylacetal))-2-(2-pyridyl)propan-1-one (400 mg, 1.63 mmol, 1.17eq., see preparation 2) in 20 mL THF, was added acetic acid (0.238 mL, 4.2 mmol, 3 eq.) followed by sodium triacetoxyborohydride (0.35 g, 1.65 mmol). The reaction was stirred at room temperature for 3 hours. NaOH (aq. 1 N) was added and the mixture was extracted with ethyl acetate 3 times. The combined organic extracts were dried with anhydrous Na$_2$SO$_4$, filtered, and concentrated under reduced pressure. The residue was subjected to silica gel chromatography, eluting with ethyl acetate. The fractions containing product were combined and concentrated under reduced pressure to provide 505 mg of final title compound. 150 mg of the final title compound was converted to its oxalate salt with 1 equivalent of oxalic acid; MS=445.3 (M+1); mp 228–230° C. (oxalate).

EXAMPLE 20

Preparation of 4-(2-benzo(b)thiophene-1,2,3,6-tetrahydropyridyl)-1-cyclohexyl-2-(2-pyridyl)butan-1-ol.

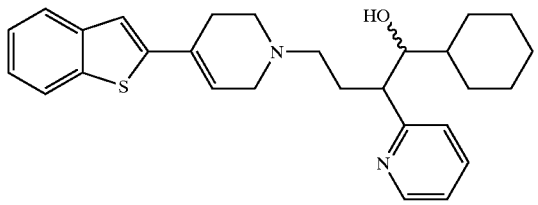

Scheme IV, step C: To a suspension of LiAlH$_4$ (73 mg, 1.95 mmol, 3 eq.) in 100 mL of diethyl ether was added a solution of 4-(2-benzo(b)thiophene-1,2,3,6-tetrahydropyridyl)-1-cyclohexyl-2-(2-pyridyl)butan-1-one (290 mg, 0.65 mmol, 1 eq.) in portions at room temperature. After 1 hour the reaction was quenched by addition of Na$_2$SO$_4$.10H$_2$O to the reaction mixture. The mixture was then filtered and the filtrate was concentrated under reduced pressure. The residue was subjected to silica gel chromatography, eluting with ethyl acetate. The fractions containing product were combined and concentrated under reduced pressure to provide 74.5 mg of isomer 1 of title compound which was converted to its oxalate salt: MS=447.2 (m+1); mp=220–221° C. (oxalate), and 85 mg of isomer 2 of the title compound which was also converted to its oxalate salt; MS=447.2 (m+1); mp=210–212° C. (oxalate).

EXAMPLE 21

Preparation of 4-(2-benzo(b)thiophene-1,2,3,6-tetrahydropyridyl)-1-cycloheptyl-2-(2-pyridyl)butan-1-one.

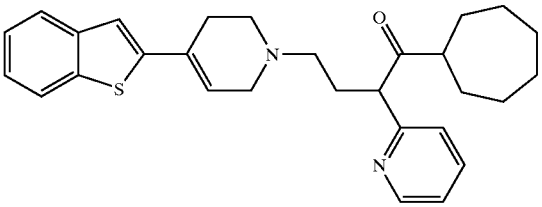

The title compound can be prepared in a manner analogous to the procedure described in example 3 from intermediate 1J and 1-cycloheptyl-2-(2-pyridyl)butan-1-one-4-al.

EXAMPLE 22

Preparation of 4-(2-benzo(b)thiophene-1,2,3,6-tetrahydropyridyl)-1-cyclopentyl-2-(2-pyridyl)butan-1-one.

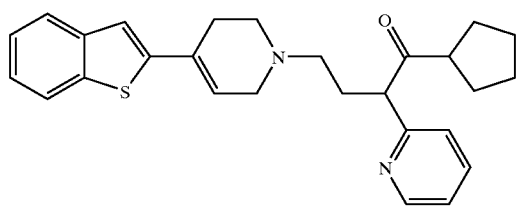

The title compound can be prepared in a manner analogous to the procedure described in example 4 from intermediate 1J and 1-cyclopentyl-2-(2-pyridyl)butan-1-one-4-al.

EXAMPLE 23

Preparation of 4-(2-benzo(b)thiophene-piperidine)-1-cyclohexyl-2-(2-pyridyl)butan-1-one

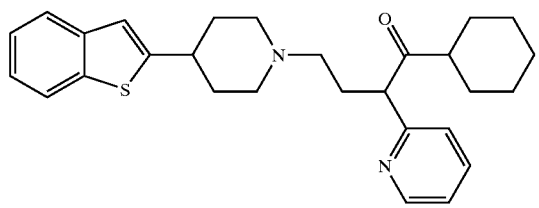

Preparation of 2-benzo(b)thiophene-piperidine.

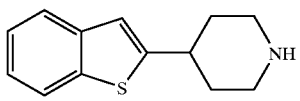

Scheme I, step E: Intermediate 1J (3.5 mmol) is dissolved in ethanol (25 mL). 10% Palladium on carbon (2.25 g) is added and the reaction is stirred under hydrogen at 60 psi at room temperature overnight. The reaction mixture is filtered and the filtrate is concentrated to provide 2-benzo(b)thiophene-piperidine.

Preparation of Final Title Compound.

Scheme IV, step A; 1-cyclohexyl-2-(2-pyridyl)butan-1-one-4-al (0.20 g, 0.83 mmol, prepared in Example 1) is combined with 2-benzo(b)thiophene-piperidine (0.60 mmol) in methylene chloride (10 mL) with acetic acid (0.09 mL, 1.5 mmol) and sodium triacetoxyborohydride (0.17 g, 0.78 mmol). The reaction mixture is stirred at room temperature overnight. It is then made basic with 1N sodium hydroxide and extracted with methylene chloride. The organic extract is dried over anhydrous sodium sulfate, filtered and concentrated under vacuum. The residue can then be purified by flash chromatography (2% methanol/ethyl acetate, silica gel) to provide the final title compound.

EXAMPLE 24

Preparation of 4-(2-benzo(b)thiophene-1,2,3,6-tetrahydropyridyl)-1-cyclohexyl-2-(2-pyridyl)butane.

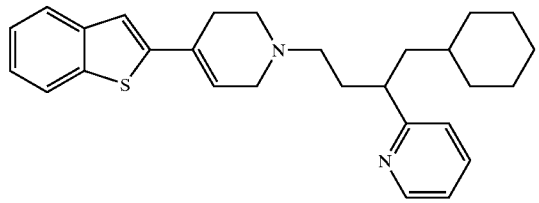

The title compound can be prepared in a manner analogous to the procedure described in example 6 from intermediate 1J and 4-cyclohexyl-3(2-pyridyl)-butyraldehyde.

EXAMPLE 25

Preparation of 4-(2-benzo(b)thiophene-1,2,3,6-tetrahydropyridyl)-1-cyclohexyl-2-methyl-2-phenyl-butan-1-one.

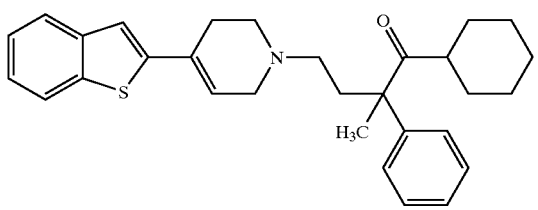

The title compound can be prepared in a manner analogous to the procedure described in example 7-from intermediate 1J and 4-cyclohexyl-3-methyl-4-oxo-3-phenylbutyraldehyde.

EXAMPLE 26

Preparation of 4-(2-benzo(b)thiophene-1,2,3,6-tetrahydropyridyl)-1-cyclohexyl-2-methyl-2-(2-pyridyl)-butan-1-one.

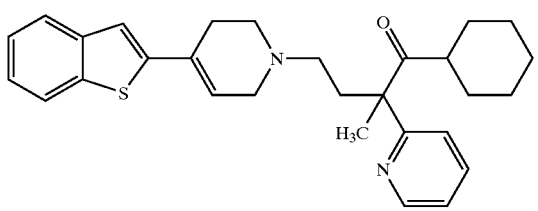

The title compound can be prepared in a manner analogous to the procedure described in example 8 from intermediate 1J and 4-cyclohexyl-3-methyl-4-oxo-3-(2-pyridyl)butyraldehyde.

EXAMPLE 27

Preparation of:

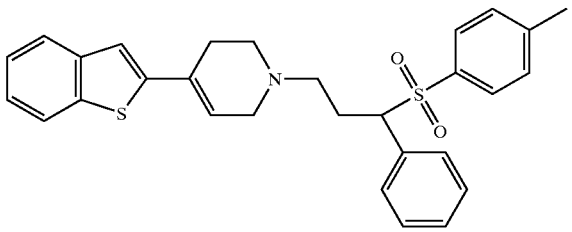

The title compound can be prepared in a manner analogous to the procedure described in example 9 from intermediate 1J and aldehyde:

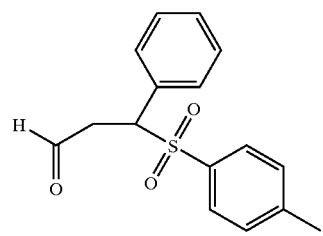

EXAMPLE 28

Preparation of 4-(3-benzo(b)thiophene-1,2,3,6-tetrahydropyridyl)-1-cyclohexyl-2-(2-pyridyl)butan-1-one.

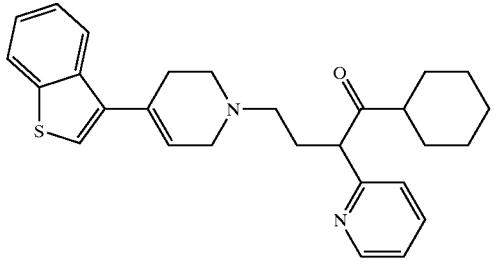

Preparation of 3-bromobenzo(b)thiophene.

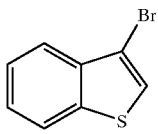

Benzothiophene (2.68 g, 20.0 mmol) was dissolved in glacial acetic acid (100 mL) and cooled to 0° C. The resulting solution was treated by dropwise addition of bromine (1.08 mL, 21.0 mmol). The reaction mixture was allowed to warm to room temperature and was stirred for 16 hours. The crude mixture was concentrated to an oil. The residue was purified by silica gel chromatography eluting with hexane to obtain 4.02 g (94%) 3-bromobenzothiophene.

Preparation of 1-(t-butoxycarbonyl)-4-hydroxy-4-tributylstannyl piperidine.

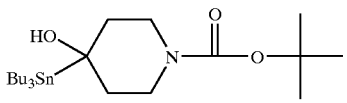

Scheme IIb, step A: Diisopropylamine (25.2 mL, 0.18 mol) in anhydrous THF (500 mL) was cooled to 0° C. and n-butyllithium (112.5 mL of a 1.6 M solution in THF, 0.18 mol) was added dropwise over 20 minutes to the cooled solution. The reaction mixture was stirred for an additional 15 minutes at 0° C. and then tri-n-butyltinhydride (48.4 mL, 0.18 mol) was added dropwise over 30 minutes. The reaction mixture was then stirred for one hour and then cooled to −78° C. N-(t-butoxycarbonyl)-4-piperidone (30.0 g, 0.15 mol) in THF (500 mL) was then added dropwise to the cooled solution over one hour. After addition was complete, the reaction was stirred for 2 hours at −78° C. and then quenched with buffer (pH 6). The mixture was extracted with ethyl acetate, the organic extracts were combined, dried over anhydrous sodium sulfate, filtered and concentrated under vacuum. The residue was purified by flash chromatography (5% ethyl acetate/hexane to provide 1-(t-butoxycarbonyl)-4-hydroxy-4-tributylstannyl piperidine (36.06 g).

Preparation of 1-(t-butoxycarbonyl)-4-tributylstannyl-1,2,3,6-tetrahydropyridyl.

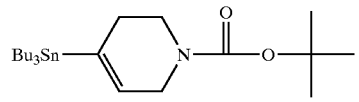

Scheme IIb, step B: 1-(t-butoxycarbonyl)-4-hydroxy-4-tributylstannyl piperidine (36.0 g, 73.4 mmol, prepared in Scheme II, step A above) was dissolved in methylene chloride (250 mL) and cooled to 0° C. Triethylamine (30.7 mL, 220 mmol) and methanesulfonyl chloride (8.56 mL, 110 mmol) were added to the solution which was warmed to room temperature and allowed to stir for 4 hours. An additional amount of methanesulfonyl chloride (4.28 mL) and triethylamine (15.3 mL) was added and the reaction was allowed to stir for an additional hour at room temperature. The reaction mixture was then stored in a freezer overnight. The crude reaction mixture was then concentrated under vacuum. The residue was then purified by flash chromatography (5% ethyl acetate/hexane, silica gel) to provide 1-(t-butoxycarbonyl)-4-tributylstannyl-1,2,3,6-tetrahydropyridyl (24.75 g, 79%).

Preparation of 1-(t-butoxycarbonyl)-4-(3-benzo(b)thiophene)-1,2,3,6-tetrahydropyridyl.

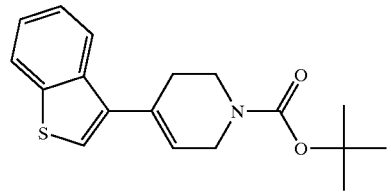

Scheme IIb, step C: 3-bromobenzo(b)thiophene (2.094 g, 9.83 mmol), 1-(t-butoxycarbonyl)-4-tributylstannyl-1,2,3,6-tetrahydropyridyl (4.641 g, 9.83 mmol), 2,6-di-t-butyl-4-methylphenol (0.10 g, 0.45 mmol), and tetrakis(triphenylphosphine)palladium(0) (0.386 g, 0.334 mmol) were combined in toluene (40 mL). The reaction mixture was heated at reflux for 14 hours. It was then cooled, filtered, and concentrated to dryness. The residue was purified by flash chromatography (5% ethyl acetate/hexane, silica gel) to provide 1.5 g intermediate title compound contaminated with tin biproduct.

Preparation of 4-(3-benzo(b)thiophene)-1,2,3,6-tetrahydropyridyl.

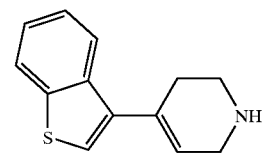

Scheme IIb, step D: 1-(t-butoxycarbonyl)-4-(3-benzo(b)thiophene)-1,2,3,6-tetrahydropyridyl (1.5 g, 4.8 mmol), was dissolved in toluene (40 mL) and treated with p-toluenesulfonic acid (1.8 g, 9.5 mmol). The reaction mixture was heated at 80° C. for 20 minutes, then cooled to room temperature. No starting material was detected by thin layer chromatography. The crude reaction mixture was washed with saturated sodium carbonate solution, dried over anhydrous sodium sulfate, filtered, and concentrated to an oil. The residue was purified by flash chromatography (20% methanol/dichloromethane with ammonia) to obtain 4-(3-benzo(b)thiophene)-1,2,3,6-tetrahydropyridyl (0.410 g).

Preparation of Final Title Compound.

Scheme IV, step A: 4-(3-benzo(b)thiophene)-1,2,3,6-tetrahydropyridyl (0.40 g, 2.0 mmol) was combined with 1-cyclohexyl-2-(2-pyridyl)butan-1-one-4-al (0.49 g, 2.0 mmol) in methylene chloride (50 mL) with acetic acid (0.34 mL, 6.0, mmol), and sodium triacetoxyborohydride (0.55 g, 2.6 mmol). The reaction mixture was stirred at room temperature for 16 hours. It was then treated with 1N sodium hydroxide solution and extracted with methylene chloride. The combined organic extracts were dried over anhydrous sodium sulfate, filtered, and concentrated under vacuum. The residue was purified by flash chromatography (ethyl acetate, silica gel) to provide the final title compound (0.67 g, 75%). The final title compound was treated with oxalic acid (0.136 g, 1.51 mmol) in methanol. The solution was concentrated to provide the oxalate salt of the final title compound as a crystalline solid (0.72 g); mp 208–210° C., mass spectrum 445 (M+1).

EXAMPLE 29

Preparation of 4-(3-benzo(b)thiophene-1,2,3,6-tetrahydropyridyl)-1-cyclohexyl-2-(2-pyridyl)butan-1-ol.

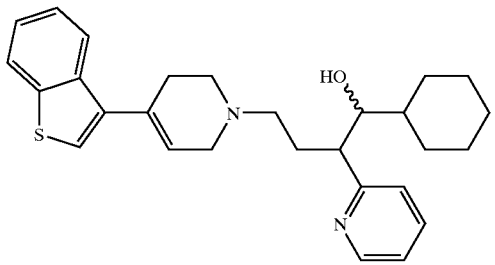

Scheme IV, step C: 4-(3-Benzo(b)thiophene-1,2,3,6-tetrahydropyridyl)-1-cyclohexyl-2-(2-pyridyl)butan-1-one (0.20 g, 0.45 mmol) dissolved in dry diethyl ether (50 mL) was treated with lithium aluminum hydride (0.05 g, 1.35 mmol) at room temperature. The reaction mixture was stirred for 4 hours before it was quenched with saturated potassium sodium tartrate solution and extracted with ethyl acetate. The organic extracts were combined, dried over anhydrous sodium sulfate, filtered and concentrated under vacuum. The residue was purified by flash chromatography to provide a mixture of two enantiomer pairs A and B: Pair A: 0.035 g, 17%. Added oxalic acid (7.2 mg, 0.08 mmole) in methanol (5 mL) to obtain oxalate salt of pair A: mp 172–174° C., mass spectrum 447 (M+1). Pair B: 0.09 g, 45%. Added oxalic acid (18.2 mg, 0.20 mmole) in methanol (10 mL) to obtain the oxalate salt of pair B: mp 100–107° C., mass spectrum 447 (M+1).

EXAMPLE 30

Preparation of 4-(3-benzo(b)thiophene-1,2,3,6-tetrahydropyridyl)-1-cycloheptyl-2-(2-pyridyl)butan-1-one.

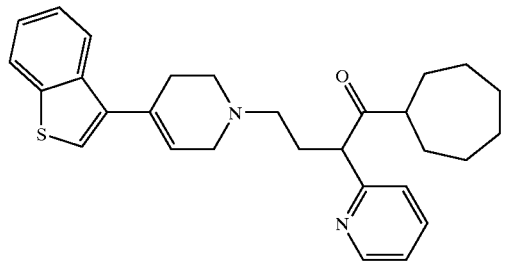

The title compound can be prepared in a manner analogous to the procedure described in example 3 from 4-(3-benzo(b)thiophene)-1,2,3,6-tetrahydropyridyl and 1-cycloheptyl-2-(2-pyridyl)butan-1-one-4-al.

EXAMPLE 31

Preparation of 4-(3-benzo(b)thiophene-1,2,3,6-tetrahydropyridyl)-1-cyclopentyl-2-(2-pyridyl)butan-1-one.

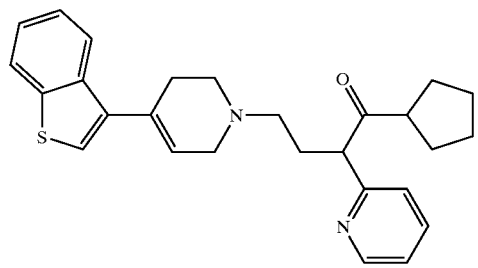

The title compound can be prepared in a manner analogous to the procedure described in example 4 from 4-(3-benzo(b)thiophene)-1,2,3,6-tetrahydropyridyl and 1-cyclopentyl-2-(2-pyridyl)butan-1-one-4-al.

EXAMPLE 32

Preparation of 4-(3-benzo(b)thiophene-piperidine)-1-cyclohexyl-2-(2-pyridyl)butan-1-one

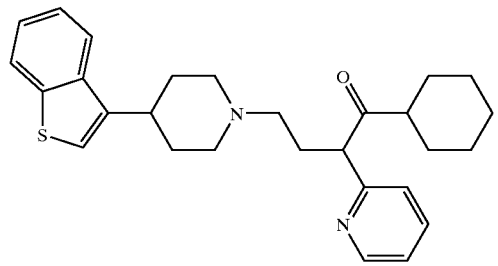

Preparation of 3-benzo(b)thiophene-piperidine.

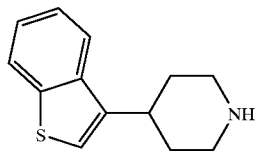

Scheme I, step E: 4-(3-benzo(b)thiophene)-1,2,3,6-tetrahydropyridyl (3.5 mmol) is dissolved in ethanol (25 mL). 10% Palladium on carbon (2.25 g) is added and the reaction is stirred under hydrogen at 60 psi at room temperature overnight. The reaction mixture is filtered and the filtrate is concentrated to provide 3-benzo(b)thiophene-piperidine.

Preparation of Final Title Compound.

Scheme IV, step A; 1-cyclohexyl-2-(2-pyridyl)butan-1-one-4-al (0.20 g, 0.83 mmol, prepared in Example 1) is combined with 3-benzo(b)thiophene-piperidine (0.60 mmol) in methylene chloride (10 mL) with acetic acid (0.09 mL, 1.5 mmol) and sodium triacetoxyborohydride (0.17 g, 0.78 mmol). The reaction mixture is stirred at room temperature overnight. It is then made basic with 1N sodium hydroxide and extracted with methylene chloride. The organic extract is dried over anhydrous sodium sulfate, filtered and concentrated under vacuum. The residue can then be purified by flash chromatography (2% methanol/ethyl acetate, silica gel) to provide the final title compound.

EXAMPLE 33

Preparation of 4-(3-benzo(b)thiophene-1,2,3,6-tetrahydropyridyl)-1-cyclohexyl-2-(2-pyridyl)butane.

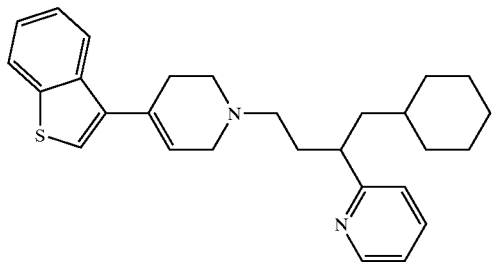

The title compound can be prepared in a manner analogous to the procedure described in example 6 from 4-(3-benzo(b)thiophene)-1,2,3,6-tetrahydropyridyl and 4-cyclohexyl-3-(2-pyridyl)-butyraldehyde.

EXAMPLE 34

Preparation of 4-(3-benzo(b)thiophene-1,2,3,6-tetrahydropyridyl)-1-cyclohexyl-2-methyl-2-phenyl-butan-1-one.

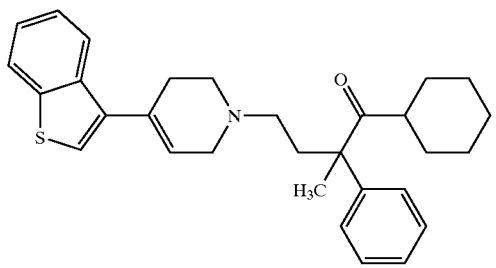

The title compound can be prepared in a manner analogous to the procedure described in example 7 from 4-(3-benzo(b)thiophene)-1,2,3,6-tetrahydropyridyl and 4-cyclohexyl-3-methyl-4-oxo-3-phenylbutyraldehyde.

EXAMPLE 35

Preparation of 4-(3-benzo(b)thiophene-1,2,3,6-tetrahydropyridyl)-1-cyclohexyl-2-methyl-2-(2-pyridyl)-butan-1-one.

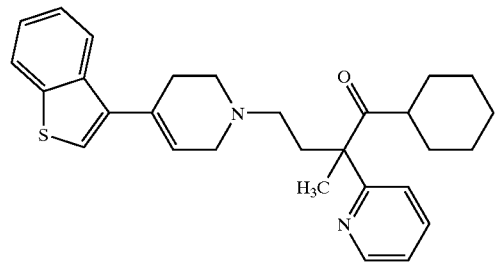

The title compound can be prepared in a manner analogous to the procedure described in example 8 from 4-(3-benzo(b)thiophene)-1,2,3,6-tetrahydropyridyl and 4-cyclohexyl-3-methyl-4-oxo-3-(2-pyridyl)butyraldehyde.

EXAMPLE 36

Preparation of:

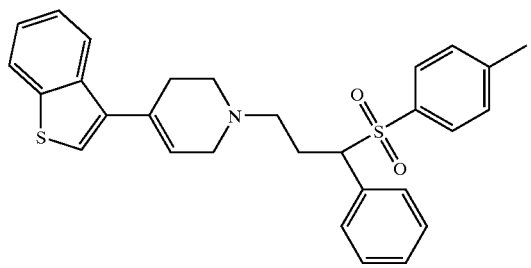

The title compound can be prepared in a manner analogous to the procedure described in example 9 from 4-(3-benzo(b)thiophene)-1,2,3,6-tetrahydropyridyl and aldehyde:

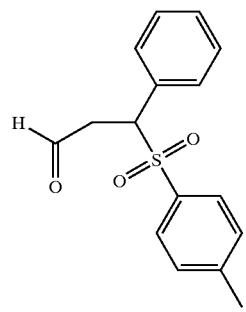

Table 1 discloses various benzofuran derivatives that are included within the scope of the present invention. Such benzofurans can be readily prepared by one of ordinary skill in the art, for example, in a manner analogous to the procedures described hereinabove.

TABLE I

| Example | Compound |
|---------|----------|
| 37 | |
| 38 | |
| 39 | |
| 40 | |
| 41 | |
| 42 | |

TABLE I-continued
| Example | Compound |
|---|---|
| 43 | 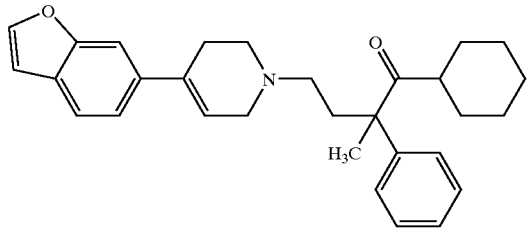 |
| 44 | 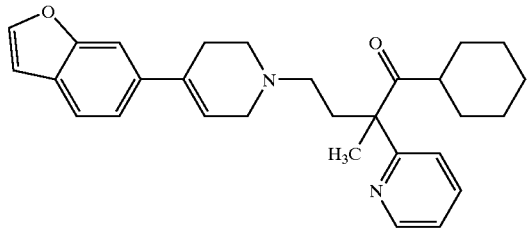 |
| 45 | 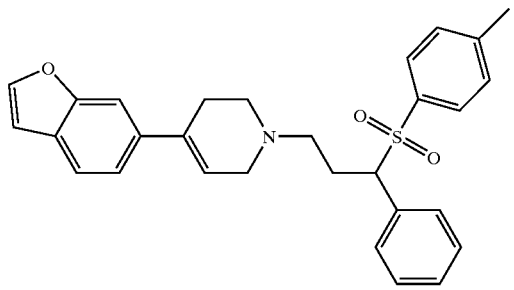 |
| 46 | 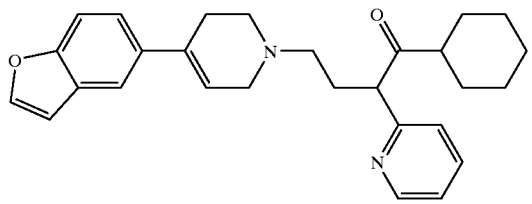 |
| 47 | 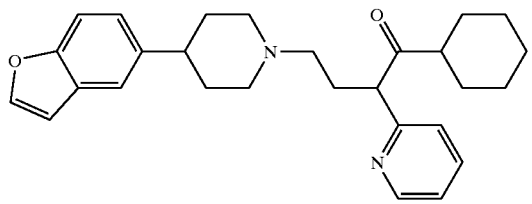 |
| 48 | 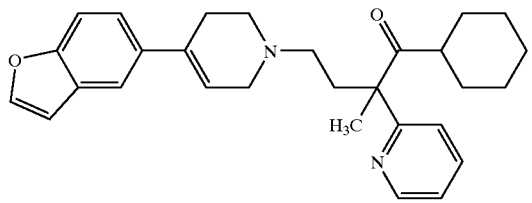 |

TABLE I-continued
| Example | Compound |
|---|---|
| 49 | 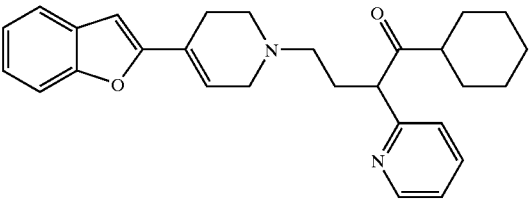 |
| 50 | 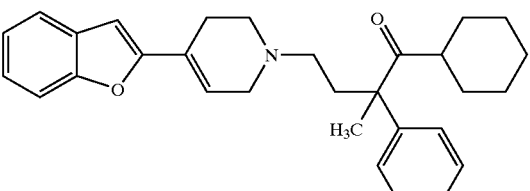 |
| 51 | 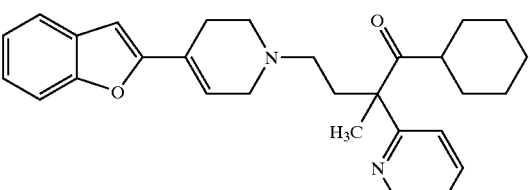 |
| 52 | 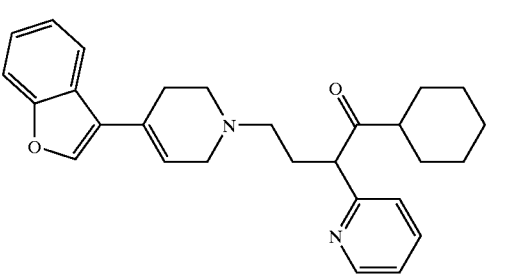 |
| 53 | 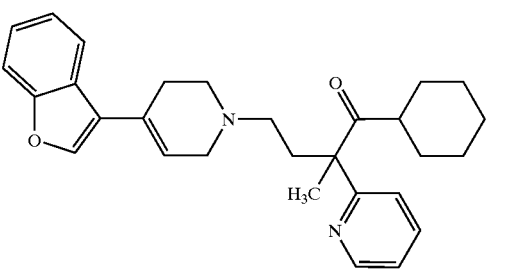 |
| 54 | 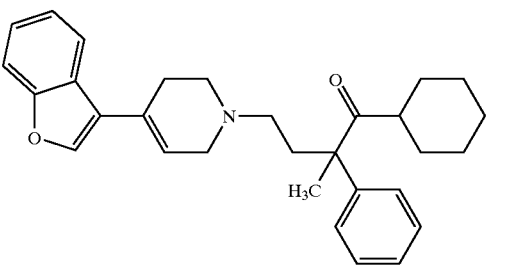 |

TABLE I-continued

| Example | Compound |
| --- | --- |
| 55 | 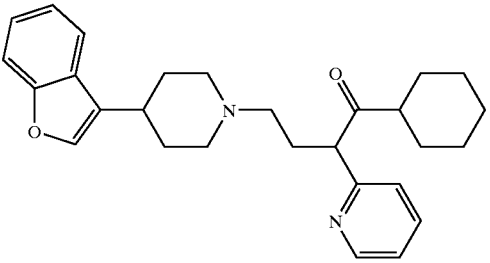 |

The compounds of formulas IIb and IIc are active at the serotonin-$1_A$ receptor and at the serotonin-$2_A$ receptor, particularly as antagonists and as partial agonists at that receptor. In addition, compounds of formula IIa are active at the serotonin-$1_A$ receptor, at the serotonin-$2_A$ receptor, and at the serotonin-1D receptor. The compounds of formula IId are active at the serotonin-1A receptor.

The 5-$HT_{1A}$ receptor binding potency, the 5-$HT_{2A}$ receptor binding potency and the 5-HT1D receptor binding potency of the present compounds are measured by techniques well known in the art. For example, the 5-$HT_{1A}$ receptor binding potency is measured by a modification of the binding assay described by Taylor, et al. (J. Pharmacol. Exp. Ther. 236, 118–125, 1986); and Wong, et al., Pharm. Biochem. Behav. 46, 173–77 (1993). Membranes for the binding assay are prepared from male Sprague-Dawley rats (150–250 g). The animals are killed by decapitation, and the brains are rapidly chilled and dissected to obtain the hippocampi. Membranes from the hippocampi are either prepared that day, or the hippocampi are stored frozen (–70° C.) until the day of preparation. The membranes are prepared by homogenizing the tissue in 40 volumes of ice-cold Tris-HCl buffer (50 mM, pH 7.4 at 22° C.) using a homogenizer for 15 sec., and the homogenate is centrifuged at 39800×g for 10 min. The resulting pellet is then resuspended in the same buffer, and the centrifugation and resuspension process is repeated three additional times to wash the membranes. Between the second and third washes the resuspended membranes are incubated for 10 min. at 370 to facilitate the removal of endogenous ligands. The final pellet is resuspended in 67 mM Tris-HCl, pH 7.4, to a concentration of 2 mg of tissue original wet weight/200 μL. This homogenate is stored frozen (–70° C.) until the day of the binding assay. Each tube for the binding assay has a final volume of 800 μL and contains the following: Tris-HCl (50 mM), pargyline (10 μM), $CaCl_2$ (3 mM), [$^3$H]8-OH-DPAT (1.0 nM), appropriate dilutions of the drugs of interest, and membrane resuspension equivalent to 2 mg of original tissue wet weight, for a final pH of 7.4. The assay tubes are incubated for either 10 min. or 15 min. at 37° C., and the contents are then rapidly filtered through GF/B filters (pretreated with 0.5% polyethylenimine), followed by four one-mL washes with ice-cold buffer. The radioactivity trapped by the filters is quantitated by liquid scintillation spectrometry, and specific [3H]8-OH-DPAT binding to the 5-$HT_{1A}$ sites is defined as the difference between [3H]8-OH-DPAT bound in the presence and absence of 10 μM 5-HT.

$IC_{50}$ values, i.e., the concentration required to-inhibit 50% of the binding, are determined from 12-point competition curves using nonlinear regression (SYSTAT, SYSTAT, Inc., Evanston, Ill.). $IC_{56}$ values are converted to $K_i$ values using the ChengPrusoff equation (Biochem. Pharmacol., 22, 3099–3108 (1973).

Additional binding assays of some of the present compounds are carried out by an assay method which uses a cloned cell line which expresses the serotonin-1A receptor, rather than the hippocampal membranes. Such cloned cell lines have been described by Fargin, et al., J. Bio. Chem., 264, 14848–14852 (1989), Aune, et al., J. Immunology, 151, 1175–1183 (1993), and Raymond, et al., Naunyn-Schmiedeberg's Arch. Pharmacol., 346, 127–137 (1992). Results from the cell line assay are substantially in agreement with results from the hippocampal membrane assay.

As was reported by R. L. Weinshank, et al., WO93/14201, the 5-$HT_{1A}$ receptor is functionally coupled to a G-protein as measured by the ability of serotonin and serotonergic drugs to inhibit forskolin stimulated cAMP production in NIH3T3 cells transfected with the 5-$HT_{1A}$ receptor. Adenylate cyclase activity is determined using standard techniques. A maximal effect is achieved by serotonin. An Emax is determined by dividing the inhibition of a test compound by the maximal effect and determining a percent inhibition. (N. Adham, et al., supra,; R. L. Weinshank, et al., Proceedings of the National Academy of Sciences (USA), 89, 3630–3634 (1992), and the references cited therein.)

[$^{35}$S]GTPγS Binding Method

Agonist activation of G protein-coupled receptors results in the release of GDP (guanosine-5'-diphosphate) from the γ-subunit of the G protein and the subsequent binding of GTP (guanosine-5'-triphosphate). The binding of the stable analogue [S]GTPγS (guanosine 5'-O-[3-thiotriphosphate]) can be used as an indicator of this receptor activation (see Wieland, T., Jakobs, K. H., 1994. Measurement of receptor-stimulated guanosine 5'-O-(γ-thio)triphosphate binding by G proteins. Methods Enzymol. 237, 3–13.). $EC_{50}$ and efficacy ($E_{max}$) values can be determined. Similarly, antagonists will inhibit agonist-stimulated [$^{35}$S]GTPγS binding. From these experiments, $IC_{50}$ values, converted to a dissociation constant, e.g. $K_i$, and efficacy ($E_{max}$) values can be determined by one of ordinary skill in the art.

Measurement of cAMP Formation

Transfected NIH3T3 cells (estimated $B_{max}$ from one point competition studies=488 fmol/mg of protein) are incubated in DMEM, 5 mM theophylline, 10 mM HEPES (4-[2-hydroxyethyl]-1-piperazineethanesulfonic acid) and 10 μM pargyline for 20 minutes at 37° C., 5% carbon dioxide. Drug dose-effect curves are then conducted by adding 6 different final concentrations of drug, followed immediately by the addition of forskolin (10 mM). Subsequently, the cells are incubated for an additional 10 minutes at 37° C., 5% carbon dioxide. The medium is aspirated and the reaction is stopped by the addition of 100 mM hydrochloric acid. To demonstrate competitive antagonism, a dose-response curve for 5-HT is measured in parallel, using a fixed dose of methiothepin (0.32 mM). The plates are stored at 4° C. for 15 minutes and then centrifuged for 5 minutes at 500×g to pellet cellular debris, and the supernatant is aliquoted and stored at −20° C. before assessment of cAMP formation by radioimmunoassay (cAMP radioimmunoassay kit; Advanced Magnetics, Cambridge, Mass.). Radioactivity is quantified using a Packard COBRA Auto Gamma counter, equipped with data reduction software. Representative compounds are tested for 5-$HT_{1A}$ receptor antagonist activity in the cAMP assay.

5$HT_{1A}$ Antagonist, In Vivo Tests a) 5-$HT_{1A}$ Antagonism Subcutaneous Test Compounds ware tested over a range of subcutaneous doses for activity in blocking the 8-OH-DPAT induced behaviors and hypothermia. Lower lip retraction (LLR) and flat body posture (FBP) are recorded in male Sprague Dawley rats (~250 grams from Harlan Sprague Dawley). Both LLR and FBP are measured on a scale of 0–3 (Wolff et al, 1997). In the LLR behavioral assay, "0" indicates normal lip position; "1" indicates a slight separation of the lips; "2" indicates that the lips are open with some teeth visible; "3" indicates that the lips are fully open with all the front teeth exposed. In the FBP assay, a score of "0" indicates normal body posture; "1" indicates that the stomach is on the floor with the back in its normal rounded position; "2" indicates that the stomach is on the floor with the back straightened and rising from the shoulders to the hips; "3" indicates that the stomach is pressed onto the floor and the back is flattened with the shoulders and hips even. Core body temperature is recorded by rectal probe inserted 5.0 cm immediately after the behavioral measures. Rats are injected subcutaneous with a compound (at 0, 0.3, 1.0 and 3.0 mg/kg) 35 minutes before scoring and the 8-OH-DPAT (0.1 mg/kg subcutaneous) is injected 20 minutes before scoring.

b) 5-$HT_{1a}$ Agonist Subcutaneous Test

The compounds are also tested at a high dose of 10 mg/kg subcutaneous alone to see if they induced 5-$HT_{1a}$ agonist-like hypothermia.

The efficacy of the compounds of the invention to inhibit the reuptake of serotonin is determined by a paroxetine binding assay, the usefulness of which is set out by Wong, et al., *Neuropsychopharmacology*, 8, 23–33 (1993). Synaptosomal preparations from rat cerebral cortex are made from the brains of 100–150 g Sprague-Dawley rats which are killed by decapitation. The cerebral cortex is homogenized in 9 volumes of a medium containing 0.32 M sucrose and 20 $\mu$M glucose. The preparations are resuspended after centrifugation by homogenizing in 50 volumes of cold reaction medium (50 $\mu$M sodium chloride, 50 $\mu$M potassium chloride, pH 7.4) and centrifuging at 50,000 g for 10 minutes. The process is repeated two times with a 10-minute incubation at 37° C. between the second and third washes. The resulting pellet is stored at −70° C. until use. Binding of $^3$H-paroxetine to 5-HT uptake sites is carried out in 2 mL reaction medium containing the appropriate drug concentration, 0.1 nM $^3$H-paroxetine, and the cerebral cortical membrane (50 $\mu$g protein/tube). Samples are incubated at 37° C. for 30 minutes; those containing 1 $\mu$M fluoxetine are used to determine nonspecific binding of $^3$H-paroxetine. After incubation, the tubes are filtered through Whatman GF/B filters, which are soaked in 0.05% polyethylenimine for 1 hour before use, using a cell harvester by adding about 4 mL cold Tris buffer (pH 7.4), aspirating, and rinsing the tubes three additional times. Filters are then placed in scintillation vials containing 10 mL scintillation fluid, and the radioactivity is measured by liquid scintillation spectrophotometry.

The pharmacological activities which have been described immediately above provide the mechanistic basis for the pharmaceutical utility of the compounds described in this document. A number of pharmaceutical utilities will be described below.

Throughout this document, the person or animal to be treated will be described as the "subject", and it will be understood that the most preferred subject is a human. However, it must be noted that the study of adverse conditions of the central nervous system in non-human animals is only now beginning, and that some instances of such treatments are coming into use. For example, fluoxetine, and perhaps other serotonin reuptake inhibitors, are being used in companion animals such as dogs for the treatment of behavioral problems and the like. Accordingly, use of the present compounds in non-human animals is contemplated.

It will be understood that the dosage ranges for other animals will necessarily be quite different from the doses administered to humans, and accordingly that the dosage ranges described below in the section on tobacco withdrawal must be recalculated. For example, a small dog may be only 1/10th of a typical human's size, and it will therefore be necessary for a much smaller dose to be used. The determination of an effective amount for a certain non-human animal is carried out in the same manner described below in the case of humans, and veterinarians are well accustomed to such determinations.

The activity of the compounds at the serotonin-1A receptor provides a method of affecting the serotonin-1A receptor which comprises administering to a subject in need of such treatment an effective amount of a compound of formula I. Reasons for the necessity of affecting the serotonin-1A receptor will be described in detail below, but in all cases the effect on the serotonin-1A receptor is brought about through the compounds' potency as antagonists or partial agonists at that receptor. A subject in need of a modification of the effects of the 5-$HT_{1A}$ receptor is one having one or more of the specific conditions and problems to be further described, or a condition or problem not yet recognized as created by an imbalance or malfunction of the 5-$HT_{1A}$ receptor, since research on the central nervous system is presently ongoing in many fields and newly discovered relationships between receptors and therapeutic needs are continually being discovered.

An effective amount of a compound for affecting the serotonin-1A receptor is the amount, or dose, of the compound which provides the desired effect in the subject under diagnosis or treatment. The effective amount of compound to be administered, in general, is from about 1 to about 200 mg/day; as usual, the daily dose may be administered in a single bolus, or in divided doses, depending on the judgment of the physician in charge of the case. A more preferred range of doses is from about 5 to about 100 mg/day; other dosage ranges which may be preferred in certain circumstances are from about 10 to about 50 mg/day; from about 5 to about 50 mg/day; from about 10 to about 25 mg/day; and a particularly preferred range is from about 20 to about 25 mg/day.

The amount is an individualized determination, and physicians are well accustomed to adjusting effective amounts of pharmaceuticals based on observations of the subject. The effective amount of the present compounds is discussed in some detail below, in the discussion about the treatment of tobacco withdrawal symptoms, and that discussion is applicable, in an analogous manner to the determination of the effective amount in all treatment methods.

In a manner analogous to the above, the activity of the compounds at the serotonin-2A receptor provides a method of affecting the serotonin-2A receptor which comprises administering to a subject in need of such treatment an effective amount of a compound of formula I.

In a manner analogous to the above, the activity of the compounds at the serotonin-1D receptor provides a method of affecting the serotonin-1D receptor which comprises administering to a subject in need of such treatment an effective amount of a compound of formula I.

Further, the activity of compounds of formula I in the inhibition of the reuptake of serotonin provides a method of inhibiting the reuptake of serotonin comprising administering to a subject in need of such treatment an effective amount of a compound of that formula. An effective amount of a compound for inhibiting the reuptake of serotonin is the amount, or dose, of the compound which provides the desired effect in the subject under diagnosis or treatment. The amount is an individualized determination, and physicians are well accustomed to adjusting effective amounts of pharmaceuticals based on observations of the subject. It is now known that numerous physiological and therapeutic benefits are obtained through the administration of drugs which inhibit the reuptake of serotonin. The treatment of depression with drugs of the class of which fluoxetine is the leader has become perhaps the greatest medical breakthrough of the past decade. Numerous other treatment methods carried out by the administration of the compounds of formula I will be set out in detail below. Again, the effective amount of a compound for the inhibition of serotonin reuptake, or for a specific therapeutic method which depends on the inhibition of reuptake, is determined in the manner analogous to that described below under the heading of smoking withdrawal.

The unique combination of $5-HT_{1A}$ receptor activity, $5-HT_{2A}$ receptor activity, and serotonin reuptake inhibition possessed by the compounds of the invention afford a method of providing to a subject both physiological activities with a single administration of a compound of that formula. It is believed that the compounds of formulas IIb and IIc are advantageous in that they provide all three physiological effects in a single drug.

The unique combination of $5-HT_{2A}$ receptor activity and serotonin reuptake inhibition possessed by the compounds of formula IId afford a method of providing to a subject both physiological activities with a single administration of a compound of that formula. It is believed that the compounds of formula IId are advantageous in that they provide both physiological effects in a single drug.

The unique combination of $5-HT_{1A}$ receptor activity, $5-HT_{2A}$ receptor activity, 5-HT1D receptor activity, and serotonin reuptake inhibition possessed by the compounds of formula IIa afford a method of providing to a subject both physiological activities with a single administration of a compound of that formula. It is believed that the compounds of formula Ia are advantageous in that they provide all three physiological effects in a single drug.

It is presently believed that the result of administration of a compound of formula I is to provide physiological and therapeutic treatment methods which are typical of those provided by presently known serotonin reuptake inhibitors, but with enhanced efficacy, quicker onset of action and reduced side effects.

The activities of compounds of formula I at the $5-HT_{1A}$ receptor, the $5-HT_{2A}$ receptor, the $5-HT_{1D}$ receptor, and in reuptake inhibition are of comparable potencies, so a single effective amount as defined hereinabove for affecting the serotonin-1A receptor, the serotonin-2A receptor, the serotonin-1D receptor, or for inhibiting the reuptake of serotonin, is effective for affecting the serotonin-1A receptor the serotonin-2A receptor, the serotonin-1D receptor, and for inhibiting the reuptake of serotonin in a subject.

Tobacco or Nicotine Withdrawal

It is well known that the chronic administration of nicotine results in tolerance and, eventually, dependence. The use of tobacco has become extremely widespread in all countries, despite the well known adverse effects of the use of tobacco in all its forms. Thus, it is clear that tobacco use is extremely habit-forming, if not addictive, and that its use provides sensations to the user which are pleasant and welcome, even though the user may be fully aware of the drastic long term ill effects of its use.

Rather recently, vigorous campaigns against the use of tobacco have taken place, and it is now common knowledge that the cessation of smoking brings with it numerous unpleasant withdrawal symptoms, which include irritability, anxiety, restlessness, lack of concentration, lightheadedness, insomnia, tremor, increased hunger and weight gain, and, of course, a craving for tobacco.

At the present time, probably the most widely used therapy to assist the cessation of tobacco use is nicotine replacement, by the use of nicotine chewing gum or nicotine-providing transdermal patches. It is widely known, however, that nicotine replacement is less effective without habit-modifying psychological treatment and training.

Thus, the present method of preventing or alleviating the symptoms caused by withdrawal or partial withdrawal from the use of tobacco or of nicotine comprises the administration of an effective amount of one of a compound of formula I to the subject. The method of the present invention is broadly useful in assisting persons who want to cease or reduce their use of tobacco or nicotine. Most commonly, the form of tobacco use is smoking, most commonly the smoking of cigarettes. The present invention is also helpful, however, in assisting in breaking the habit of all types of tobacco smoking, as well as the use of snuff, chewing tobacco, etc. The present method is also helpful to those who have replaced or partially replaced, their use of tobacco with the use of nicotine replacement therapy. Thus, such subjects can be assisted to reduce and even eliminate entirely their dependence on nicotine in all forms.

A particular benefit of therapy with the present compounds is the elimination or reduction of the weight gain which very often results from reducing or withdrawing from use of tobacco or nicotine.

It will be understood that the present invention is useful for preventing or alleviating the withdrawal symptoms which afflict subjects who are trying to eliminate or reduce their use of tobacco or nicotine. The common withdrawal symptoms of such people include, at least, irritability, anxiety, restlessness, lack of concentration, insomnia, nervous tremor, increased hunger and weight gain, lightheadedness, and the craving for tobacco or nicotine. The prevention or alleviation of such symptoms, when they are caused by or occur in conjunction with ceasing or reducing the subject's use of tobacco or nicotine is a desired result of the present invention and an important aspect of it.

The invention is carried out by administering an effective amount of a compound of formula I to a subject who is in need of or carrying out a reduction or cessation of tobacco or nicotine use.

It will be understood that the effective amount for a given subject is always to be set by the judgment of the attending physician, and that the dose is subject to modification based on the size of the subject, the lean or fat nature of the subject, the characteristics of the particular compound chosen, the in tensity of the subject's tobacco habit, the intensity of the subject's withdrawal symptoms, and psychological factors which may affect the subject's physiological responses. Thus, the effective amount is the amount required to prevent or alleviate the symptoms of withdrawal or partial withdrawal in the subject under treatment.

In effecting treatment of a subject as described herein, a compound of formula I can be administered in any form or mode which makes the compound bioavailable in effective amounts, including oral and parenteral routes. For example, compounds of formula I can be admininstered orally, subcutaneously, intramuscularly, intravenously, transdermally, intranasally, rectally, and the like. Oral administration is the preferred route for compounds of formula I.

The effect of compounds in alleviating the symptoms of nicotine withdrawal is evaluated in rats by an auditory startle test, which is carried out as follows.

Procedures for Nicotine Withdrawal Studies

Animals: Male Long Evans rats are individually housed in a controlled environment on a 12 hour light-dark cycle and are given free access to food (Purina Rodent Chow) and water. All treatment groups contain 8–10 rats.

Chronic Nicotine Treatment: Rats are anesthetized with halothane and Alzet osmotic minipumps (Alza Corporation, Palo Alto, Calif., Model 2ML2) are implanted subcutaneously. Nicotine ditartrate is dissolved in physiological saline. Pumps are filled with either nicotine ditartrate (6 mg/kg base/day) or physiological saline. Twelve days following implantation of pumps, rats are anesthetized with halothane and the pumps are removed.

Auditory Startle Response: The sensory motor reactions [auditory startle response (peak amplitude Vmax)] of individual rats is recorded using San Diego Instruments startle chambers (San Diego, Calif.). Startle sessions consist of a 5-minute adaptation period at a background noise level of 70±3 dBA immediately followed by 25 presentations of auditory stimuli (120±2 dBA noise, 50 ms duration) presented at 8-second intervals. Peak startle amplitudes are then averaged for all 25 presentations of stimuli for each session. Auditory startle responding is evaluated daily at 24 hour intervals on days 1–4 following nicotine withdrawal.

Combination with Reuptake Inhibitors

A further application of the compounds of formula I is their use in combination with a serotonin reuptake inhibitor to potentiate the action of those drugs by increasing the availability of serotonin, as well as norepinephrine and dopamine, in the brain of patients to whom the drug combination is administered. Typical and appropriate reuptake inhibitors (SRI) are fluoxetine, duloxetine, venlafaxine, milnacipran, citalopram, fluvoxamine and paroxetine. Accordingly, the present invention provides a method for potentiating the action of a serotonin reuptake inhibitor, particularly one of the group consisting of fluoxetine, duloxetine, venlafaxine, milnacipran, citalopram, fluvoxamine and paroxetine, in increasing the availability of serotonin, norepinephrine and dopamine in the brain, comprising administering said serotonin reuptake inhibitor in combination with a compound of formula I. The invention also provides pharmaceutical compositions which comprise a serotonin reuptake inhibitor in combination with a compound of formula I, and a method of treating a pathological condition which is created by or is dependent upon decreased availability of serotonin, dopamine or norepinephrine, which method comprises administering the same adjunctive therapy to a patient in need of such treatment.

It will be understood that, while the compounds of formula I individually provide serotonin reuptake inhibition, it is entirely possible to administer a compound of formula I in combination with a conventional serotonin reuptake inhibitor in order to obtain still further enhanced results in potentiating serotonin reuptake inhibition. Examples of representative serotonin reuptake inhibitors include but are not limited to the following:

Fluoxetine, N-methyl-3-(p-trifluoromethylphenoxy)-3-phenylpropylamine, is marketed in the hydrochloride salt form, and as the racemic mixture of its two enantiomers. U.S. Pat. No. 4,314,081 is an early reference on the compound. Robertson, et al., *J. Med. Chem.* 31, 1412 (1988), taught the separation of the R and S enantiomers of fluoxetine and showed that their activity as serotonin uptake inhibitors is similar to each other. In this document, the word "fluoxetine" will be used to mean any acid addition salt or the free base, and to include either the racemic mixture or either of the R and S enantiomers.

Duloxetine, N-methyl-3-(1-naphthalenyloxy)-3-(2-thienyl)propanamine, is usually administered as the hydrochloride salt and as the (+) enantiomer. It was first taught by U.S. Pat. No. 4,956,388, which shows its high potency. The word "duloxetine" will be used here to refer to any acid addition salt or the free base of the molecule.

Venlafaxine is known in the literature, and its method of synthesis and its activity as an inhibitor of serotonin and norepinephrine uptake are taught by U.S. Pat. No. 4,761, 501. Venlataxine is identified as compound A in that patent.

Milnacipran (N,N-diethyl-2-aminomethyl-1-phenylcyclopropanecarboxamide) is taught by U.S. Pat. No. 4,478,836, which prepared milnacipran as its Example 4. The patent describes its compounds as antidepressants. Moret, et al., *Neuropharmacology* 24, 1211–19 (1985), describe its pharmacological activities.

Citalopram, 1-[3-(dimethylamino)propyl]-1-(4-fluorophenyl)-1,3-dihydro-5-isobenzofurancarbonitrile, is disclosed in U.S. Pat. No. 4,136,193 as a serotonin reuptake inhibitor. Its pharmacology was disclosed by Christensen, et al., *Eur. J. Pharmacol.* 41, 153 (1977), and reports of its clinical effectiveness in depression may be found in Dufour, et al., *Int. Clin. Psychopharmacol.* 2, 225 (1987), and Timmerman, et al., ibid., 239.

Fluvoxamine, 5-methoxy-1-[4-(trifluoromethyl)phenyl]-1-pentanone O-(2-aminoethyl)oxime, is taught by U.S. Pat. No. 4,085,225. Scientific articles about the drug have been published by Claassen, et al., *Brit. J. Pharmacol.* 60, 505 (1977); and De Wilde, et al., *J. Affective Disord.* 4, 249 (1982); and Benfield, et al., *Drugs* 32, 313 (1986).

Sertraline, 1-(3,4-dichlorophenyl)-4-methylaminotetralin, is disclosed in U.S. Pat. No. 4,536,518.

Paroxetine, trans-(−)-3-[(1,3-benzodioxol-5-yloxy) methyl]-4-(4-fluorophenyl)piperidine, may be found in U.S. Pat. Nos. 3,912,743 and 4,007,196. Reports of the drug's activity are in Lassen, *Eur. J. Pharmacol.* 47, 351 (1978); Hassan, et al., *Brit. J. Clin. Pharmacol.* 19, 705 (1985); Laursen, et al., *Acta Psychiat. Scand.* 71, 249 (1985); and Battegay, et al., *Neuroisychobiology* 13, 31 (1985).

All of the U.S. patents which have been mentioned above in connection with compounds used in the present invention are incorporated herein by reference.

Fluoxetine or duloxetine are the preferred SRI's in pharmaceutical compositions combining a compound of formula I and an SRI, and the corresponding methods of treatment.

It will be understood by the skilled reader that all of the compounds used in the present invention are capable of forming salts, and that the salt forms of pharmaceuticals are commonly used, often because they are more readily crystallized and purified than are the free bases. In all cases, the use of the pharmaceuticals described above as salts is contemplated in the description herein, and often is preferred, and the pharmaceutically acceptable salts of all of the compounds are included in the names of them.

The dosages of the drugs used in the present combination must, in the final analysis, be set by the physician in charge of the case, using knowledge of the drugs, the properties of the drugs in combination as determined in clinical trials, and the characteristics of the subject, including diseases other than that for which the physician is treating the subject. General outlines of the dosages, and some preferred human dosages, can and will be provided here. Dosage guidelines for some of the drugs will first be given separately; in order to create a guideline for any desired combination, one would choose the guidelines for each of the component drugs.

Fluoxetine: from about 1 to about 80 mg, once/day; preferred, from about 10 to about 40 mg once/day; preferred for bulimia and obsessive-compulsive disease, from about 20 to about 80 mg once/day;

Duloxetine: from about 1 to about 30 mg once/day; preferred, from about to about 20 mg once/day;

Venlafaxine: from about 10 to about 150 mg once-thrice/day; preferred, from about 25 to about 125 mg thrice/day;

Milnacipran: from about 10 to about 100 mg or ice-twice/day; preferred, from about 25 to about 50 mg twice/day;

Citalopram: from about 5 to about 50 mg once/day; preferred, from about 10 to about 30 mg once/day;

Fluvoxamine: from about 20 to about 500 mg once/day; preferred, from about 50 to about 300 mg once/day;

Paroxetine from about 5 to about 100 mg once/day; preferred, from about 50 to about 300 mg once/day.

In more general terms one would create a combination of the present invention by choosing a dosage of SRI according to the spirit of the above guideline, and choosing a dosage of the compound of formula I in the ranges taught above.

The adjunctive therapy of the present invention is carried out by administering a SRI together with a compound of formula I in any manner which provides effective levels of the two compounds in the body at the same time. All of the compounds concerned are orally available and are normally administered orally, and so oral administration of the adjunctive combination is preferred. They may be administered together, in a single dosage form, or may be administered separately.

However, oral administration is not the only route or even the only preferred route. For example, transdermal administration may be very desirable for patients who are forgetful or petulant about taking oral medicine. One of the drugs may be administered by one route, such as oral, and the other may be administered by the transdermal, percutaneous, intravenous, intramuscular, intranasal or intrarectal route, in particular circumstances. The route of administration may be varied in any way, limited by the physical properties of the drugs and the convenience of the patient and the care giver.

It is particularly preferred, however, for the adjunctive combination to be administered as a single pharmaceutical composition, and so pharmaceutical compositions incorporating both a SRI and a compound of formula I are important embodiments of the present invention. Such compositions may take any physical form which is pharmaceutically acceptable, but orally usable pharmaceutical compositions are particularly preferred. Such adjunctive pharmaceutical compositions contain an effective amount of each of the compounds, which effective amount is related to the daily dose of the compounds to be administered. Each adjunctive dosage unit may contain the daily doses of both compounds, or may contain a traction of the daily doses, such as one-third of the doses. Alternatively, each dosage unit may contain the entire dose of one of the compounds, and a fraction of the dose of the other compound. In such case, the patient would daily take one of the combination dosage units, and one or more units containing only the other compound. The amounts of each drug to be contained in each dosage unit depends on the identity of the drugs chosen for the therapy, and other factors such as the indication for which the adjunctive therapy is being given.

As stated above, the benefit of the adjunctive therapy .is its ability to augment the increase in availability of serotonin, norepinephrine and dopamine caused by the SRI compounds, resulting in improved activity in treating the various conditions described below in detail. The increase in availability of serotonin is particularly important and is a preferred aspect of the invention. Further, the invention provides a more rapid onset of action than is usually provided by treatment with the SRI alone.

Preferred pathological conditions to be treated by the methods disclosed herein include depression, bulimia, obsessive-compulsive disease and obesity. Another preferred condition more specific to combinations including preferably duloxetine but also venlafaxine and milnacipran is urinary incontinence.

Depression in its many variations has recently become much more visible to the general public than it has previously been. It is now recognized as an extremely damaging disorder, and one that afflicts a surprisingly large fraction of the human population. Suicide is the most extreme symptom of depression, but millions of people, not quite so drastically afflicted, live in misery and partial or complete uselessness, and afflict their families as well by their affliction. The introduction of fluoxetine was a breakthrough in the treatment of depression, and depressives are now much more likely to be diagnosed and treated than they were only a decade ago. Duloxetine is in clinical trials for the treatment of depression and is likely to become a marketed drug for the purpose.

Depression is often associated with other diseases and conditions, or caused by such other conditions. For example, it is associated with Parkinson's disease; with HIV; with Alzheimer's disease; and with abuse of anabolic steroids. Depression may also be associated with abuse of any substance, or may be associated with behavioral problems resulting from or occurring in combination with head injuries, mental retardation or stroke. Depression in all its variations is a preferred target of treatment with the present adjunctive therapy method and compositions.

Obsessive-compulsive disease appears in a great variety of degrees and symptoms, generally linked by the victim's uncontrollable urge to perform needless, ritualistic acts. Acts of acquiring, ordering, cleansing and the like, beyond any rational need or rationale, are the outward characteristic of the disease. A badly afflicted subject may be unable to do anything but carry out the rituals required by the disease. Fluoxetine is approved in the United States and other countries for the treatment of obsessive-compulsive disease and has been found to be effective.

Obesity is a frequent condition in the American population. It has been found that fluoxetine will enable an obese subject to lose weight, with the resulting benefit to the circulation and heart condition, as well as general well being and energy.

Urinary incontinence is classified generally as stress or urge incontinence, depending on whether its root cause is the inability of the sphincter muscles to keep control, or the overactivity of the bladder muscles. Duloxetine controls both types of incontinence, or both types at once, and so is important to the many who suffer from this embarrassing and disabling disorder.

The present treatment methods are useful for treating many other diseases, disorders and conditions as well, as set out below. In many cases, the diseases to be mentioned here are classified in the International Classification of Diseases, 9th Edition (ICD), or in the Diagnostic and Statistical Manual of Mental Disorders, 3rd Version Revised, published by the American Psychiatric Association (DSM). In such cases, the ICD or DSM code numbers are supplied below for the convenience of the reader.

depression, ICD 296.2 & 296.3, DSM 296, 294.80, 293.81, 293.82, 293.83, 310.10, 318.00, 317.00 migraine pain, particularly neuropathic pain bulimia, ICD 307.51, DSM 307.51 premenstrual syndrome or late luteal phase syndrome, DSM 307.90 alcoholism, ICD 305.0, DSM 305.00 & 303.90 tobacco abuse, ICD 305.1, DSM 305.10 & 292.00 panic disorder, ICD 300.01, DSM 300.01 & 300.21 anxiety, ICD 300.02, DSM 300.00 post-traumatic syndrome, DSM 309.89 memory loss, DSM 294.00 dementia of aging, ICD 290 social phobia, ICD 300.23, DSM 300.23 attention deficit hyperactivity disorder, ICD 314.0 disruptive behavior disorders, ICD 312 impulse control disorders, ICD 312, DSM 312.39 & 312.34 borderline personality disorder, ICD 301.83, DSM 301.83 chronic fatigue syndrome premature ejaculation, DSM 302.75 erectile difficulty, DSM 302.72 anorexia nervosa, ICD 307.1, DSM 307.10 disorders of sleep, ICD 307.4 autism mutism trichotillomania

Further, the compounds of formula I are useful for alleviating the symptoms of smoking cessation or nicotine withdrawal when administered alone or in combination with a serotonin reuptake inhibitor. The SRI's to be used in this treatment method, and the administration methods and formulations, are as described above. The use of the present compounds with SRI's in subjects striving to stop use of tobacco or nicotine provides alleviation of the usual painful and damaging symptoms of such subjects, including nervousness, irritability, craving, excessive appetite, anxiety, depression in many forms, inability to concentrate, and the like. The control or elimination of weight gain in the subject undergoing withdrawal from or reduction of tobacco or nicotine use is a particularly valuable and preferred benefit of the use of a present compound in combination with an SRI.

Therapeutic Applications

The compounds of formula I are useful for other important therapeutic purposes, as well as in combination with SRIs and in nicotine withdrawal or smoking cessation cases. In particular, the compounds are valuable for binding, blocking or modulating the serotonin-1A receptor, for binding, blocking or modulating the serotonin-2A receptor, for binding, blocking or modulating the serotonin-1D receptor, and for the treatment or prophylaxis of conditions caused by or influenced by defective function of these receptors. In particular, the compounds are useful for antagonism at the serotonin-1A receptor, the serotonin-2A receptor, the serotonin-1D receptor, and accordingly are used for the treatment or prevention of conditions caused by or affected by excessive activity of these receptors.

More particularly, the compounds of formula I are useful in the treatment of anxiety, depression, hypertension, cognitive disorders, psychosis, sleep disorders, gastric motility disorders, sexual dysfunction, brain trauma, memory loss, appetite disorders and obesity, substance abuse, obsessive-compulsive disease, panic disorder and migraine.

Anxiety and its frequent concomitant, panic disorder, may be particularly mentioned in connection with the present compounds. The subject is carefully explained by the Diagnostic and Statistical Manual of Mental Disorders, published by the American Psychiatric Association, which classifies anxiety under its category 300.02. It is understood that the following specific disorders are also included within the method of the present invention; "generalized anxiety disorder", "panic disorder", "social phobia", "social anxiety", "post traumatic stress disorder", "acute stress disorder", "anxiety due to general medical condition", "substance induced anxiety disorder", and "anxiety disorder not otherwise specified". A further particularly noted disorder is depression and the group of depression-related disorders, which are discussed above in the discussion of adjunctive therapy with SRIs. Further included within the scope of the term anxiety is "social functioning" as appreciated by one of ordinary skill in the art.

The unique combination of pharmacological properties possessed by the compounds of formula I permit those compounds to be used in a method of simultaneously treating anxiety and depression. The anxiety portion of the combined syndrome is believed to be attacked by the $5\text{-HT-}1_A$ receptor-affecting property of the compounds, and the depression portion of the condition is believed to be addressed by the reuptake inhibition property. Thus, administration of an effective amount, which is determined in an analogous manner as discussed hereinabove, of a compound of formula I, will provide a method of simultaneously treating anxiety and depression.

Pharmaceutical Compositions

The present invention provides pharmaceutical compositions of compounds of formula I, including the hydrates thereof, comprising, as an active ingredient, a compound of formula I in admixture or otherwise in association with one or more pharmaceutically acceptable carriers, diluents or excipients. It is customary to formulate pharmaceuticals for administration, to provide control of the dosage and stability of the product in shipment and storage, and the usual methods of formulation are entirely applicable to the compounds of formula I. Such compositions, comprising at least one pharmaceutically acceptable carrier, are valuable and novel because of the presence of the compounds of formula I therein. Although pharmaceutical chemists are well aware of many effective ways to formulate pharmaceuticals, which technology is applicable to the present compounds, some discussion of the subject will be given here for the convenience of the reader.

The usual methods of formulation used in pharmaceutical science and the usual types of compositions may be used according to the present invention, including tablets, chewable tablets, capsules, solutions, parenteral solutions, intranasal sprays or powders, troches, suppositories, transdermal patches and suspensions. In general, compositions contain from about 0.5% to about 50% of the compound in total, depending on the desired dose and the type of composition to be used. The amount of the compound, however, is best defined as the effective amount, that is, the amount of each compound which provides the desired dose to the subject in need of such treatment. The activity of the compounds do not depend on the nature of the composition, so the compositions are chosen and formulated solely for convenience and economy. Any compound may be formulated in any desired form of composition. Some discussion of different compositions will be provided, followed by some typical formulations.

Capsules are prepared by mixing the compound with a suitable diluent and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant is necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate.

Enteric formulations are often used to protect an active ingredient from the strongly acidic contents of the stomach. Such formulations are created by coating a solid dosage form with a film of a polymer which is insoluble in acidic environments, and soluble in basic environments. Exemplary films are cellulose acetate phthalate, polyvinyl acetate phthalate, hydroxypropyl methylcellulose phthalate and hydroxypropyl methylcellulose acetate succinate.

Tablets are often coated with sugar as a flavor and sealant, or with film-forming protecting agents to modify the dissolution properties of the tablet. The compounds may also be formulated as chewable tablets, by using large amounts of pleasant-tasting substances such as mannitol in the formulation, as is now well-established practice. Instantly dissolving tablet-like formulations are also now frequently used to assure that the subject consumes the dosage form, and to avoid the difficulty in swallowing solid objects that bothers some subjects.

When it is desired to administer the combination as a suppository, the usual bases may be used. Cocoa butter is a traditional suppository base, which may be modified by addition of waxes to raise its melting point slightly. Water-miscible suppository bases comprising, particularly, polyethylene glycols of various molecular weights are in wide use, also.

Transdermal patches have become popular recently. Typically they comprise a resinous composition in which the drugs will dissolve, or partially dissolve, which is held in contact with the skin by a film which protects the composition. Many patents have appeared in the field recently. Other, more complicated patch compositions are also in use, particularly those having a membrane pierced with pores through which the drugs are pumped by osmotic action.

The following typical formulae are provided for the interest and information of the pharmaceutical scientist.

Formulation 1

Hard gelatin capsules are prepared using the following ingredients:

|  | Quantity (mg/capsule) |
| --- | --- |
| Example #1 | 20 mg |
| Starch, dried | 200 mg |
| Magnesium stearate | 10 mg |
| Total | 230 mg |

As with any group of structurally related compounds which possess a particular generic utility, certain groups and configurations are preferred for compounds of formula I.

With respect to X, compounds of formula I wherein X is S are preferred. With respect to Y, compounds of formula I wherein Y is —C(=O)— or —CH(OH)— are preferred with Y equal to —C(=O)— being most preferred. With respect to $R_{1a}$, $R_{1b}$, $R_{1c}$, and $R_{1d}$, compounds of formula I wherein $R_{1a}$, $R_{1b}$, $R_{1c}$, and $R_{1d}$ are H, F, Cl, Br, OH, $C_1$–$C_4$ alkyl or $C_1$–$C_4$ alkoxy are preferred, with H being most preferred. With respect to $R_2$, compounds of formula I wherein $R_2$ is H, $C_1$–$C_4$ alkyl and —C(=O)NR$_7$R$_8$ are preferred, with H being most preferred. With respect to $R_3$, compounds of formula I wherein $R_3$ is H or methyl are preferred. With respect to $R_4$, compounds of formula I wherein $R_4$ is phenyl, naphthyl, cyclopentyl, cyclohexyl, 2-pyridyl, 3-pyridyl or 4-pyridyl are preferred with phenyl or 2-pyridyl being most preferred. With respect to $R_5$, compounds of formula I wherein $R_5$ is phenyl, naphthyl, cyclopentyl, cyclohexyl, 2-pyridyl, 3-pyridyl or 4-pyridyl are preferred with phenyl or cyclohexyl being most preferred. With respect to the piperidine ring on formula I, the following substitutions for $R_{6a}$ and $R_{6b}$ are preferred:

(a) 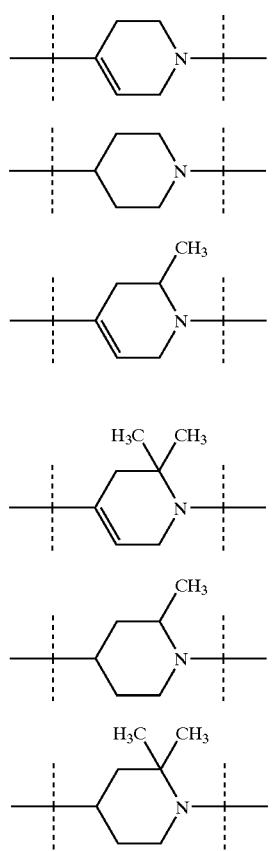

We claim:
1. A compound of the formula:

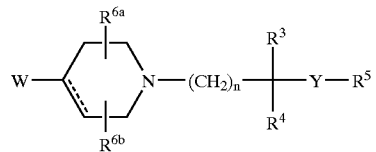

wherein:

W represents;

(a)
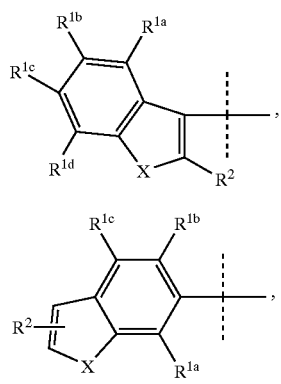

(b)

(c) 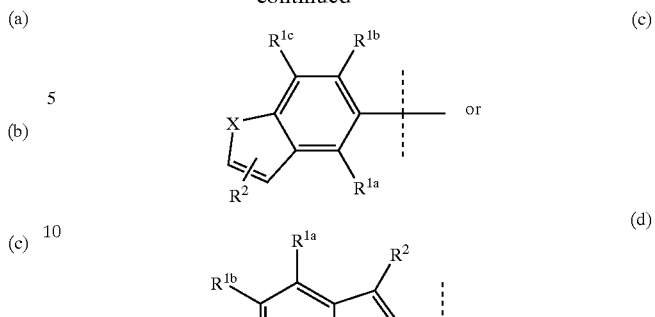

(d)

X represents O or S;
Y represents —C(=O)—, —CH(OH)—, —CH$_2$—, S, SO, or SO$_2$;
═══ represents a single or a double bond;
n is 1, 2, 3 or 4;
$R^{1a}$, $R^{1b}$, $R^{1c}$, $R^{1d}$, and $R^2$ are each independently H, F, Cl, Br, I, OH, C$_1$–C$_6$alkyl, C$_1$–C$_6$ alkoxy, halo(C$_1$–C$_6$) alkyl, phenyl, NO$_2$, —NR$_7$R$_8$, CN or phenyl substituted with from 1 to 3 substituents selected from the group consisting of F, Cl, Br, I, OH, C$_1$–C$_6$ alkyl, C$_1$–C$_6$ alkoxy, halo(C$_1$–C$_6$)alkyl, phenyl, NO$_2$, NH$_2$, or CN;
$R_3$ represents H, OH, hydroxy(C$_1$–C$_6$)alkyl, C$_1$–C$_6$ alkyl, or C$_1$–C$_6$ alkoxy;
$R_4$ represents aryl, heterocycle, C$_3$–C$_8$ cycloalkyl, aryl substituted with from 1 to 3 substituents selected from the group consisting of F, Cl, Br, I, OH, C$_1$–C$_6$ alkyl, C$_1$–C$_6$ alkoxy, halo(C$_1$–C$_6$)alkyl, phenyl, NO$_2$, NH$_2$, or CN; or heterocycle substituted with from 1 to 3 substituents selected from the group consisting of F, Cl, Br, I, OH, C$_1$–C$_6$ alkyl, C$_1$–C$_6$ alkoxy, halo(C$_1$–C$_6$)alkyl, phenyl, NO$_2$, NH$_2$, or CN;
$R_5$ represents aryl, heterocycle, C$_3$–C$_8$ cycloalkyl, aryl substituted with from 1 to 3 substituents selected from the group consisting of F, Cl, Br, I, OH, C$_1$–C$_6$ alkyl C$_1$–C$_6$ alkoxy, hydroxy(C$_1$–C$_6$)alkyl, halo(C$_1$–C$_6$) alkyl, phenyl, NO$_2$, NH$_2$, or CN; heterocycle substituted with from 1 to 3 substituents selected from the group consisting of F, Cl, Br, I, OH, C$_1$–C$_6$ alkyl, C$_1$–C$_6$ alkoxy, hydroxy(C$_1$–C$_6$)alkyl, halo(C$_1$–C$_6$) alkyl, phenyl, NO$_2$, NH$_2$, or CN; or C$_3$–C$_8$ cycloalkyl substituted with C$_1$–C$_4$ alkyl;
$R_{6a}$ and $R_{6b}$ are each independently H or C$_1$–C$_3$ alkyl;
$R_7$ and $R_8$ are each independently H, C$_1$–C$_6$ alkyl, aryl or aryl substituted with from 1 to 3 substituents selected from the group consisting of F, Cl, Br, I, OH, C$_1$–C$_6$ alkyl, C$_1$–C$_6$ alkoxy, halo(C$_1$–C$_6$)alkyl, phenyl, NO$_2$, NH$_2$, or CN;
or a pharmaceutically acceptable salt thereof.

2. A compound according to claim 1 wherein X is O.
3. A compound according to claim 1 wherein X is S.
4. A compound according to claim 1 wherein $R_2$ is H.
5. A compound according to claim 1 wherein n is 2.
6. A compound according to claim 1 wherein $R_3$ is H.
7. A compound according to claim 1 wherein $R_3$ is methyl.
8. A compound according to claim 1 wherein $R_4$ is 2-pyridyl.

9. A compound according to claim 1 wherein ═══ is a double bond.

10. A compound according to claim 1 wherein Y is —CO—.

11. A compound which is selected from the group consisting of:
a) 4-(6-benzo(b)thiophene-1,2,3,6-tetrahydropyridyl)-1-cyclohexyl-2-(2-pyridyl)butan-1-one;
b) 4-(5-benzo(b)thiophene-1,2,3,6-tetrahydropyridyl)-1-cyclohexyl-2-(2-pyridyl)butan-1-one;
c) 4-(2-benzo(b)thiophene-1,2,3,6-tetrahydropyridyl)-1-cyclohexyl-2-(2-pyridyl)butan-1-one; and
d) 4-(3-benzo(b)thiophene-1,2,3,6-tetrahydropyridyl)-1-cyclohexyl-2-(2-pyridyl)butan-1-one; or a pharmaceutically acceptable salt thereof.

12. A method of inhibiting the reuptake of serotonin and antagonizing the 5-HT$_{1A}$ receptor which comprises administering to a subject in need of such treatment an effective amount of a compound of the formula:

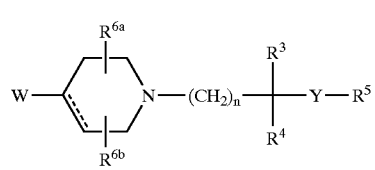

(I)

wherein:

W represents:

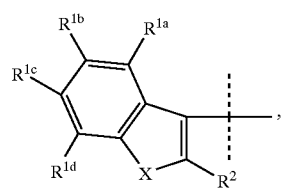

(a)

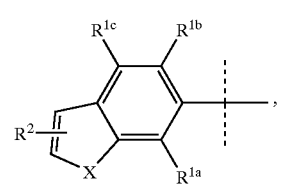

(b)

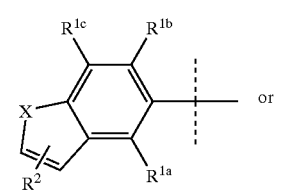

(c)

or

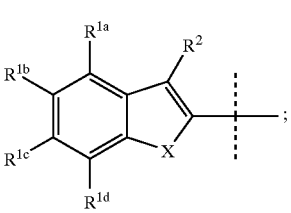

(d)

X represents O or S;
Y represents —C(═O)—, —CH(OH)—, —CH$_2$—, S, SO, or SO$_2$;

═══ represents a single or a double bond;

n is 1, 2, 3 or 4;

$R^{1a}$, $R^{1b}$, $R^{1c}$, $R^{1d}$, and $R^2$ are each independently H, F, Cl, Br, I, OH, $C_1$–$C_6$ alkyl, $C_1$–$C_6$ alkoxy, halo($C_1$–$C_6$) alkyl, phenyl, NO$_2$, —NR$_7$R$_8$, CN or phenyl substituted with from 1 to 3 substituents selected from the group consisting of F, Cl, Br, I, OH, $C_1$–$C_6$ alkyl, $C_1$–$C_6$ alkoxy, halo($C_1$–$C_6$)alkyl, phenyl, NO$_2$, NH$_2$, or CN;

$R_3$ represents H, OH, hydroxy($C_1$–$C_6$)alkyl, $C_1$–$C_6$ alkyl, or $C_1$–$C_6$ alkoxy;

$R_4$ represents aryl, heterocycle, $C_3$–$C_8$ cycloalkyl, aryl substituted with from 1 to 3 substituents selected from the group consisting of F, Cl, Br, I, OH, $C_1$–$C_6$ alkyl, $C_1$–$C_6$ alkoxy, halo($C_1$–$C_6$)alkyl, phenyl, NO$_2$, NH$_2$, or CN; or heterocycle substituted with from 1 to 3 substituents selected from the group consisting of F, Cl, Br, I, OH, $C_1$–$C_6$ alkyl, $C_1$–$C_6$ alkoxy, halo($C_1$–$C_6$)alkyl, phenyl, NO$_2$, NH$_2$, or CN;

$R_5$ represents aryl, heterocycle, $C_3$–$C_8$ cycloalkyl, aryl substituted with from 1 to 3 substituents selected from the group consisting of F, Cl, Br, I, OH, $C_1$–$C_6$ alkyl, $C_1$–$C_6$ alkoxy, hydroxy($C_1$–$C_6$)alkyl, halo($C_1$–$C_6$) alkyl, phenyl, NO$_2$, NH$_2$, or CN; heterocycle substituted with from 1 to 3 substituents selected from the group consisting of F, Cl, Br, I, OH, $C_1$–$C_6$ alkyl, $C_1$–$C_6$ alkoxy, hydroxy($C_1$–$C_6$)alkyl, halo($C_1$–$C_6$) alkyl, phenyl, NO$_2$, NH$_2$, or CN, or $C_3$–$C_8$ cycloalkyl substituted with $C_1$–$C_4$ alkyl;

$R_{6a}$ and $R_{6b}$ are each independently H or $C_1$–$C_3$ alkyl;

$R_7$ and $R_8$ are each independently H, $C_1$–$C_6$ alkyl, aryl or aryl substituted with from 1 to 3 substituents selected from the group consisting of F, Cl, Br, I, OH, $C_1$–$C_6$ alkyl, $C_1$–$C_6$ alkoxy, halo($C_1$–$C_6$)alkyl, phenyl, NO$_2$, NH$_2$, or CN;

or a pharmaceutically acceptable salt thereof.

13. A method of potentiating the action of a serotonin reuptake inhibitor comprising administering to a subject in of such treatment a compound formula:

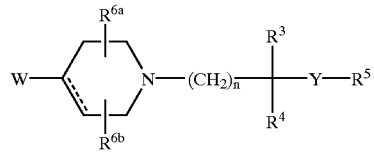

wherein:

W represents:

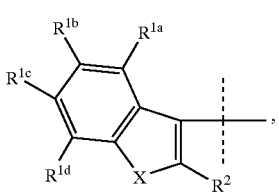

(a)

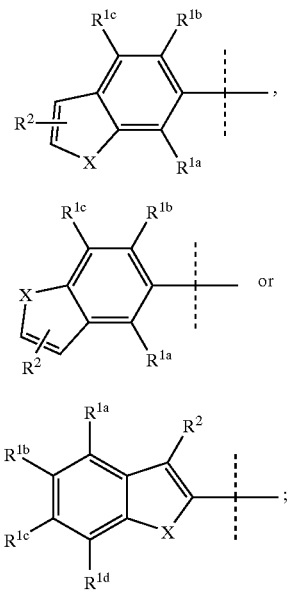

14. A method of treating depression comprising administering to a subject in need thereof an effective amount of a compound of formula:

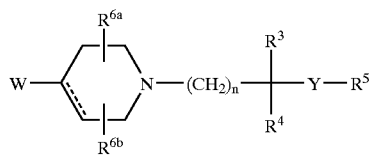

(I)

wherein:
W represents:

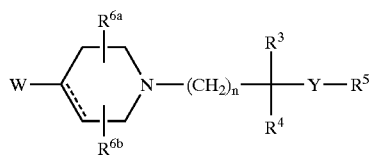

(I)

X represents O or S,
Y represents —C(=O)—, —CH(OH)—, —CH$_2$—, S, SO, or SO$_2$;
=== represents a single or a double bond;
n is 1, 2, 3 or 4;
R$^{1a}$, R$^{1b}$, R$^{1c}$, R$^{1d}$, and R$^2$ are each independently H, F, Cl, Br, I, OH, C$_1$–C$_6$ alkyl, C$_1$–C$_6$ alkoxy, halo(C$_1$–C$_6$) alkyl, phenyl, NO$_2$, —NR$_7$R$_8$, CN or phenyl substituted with from 1 to 3 substituents selected from the group consisting of F, Cl, Br, I, OH, C$_1$–C$_6$ alkyl, C$_1$–C$_6$ alkoxy, halo(C$_1$–C$_6$)alkyl, phenyl, NO$_2$, NH$_2$, or CN;
R$_3$ represents H, OH, hydroxy(C$_1$–C$_6$)alkyl, C$_1$–C$_6$ alkyl, or C$_1$–C$_6$ alkoxy;
R$_4$ represents aryl, heterocycle, C$_3$–C$_8$ cycloalkyl, aryl substituted with from 1 to 3 substituents selected from the group consisting of F, Cl, Br, I, OH, C$_1$–C$_6$ alkyl, C$_1$–C$_6$ alkoxy, halo(C$_1$–C$_6$)alkyl, phenyl, NO$_2$, NH$_2$, or CN; or heterocycle substituted with from 1 to 3 substituents selected from the group consisting of F, Cl, Br, I, OH, C$_1$–C$_6$ alkyl, C$_1$–C$_6$ alkoxy, halo(C$_1$–C$_6$)alkyl, phenyl, NO$_2$, NH$_2$, or CN;
R$_5$ represents aryl, heterocycle, C$_3$–C$_8$ cycloalkyl, aryl substituted with from 1 to 3 substituents selected from the group consisting of F, Cl, Br, I, OH, C$_1$–C$_6$ alkyl, C$_1$–C$_6$ alkoxy, hydroxy(C$_1$–C$_6$)alkyl, halo(C$_1$–C$_6$) alkyl, phenyl, NO$_2$, NH$_2$, or CN; heterocycle substituted with from 1 to 3 substituents elected from the group consisting of F, Cl, Br, I, OH, C$_1$–C$_6$ alkyl, C$_1$–C$_6$ alkoxy, hydroxy(C$_1$–C$_6$)alkyl, halo(C$_1$–C$_6$) alkyl, phenyl, NO$_2$, NH$_2$, or CN; or C$_3$–C$_8$ cycloalkyl substituted with C$_1$–C$_4$ alkyl;
R$_{6a}$ and R$_{6b}$ are each independently H or C$_1$–C$_3$ alkyl;
R$_7$ and R$_8$ are each independently H, C$_1$–C$_6$ alkyl, aryl, or aryl substituted with from 1 to 3 substituents selected from the group consisting of F, Cl, Br, I, OH, C$_1$–C$_6$ alkyl, C$_1$–C$_6$ alkoxy, halo(C$_1$–C$_6$)alkyl, phenyl, NO$_2$, NH$_2$, or CN;
or a pharmaceutically acceptable salt thereof.

15. A pharmaceutical composition comprising an effective amount of a compound as claimed in claim 1 in combination with a pharmaceutical acceptable carrier, diluent or excipients.